United States Patent
Moore et al.

(10) Patent No.: US 10,548,861 B2
(45) Date of Patent: Feb. 4, 2020

(54) USE OF UREIDOMUSTINE (BO-1055) IN CANCER TREATMENT

(71) Applicants: Academia Sinica, Taipei (TW); Memorial Sloan Kettering Cancer Center, New York, NY (US)

(72) Inventors: Malcolm Moore, New York, NY (US); Jae-Hung Shieh, New York, NY (US); Tsann-Long Su, Amawalk, NY (US); Te-Chang Lee, Taipei (TW)

(73) Assignees: Academia Sinica, Nankang, Taipei (TW); Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 15/745,639

(22) PCT Filed: Aug. 17, 2016

(86) PCT No.: PCT/US2016/047264
§ 371 (c)(1),
(2) Date: Jan. 17, 2018

(87) PCT Pub. No.: WO2017/031156
PCT Pub. Date: Feb. 23, 2017

(65) Prior Publication Data
US 2019/0008808 A1 Jan. 10, 2019

Related U.S. Application Data

(60) Provisional application No. 62/206,081, filed on Aug. 17, 2015.

(51) Int. Cl.
*A61K 31/167* (2006.01)
*A61K 31/17* (2006.01)
*A61K 45/06* (2006.01)
*A61P 35/02* (2006.01)

(52) U.S. Cl.
CPC ............ *A61K 31/167* (2013.01); *A61K 31/17* (2013.01); *A61K 45/06* (2013.01); *A61P 35/02* (2018.01)

(58) Field of Classification Search
None
See application file for complete search history.

(56) References Cited

U.S. PATENT DOCUMENTS

| | | | |
|---|---|---|---|
| 2008/0171765 A1* | 7/2008 | Su | C07C 275/42 514/291 |
| 2013/0178494 A1* | 7/2013 | Su | C07D 215/233 514/291 |

OTHER PUBLICATIONS

Ambati et al., Proceedings of the 106th Annual Meeting of the American Association for Cancer Research; Apr. 18-22, 2015; Philadelphia, PA. Philadelphia (PA): AACR; Cancer Res 2015; 75 (15 Suppl) (Year: 2015).*

(Continued)

*Primary Examiner* — Karl J Puttlitz
(74) *Attorney, Agent, or Firm* — Wood, Phillips, Katz, Clark & Mortimer

(57) ABSTRACT

Method of using ureidomustine (BO-1055), a water-soluble NDA cross-linking agent, in the treatment of a cancer, selected from the group consisting of various types of human leukemia [such as acute myeloid leukemia (ALL) and acute B Lymphoblastic leukemia (B-ALL)], lymphomas, small lung cell carcinoma (SCLC), sarcomas, and others.

5 Claims, 33 Drawing Sheets

(56) References Cited

OTHER PUBLICATIONS

Written Opinion, PCT/US16/47264, dated Oct 31, 2016 (Year: 2016).*
Lopes et al., Blood 2014 124:5483 (Year: 2014).*
Watson et al., Cancer,1962, vol. 15, 759-768 (Year: 1962).*
Kapuriya et al., Bioorganic & Medicinal Chemistry 19 (2011) 471-485 (Year: 2011).*
International Search Report and Written Opinion for corresponding PCT Application No. PCT/US2016/047264 dated Oct. 31, 2016.
Ambati, SR et al., "Ureidomustine, a novel DNA-crosslinking agent shows activity in sarcoma preclinical models and lacks toxicity in normal tissues", Cancer Research, Aug. 1, 2015. vol. 75, No. 15, p. 1, 1st and 2nd paragraph; p. 2, 1st and 2nd paragraphs.
Lopes, EC et al., "Pre-clinical evaluation of a novel DNA crosslinking agent, BO-1055 in B-cell Lymphoma", Blood, 2014, vol. 124, No. 21, p. 5483; p. 2, 1st paragraph.
Watson, WL et al., "Oat cell lunch cancer", Cancer, 1962, vol. 15, pp. 759-768; p. 766, left column, 2nd-4th paragraphs.
Kuo, C Y et al., "Repairing of N-mustard derivative BO-1055 induced DNA damage requires NER, HR, and MGMT-dependent DNA repair mechanisms", Oncotarget, Jul. 17, 2015, vol. 6, No. 28, pp. 25770-25783; abstract; figure 1A.

\* cited by examiner

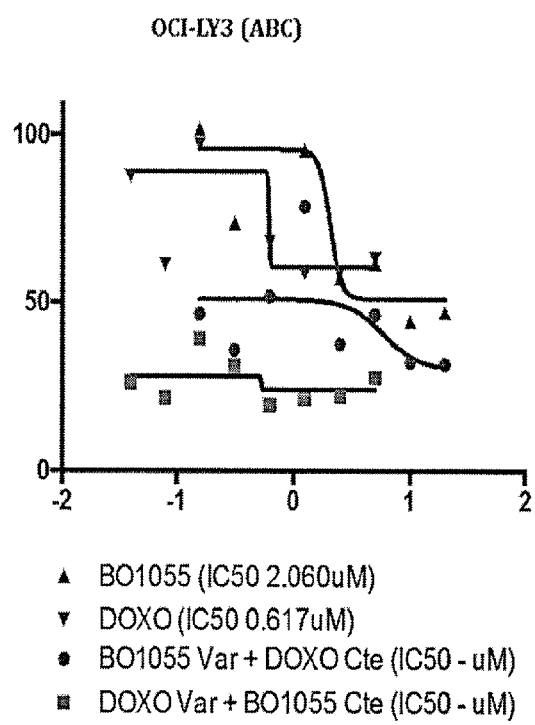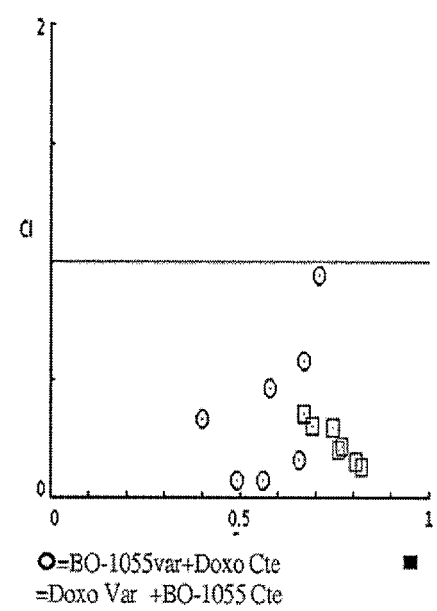
Fig. 23A
Fig. 23B

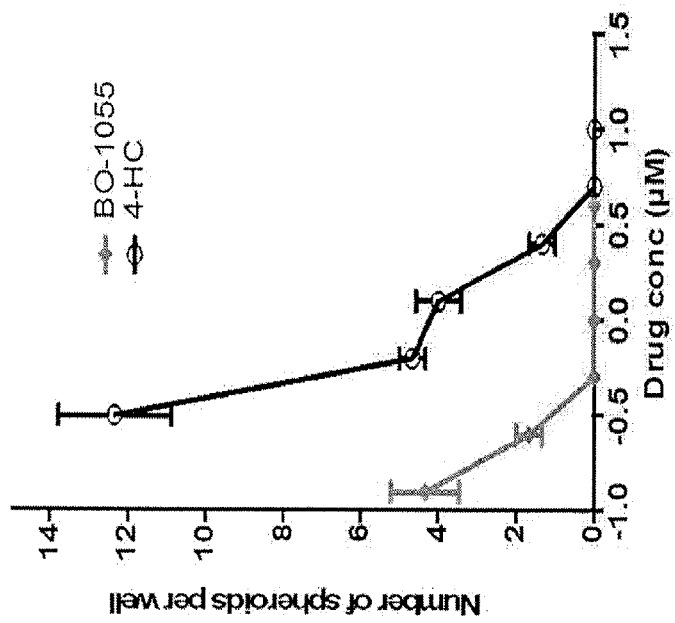
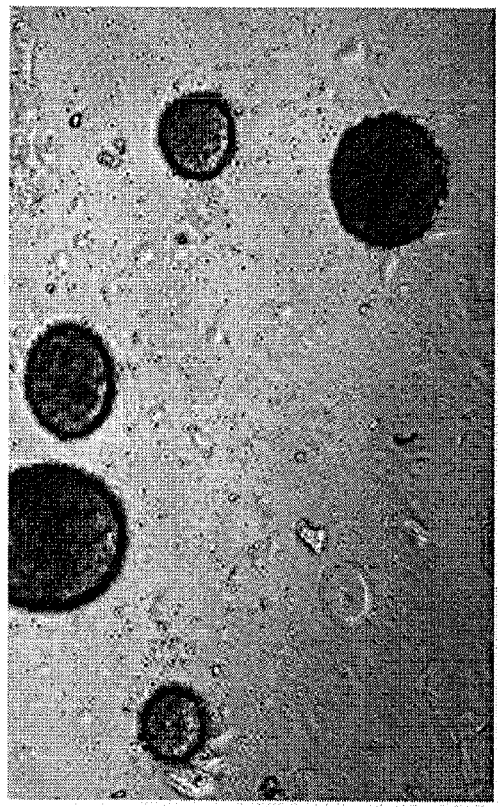
Fig. 26B
Fig. 26A

USE OF UREIDOMUSTINE (BO-1055) IN CANCER TREATMENT

BACKGROUND OF THE INVENTION

Ever since President Nixon's 1971 declaration of "War on Cancer," a set of assumptions has dominated cancer treatment for over 40 years. A war on cancer is a powerfully evocative metaphor that is directly responsible for a counterproductive and even potentially dangerous cell-kill treatment paradigm. (Oronsky et al. 2015). The pharmaceutical industry still develops cancer drugs to achieve the maximally tolerated dose (MTD) in an attempt to achieve a maximal and rapid cell killing.

Chemotherapy and radiation are the ultimate stress test for cancer cells, leading to an unintended "survival of the fittest" response. Chemotherapy, designed to wipe out the tumor, may actually have the opposite effect. This is because the chemosensitive cells, which normally keep the chemoresistant forms in check by competing for scarce space and resources, are killed off, while cancerous tumors adapt in Darwinian fashion to their environment and evolve by clonal expansion and genetic diversification.

(Greaves & Maley 2012). The price of this selection pressure is the emergence of acquired resistance and therapeutic failure, making aggressive therapy a self-defeating process.

Accordingly, there is a need for effective methods of treating cancer which do not result in significant toxicities against non-malignant tissues.

Alkylating agents are a set of anticancer compounds. Ureidomustine (also known as BO-1055) is a selective alkylating agent. It is described in U.S. Pat. No. 8,222,297 B2 and has the following structural formula:

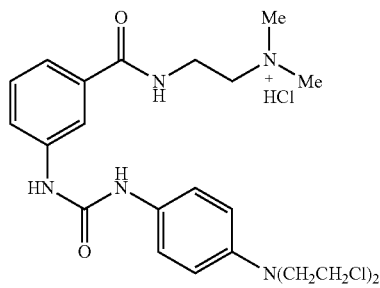

Although ureidomustine was previously suggested as an anti-tumor agent for some cancers, there remains a significant need for methods of treating other cancers with this compound.

SUMMARY OF THE INVENTION

In one embodiment, the invention provides a method of treating cancer in a patient in need thereof, comprising administering to said patient a therapeutically effective amount of ureidomustine, wherein said cancer is selected from the group consisting of leukemia, lymphoma, lung cancer, small lung cell carcinoma (SCLC), colorectal cancer, prostate cancer, renal cancer, glioblastoma, and sarcoma.

Ureidomustine (also referred to as "BO-1055" throughout this application) has the following structural formula:

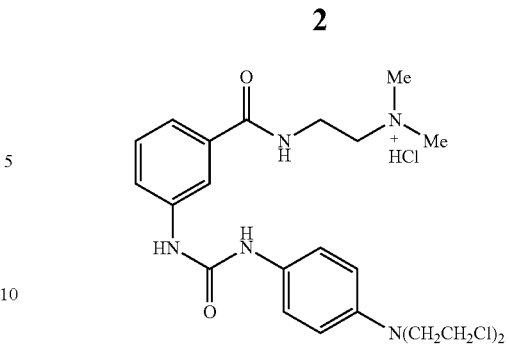

U.S. Pat. No. 8,222,297 describes ureidomustine, as well as a process of making this compound.

The term "ureidomustine" also encompasses pharmaceutically acceptable salts of BO-1055, isomers, enantiomers and racemic mixtures of the compound.

In a preferred embodiment, the cancer is selected from the group consisting of leukemia, lymphoma, SCLC and sarcoma.

In one embodiment, said leukemia comprises acute myeloid leukemia (AML), acute lymphoid or acute lymphoid or lymphoblastic leukemia (ALL, T-cell or B-cell subtypes), bi-phenotypic leukemia, chronic lymphocytic leukemia (CLL, T-cell or B-cell subtypes) and chronic myeloid leukemia (CML).

In a preferred embodiment, said treatment is effective to achieve a therapeutically significant reduction in the number of cancer cells while not resulting in significant toxicities against non-malignant tissues.

BRIEF DESCRIPTION OF THE DRAWINGS

FIG. 23A depicts a proliferation inhibition curve and $IC_{50}$ obtained by GraphPad Prism on DLBCL (ABC subtype) OCY-LY3 cancer cells treated with ureidomustine and doxorubicin (DOXO).

FIG. 23B depicts a Fa-Ci plot obtained by GraphPad Prism on the same cells.

FIG. 26A is graph showing inhibition of A673 Ewing's sarcoma onco-sphere formation in methylcellulose culture following treatment with various concentrations of ureidomustine or 4-Hydroperoxycyclophosphamide.

FIG. 26B is an image showing oncosphere formation in methylcellulose.

DETAILED DESCRIPTION OF THE INVENTION

Figure 1:
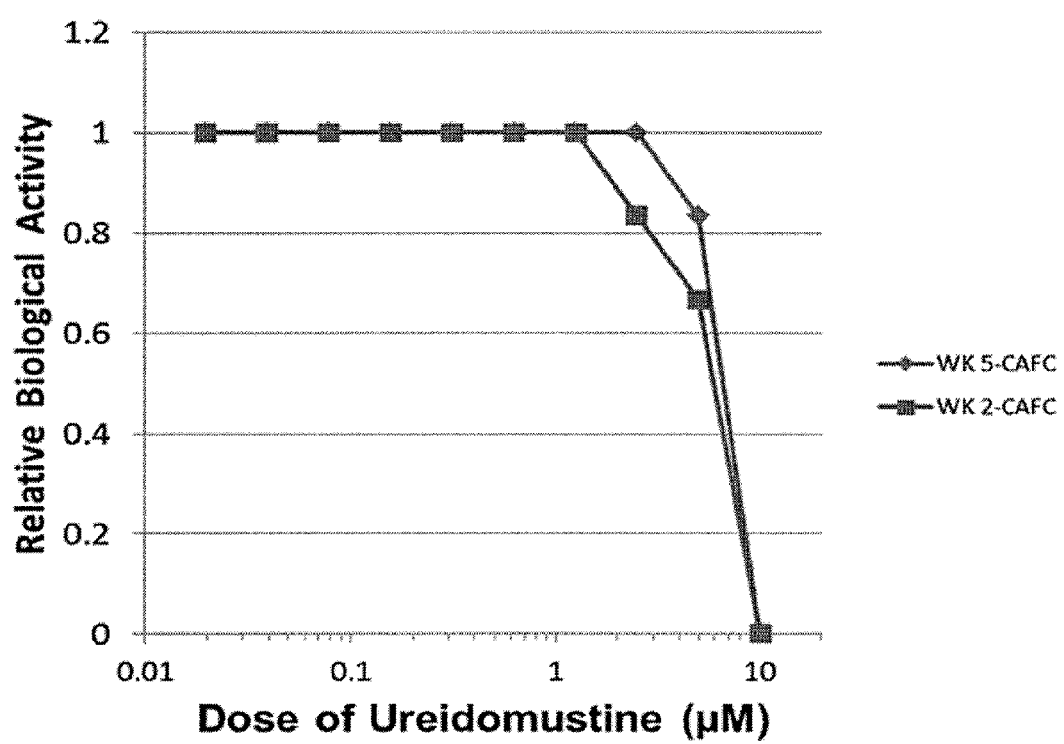
FIG. 1 shows a plot of dose of ureidomustine vs human cord blood (CB) hematopoietic progenitor cells (HPC/wk2-CAFC) and hematopoietic stem cells (HSC/wk5-CAFC).

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

In one embodiment, the invention provides a method of treating cancer in a patient in need thereof, comprising administering to said patient a therapeutically effective amount of ureidomustine, wherein said cancer is selected from the group consisting of leukemia, lymphoma, lung cancer, small lung cell carcinoma (SCLC), colorectal cancer, prostate cancer, renal cancer, glioblastoma, and sarcoma.

Preferably, ureidomustine is formulated in a pharmaceutical composition.

Ureidomustine (also referred to as "BO-1055" throughout this application) has the following structural formula:

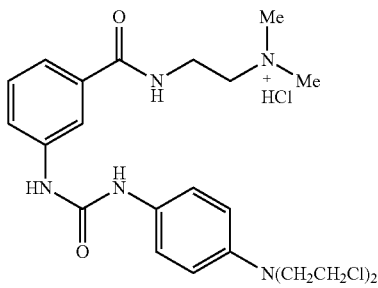

U.S. Pat. No. 8,222,297 describes ureidomustine, as well as a process of making this compound.

The term "ureidomustine" also encompasses pharmaceutically acceptable salts of BO-1055, isomers, enantiomers and racemic mixtures of the compound. The invention also encompasses methods of treatment of different cancers comprising administering metabolites of ureidomustine. The term "metabolite" means any substance produced from ureidomustine by metabolism or a metabolic process.

In a preferred embodiment, the cancer is selected from the group consisting of leukemia, lymphoma, SCLC and sarcoma.

In one embodiment, said leukemia comprises acute myeloid leukemia (AML), acute lymphoid or acute lymphoid or lymphoblastic leukemia (ALL, T-cell or B-cell subtypes), bi-phenotypic leukemia, chronic lymphocytic leukemia (CLL, T-cell or B-cell subtypes) and chronic myeloid leukemia (CML).

In a preferred embodiment, said treatment is effective to achieve a therapeutically significant reduction in the number of cancer cells while not resulting in significant toxicities against non-malignant tissues.

In one embodiment, the therapeutically effective dosage of ureidomustine is between about 3 and about 4 mg/kg per weight of a patient.

In some embodiments, the methods of the invention further comprise a co-administration of another anti-cancer active agent to the patient being treated with ureidomustine.

As defined herein, "contacting" means that the anti-tumor compound used in the present invention is introduced into a sample containing the receptor in a test tube, flask, tissue culture, chip, array, plate, microplate, capillary, or the like, and incubated at a temperature and time sufficient to permit binding of the anti-tumor compound to a receptor. Methods for contacting the samples with the anti-tumor compound or other specific binding components are known to those skilled in the art and may be selected depending on the type of assay protocol to be run. Incubation methods are also standard and are known to those skilled in the art.

In another embodiment, the term "contacting" means that the anti-tumor compound used in the present invention is introduced into a patient receiving treatment, and the compound is allowed to come in contact in vivo.

As used herein, the term "treating" includes preventative as well as disorder remittent treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a patient, tissue, organ or cells in contact with an anti-tumor compound. As used herein, administration can be accomplished in vitro, i.e. in a test tube, or in vivo, i.e. in cells or tissues of living organisms, for example, humans. In certain embodiments, the present invention encompasses administering the compounds useful in the present invention to a patient or subject. A "patient" or "subject", used equivalently herein, refers to a mammal, preferably a human, that either: (1) has a disorder remediable or treatable by administration of ureidomustine or (2) is susceptible to a disorder that is preventable by administering ureidomustine.

As used herein, "pharmaceutical composition" means therapeutically effective amounts of the anti-tumor compound together with suitable diluents, preservatives, solubilizers, emulsifiers, and adjuvants, collectively "pharmaceutically-acceptable carriers." As used herein, the terms "effective amount" and "therapeutically effective amount" refer to the quantity of active therapeutic agent sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of disease (e.g., pancreatic cancer, breast cancer); and (b) the reversal or stabilization of such disease. The optimum effective amounts can be readily determined by one of ordinary skill in the art using routine experimentation.

Pharmaceutical compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween (Polysorbate) 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including topical, parenteral, pulmonary, nasal and oral. In one embodiment the pharmaceutical composition is administered parenterally, paracancerally, transmucosally, tansdermally, intramuscularly, intravenously, intradermally, subcutaneously, intraperitonealy, intraventricularly, intracranially and intratumorally.

Further, as used herein "pharmaceutically acceptable carriers" are well known to those skilled in the art and include, but are not limited to, 0.01-0.1M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions administrable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions administered according to the invention incorporate particulate forms, protective coatings, protease inhibitors or permeation enhancers for various routes of administration, including parenteral, pulmonary, nasal and oral.

In yet another method according to the invention, a pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, for example liver, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The pharmaceutical preparation can comprise the anti-tumor compound alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the anti-tumor compound can be administered to a patient by, for example, subcutaneous implantation of a pellet. In a further embodiment, a pellet provides for controlled release of anti-tumor compound over a period of time. The preparation can also be administered by intravenous, intra-arterial, or intramuscular injection of a liquid preparation oral administration of a liquid or solid preparation, or by topical application. Administration can also be accomplished by use of a rectal suppository or a urethral suppository.

The pharmaceutical preparations administrable by the invention can be prepared by known dissolving, mixing, granulating, or tablet-forming processes. For oral administration, the anti-tumor compound may be mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intra-arterial, or intramuscular injection), the anti-tumor compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the anti-tumor compounds or their physiologically tolerated derivatives such as salts, esters, N-oxides, and the like are prepared and applied as solutions, suspensions, or emulsions in a physiologically acceptable diluent with or without a pharmaceutical carrier.

In another method according to the invention, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein ibid., pp. 317-327; see generally ibid).

For use in medicine, the salts of the anti-tumor compound may be pharmaceutically acceptable salts. Other salts may, however, be useful in the preparation of the compounds according to the invention or of their pharmaceutically acceptable salts. Suitable pharmaceutically acceptable salts of the compounds include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

The following Examples are provided herein to illustrate the invention, and should not be construed as limiting the invention in any way.

EXAMPLES

Example 1

Cytotoxicity of Ureidomustine
Ureidomustine (BO-1055) Toxicity Determined in a Panel of Human and Murine Benign Tissue Types.

To determine the toxicity of BO-1055 on non-malignant tissues, the inventors utilized the MTT and alamar blue assays (Hamid et al. 2004) to measure $IC_{50}$ values on 29 different normal human, murine or primate cell and tissue types (Table 1). BO-1055 was evaluated on all 29 normal tissues. Of these, 24/29 were highly resistant ($IC_{50} \geq 10.0$-$\geq 100.0$ μm) and 5 were moderately resistant ($IC_{50}$ 8.80-9.48 μM). The latter group included fallopian tube epithelium, fetal bone marrow stroma, cord blood CD34+ hematopoietic stem/progenitor cells in serum replacement medium, CAFC week 2 progenitors and CAFC week 5 hematopoietic stem cells.

TABLE 1

Cytotoxicity of water soluble ureidomustine (BO-1055) on various human, murine and primate normal tissues in vitro*. 72 hr cytotoxicity ($IC_{50}$, μM).

| Normal tissue | Tissue Type | 1055 |
|---|---|---|
| 16HBE SV40+ | Bronchial epithelium | ≥10.0 |
| BCI-NSI hTERT | Bronchial epithelium | 40.0 |
| BEAS2B SV40 | Bronchial epithelium | ≥10.0 |
| CCD-33Lu | Lung fibroblasts | 34.5 |
| NL31-PE | lung epithelium | ≥10.0 |
| FTE-hTERT | Fallopian epithelium | 9.48 |
| NOSE | Ovarian epithelium | ≥10.0 |
| HS578 | Breast epithelium | >100.0 |
| BMEC-hTert | BM endothelium | ≥10.0 |
| HUVEC | Umbilical endothelium | 60.5 |
| BMMSC | BM Mesenchyme | 32.8 |
| MS-5 (mouse) | Adult BM stroma | ≥10.0 |
| OP9 (mouse) | Calvarial stroma | ≥10.0 |
| HS27 | Adult BM stroma | 35.3 |
| HS5 | Adult BM stroma | ≥20.0 |
| FBMC | fetal BM stroma | 8.48 |
| MSC | Adipose Mesenchyme | 20.0 |
| HEL 299 | Fetal lung fibroblasts | ≥10.0 |
| HFL1 | fetal lung fibroblast | 14.2 |
| MRC5 | fetal lung fibroblast | ≥10.0 |
| Cutaneous | Fetal fibroblasts | ≥10.0 |
| IMR90 | fetal lung myofibroblast | 12.89 |
| CV1 primate | Renal fibroblasts | >100.0 |
| Cord Blood CFC | CFU-GM, BFU-E, CFU-C | 19.0 |
| Cord Blood 1 | CB CD34+ cells (no FCS) | 9.01 |
| Cord Blood 2 | CB CD34+ cells (+FCS) | 15.0 |
| Cord Blood | CB Wk2 CAFC HPC | 9.20 |
| Cord Blood | CB Wk5 CAFC HSC | 9.10 |
| SVGp12 | Astroglia | ≥10.0 |

*Description of benign cells used in Table 1.

MSC: Castro-Malaspina et al 1980 (first description of human mesenchymal stem cells and their progeny). Initial terminology CFU-F, current alternative nomenclature mesenchymal stromal cells (since only a minor fraction of the cell population has self-renewing stem cell features). BMEC-hTERT: human bone marrow microvascular endothelium-hTERT immortalized (Franco et al. 2001). MSC-hTERT: human hTERT immortalized bone marrow MSC (MacKenzie et al. 2000). MRCS: human embryonic lung fibroblasts immortalized with hTERT (Franco et al 2001, Wen et al 2006). Lung basal epithelium: immortalized with hTERT or SV40 (16HBE SV40+, BCI-NSI hTERT, BEAS2B SV40 T, CCD-33Lu, NL31-PE) (Shaykhiev et al 2013, Walters et al 2013). NOSE: normal human ovarian epithelium. HS5, HS27A: adult human bone marrow stromal cells immortalized with papilloma virus (Roecklein and Torok-Storb 1995). Renal fibroblasts were represented by an African green monkey (*Cercopithecus aethiops*) Raus sarcoma-transformed renal cell line (CV1) (Jensen et al. 1964). CB CD34+: human cord blood CD34+ cells (Mulloy et al 2003). CB CFC: Cord Blood hematopoietic progenitor cells (CFC) in semi-solid colony assay (Chung et al 2005). SVGp12: Astroglia an SV40 transformed human human fetal glial cell line.

Methods:
(i) CFC Assay

The toxicity of BO-1055 and other compounds on human hematopoietic progenitor cells, colony-forming Cells (CFC), was determined by culturing 500 purified human umbilical cord blood CD34+ cells/ml of Iscove's Modified Dulbecco Medium (IMDM) containing 1.2% methylcellulose, 20 ng/ml human c-Kit Ligand (KL), 20 ng/ml human IL-3, 20 ng/ml human G-CSF, 6 units/ml human EPO, 80 μM 2-mercaptoethanol, 2 mM L-glutamine, 50 units/ml penicillin, 50 μg/ml streptomycin, 0.125 mM hemin (Sigma), and 20% serum replacement (Life Technology, Grand island, NY) in the presence or absence of various dose of BO-1055 in triplicates. After 14 days, the colonies containing more than 50 cells/colony CFC were scored as CFC under a microscope and data were expressed as Mean±S.D., n=3.

(ii) CAFC Assay:

The toxicity of BO-1055 on human hematopoietic stem cells (HSC) in vitro was determined using the cobblestones area forming assay (CAFC)(Breems et al. 1994, Jo et al. 2000). A co-culture of 200 purified human umbilical cord blood CD34+ cells and MS-5 cells (murine stromal cells) was established in MEM alpha medium containing 12.5% fetal calf serum, 12.5% horse serum, $10^{-4}$ M monothiolglycerol, $10^{-6}$ M hydrocortisone, 50 μg/ml gentamicin, and 2 mM glutamine with or without various doses of the tested chemical. Half of medium was replenished with fresh medium weekly in triplicates. After 5 weeks, CAFC numbers of co-cultures were scored under a phase contrast microscope as areas of phase-dark cells beneath the stromal monolayer. For determining leukemic stem cells (LSC) the same assay was used but cultures are scored for cobblestone areas by 2 wks. Secondary re-passage of dissociated cobblestone area-forming cells onto fresh stroma was used to confirm the self-renewing ability of both HSC and LSC.

(iii) Effect of BO-1055 on Normal Human Tissues and Human Cancer Tissues 2,000~4,000 suspension cells or 1,000~2,000 adherent tumor cells/well (in a 96-well or 384-well plate) were cultured in IMDM medium containing 10% FCS in the presence or absence of various dose of BO-1055 in triplicates. After 72 hours, the cultures were pulsed with Alamar Blue overnight, and the fluorescent intensity of resulted cultures was measured by a Synergy H1 plate-reader (BioTek Inc). The suspension cells include purified CB CD34+ cells, primary human leukemia CD34+ cells, human leukemia and small cell lung carcinoma cell lines. The adherent cells were normal human umbilical endothelial cells (HUVEC), human bone marrow endothelial cells (BMEC), human bone marrow mesenchymal stem cells and various human solid tumor cell lines. When human CD34+ cells were used for drug screen, 500~1,000 cells/well were cultured in the presence of 20 ng/ml KL, 20 ng/ml IL-3, 20 ng/ml G-CSF and 6 units/ml EPO for 7-10 days prior to an addition of Alamar Blue.

As shown in Table 1, ureidomustine has relatively low toxicity against a panel of normal human and murine tissue and cell types. The panel includes four bronchial epithelial cell lines, three of these immortalized by transduction with hTERT or SV40 T antigen ($IC_{50}$>10.0-40.0 μM). Epithelial lines obtained from normal human ovarian surface epithelium and Fallopian tube basal epithelium were also resistant to BO-1055 ($IC_{50}$ 10.0-80.0 μM). Endothelium was represented by a bone marrow microvascular endothelial line and by normal umbilical cord-derived vascular endothelium, both resistant to BO-1055 ($IC_{50}$>10-60.5 μM). Mesenchymal stromal/stem cells (MSCs) and myofibroblasts were represented by 14 cell lines. Murine and human fetal and adult bone marrow or lung-derived MSCs, fetal cutaneous MSCs, adipose tissue-derived MSC and primate renal fibroblasts were relatively resistant to BO-1055 ($IC_{50}$ 8.48>100 μM).

The benign human bone marrow stromal cell lines HS5 and HS27A immortalized by papilloma virus were also resistant to BO-1055 cytotoxicity ($IC_{50}$>20-35.3 μM). Normal human hematopoietic cells in the screening panel included purified cord blood CD34+ cells in either serum-free or fetal calf serum-containing suspension culture ($IC_{50}$ 9.01-15.0 μM), or in semi-solid media colony-forming assay for hematopoietic progenitor cells/HPC (CFU-GM, BFUE, CFU-Mix ($IC_{50}$ 19.0 μM). The cobblestone area-forming assay (Breems et al 1994, Jo et al 2000) was used for quantitation of week 2 CAFC (HPC) and the documentation of their relative resistance to BO-1055 (mean $IC_{50}$ 9.20 μM in n=4 independent cord blood samples). Cord blood hematopoietic stem cells/HSC in week 5 CAFC assay were also relatively resistant to BO-1055 (mean $IC_{50}$ 9.10 μM in n=4 independent cord blood samples).

Example 2

Toxicity of Alkylating Drugs Carboplatin, Cisplatin, Temozolomide, Melphalan, Bendamustine and Cyclophosphamide (Active Metabolite 4-HC) Determined in a Panel of Human and Murine Normal Tissue Types.

The panel of 19 benign tissue types that was used to determine the cytotoxicity of BO-compounds was also used to screen for cytotoxicity of six commonly used alkylating drugs, carboplatin, cisplatin, temozolomide, melphalan, bendamustine and 4-HC (the active metabolite of cyclophosphamide) (Table 2).

Seven tissues were screened with carboplatin one was moderately sensitive ($IC_{50}$ of 1.70 μM). and 6/7 were highly resistant ($IC_{50}$ of 32.8->1000 μM). 12/14 lines were resistant to cisplatin ($IC_{50}$ of ≥20.0->100 μM) but 2/3 bronchial lines was sensitive ($IC_{50}$ 3.60-4.10 μM) as were cord blood hematopoietic progenitors ($IC_{50}$ 1.80 μM).

Temozolomide was evaluated on 7 tissues with 5 tissues highly drug resistant ($IC_{50}$ 20.0->100.0 μM) with one, the murine MS5 stromal line, showing weak resistance ($IC_{50}$ 5.5 μM) and the other, HUVEC endothelium, moderately sensitive.

MS5 was also quite sensitive to the other alkylating agents including melphalan ($IC_{50}$ 1.64 μM) and bendamustine ($IC_{50}$ 2.24 μM) and this was in contrast to the melphalan resistance of 13 other tissues tested ($IC_{50}$ 7.0-320.0 μM).

Bendamustine was cytotoxic to SV40-immortalized bronchial epithelium (16HBESV40+$IC_{50}$ 3.55 μM) and murine bone marrow stroma (MS-5 $IC_{50}$ 2.24 μM) but not to 10 other tissues tested ($IC_{50}$ 20.0-400.0 μM).

4-HC (the toxic metabolite of cyclophosphamide) had moderate cytotoxicity against 2 normal tissues ($IC_{50}$ 0.30-2.01 μM) and 5 were resistant ($IC_{50}$ 12.5-47.0 μM).

TABLE 2

In vitro 72 hr cytotoxicity (IC$_{50}$ µM) of the alkylating drugs Carboplatin, Cisplatin, Temozolomide (TMZ), Melphalan (Melp), Bendamustine and 4-HC (active metabolite of Cyclophosphamide) on various normal human, primate and murine tissues and telomerase- or SV40-immortalized normal tissues.

| Normal tissue | Tissue Type | Carboplatin | Cisplatin | TMZ | Melp | Benda Must | 4-HC |
|---|---|---|---|---|---|---|---|
| 16HBE SV40+ | Bronchial epithelia | 35.5 | 3.60 | nd | nd | 3.55 | nd |
| BCI-NSI hTERT | Bronchial epithelia | nd | 30.0 | ≥40.0 | 80.0 | 85.0 | 18.0 |
| BEAS2B SV40T | Bronchial epithelia | 120.0 | 4.10 | nd | nd | >10.0 | nd |
| FTE-hTERT | Fallopian epithelia | nd | 100.0 | nd | 320 | 400.0 | 12.5 |
| NOSE | Ovarian epithelia | nd | ≥25.0 | nd | ≥25.0 | nd | 0.30 |
| HS578 | Breast epithelium | nd | >100 | >100 | >100 | >100 | nd |
| BMEC-hTert | BM endothelium | nd | 20.0 | nd | 160.0 | 300.0 | nd |
| HUVEC | UBC endothelium | nd | 50.0 | 4.35 | 320.0 | 140.0 | 40.5 |
| BMMSC | BM stroma | 32.8 | 20.0 | ≥45.0 | 160.0 | 30.0 | 40.5 |
| MS-5 murine | Adult BM stroma | nd | 22.0 | 5.59 | 1.64 | 2.24 | nd |
| HS27 PV trans | Adult BM stroma | 35.3 | nd | nd | 9.10 | nd | nd |
| HS5 PV trans | Adult BM stroma | nd | nd | nd | >10.0 | nd | nd |
| FBMC | fetal BM stroma | nd | nd | nd | >10.0 | nd | nd |
| HFL1 | FL fibroblast | nd | nd | nd | 9.20 | nd | nd |
| MRC5 | FL fibroblast | 210.0 | nd | nd | nd | >20.0 | nd |
| IMR90 | FL myofibroblast | 1,000 | >100 | 57.3 | 56.8 | 32.3 | nd |
| CV1 (primate) | Renal fibroblasts | nd | 97.9 | >100 | 99.5 | >100 | 47.0 |
| Cord Blood | BFU-E, CFU-GM, CFC | 1.70 | 1.80 | nd | 7.00 | 10.0 | 2.01 |
| HL-1 | Cardiomyocyte | nd | 47.0 | nd | nd | nd | nd |

* Assay for IC$_{50}$ determined by 72 hr alamar blue assay.
nd = not determined
All the normal lines that were screened were resistant to carboplatin (7/7 IC$_{50}$ 23.0-1,000.0

Example 3

The Resistance of Normal Benign Murine Cells and Human Cord Blood CD34+ Cells, Hematopoietic Progenitor Cells (HPC) and Hematopoietic Stem Cells (HSC) to Ureidomustine (BO-1055) Cytotoxicity.

FIG. 1 shows the effect of ureidomustine on the proliferation of human CB CD34+HPC determined by wk 2 CAFC assay, and HSCs determined by the wk 5 CAFC assay (IC$_{50}$ 7.5-8.2 µM). There was variation in the sensitivity among independent CB samples tested with a mean IC$_{50}$ of 9.20 µM for wk2 CAFC (progenitor cells) and 9.10 µM for wk5 CAFC (HSC) (Table 2).

Figure 2:
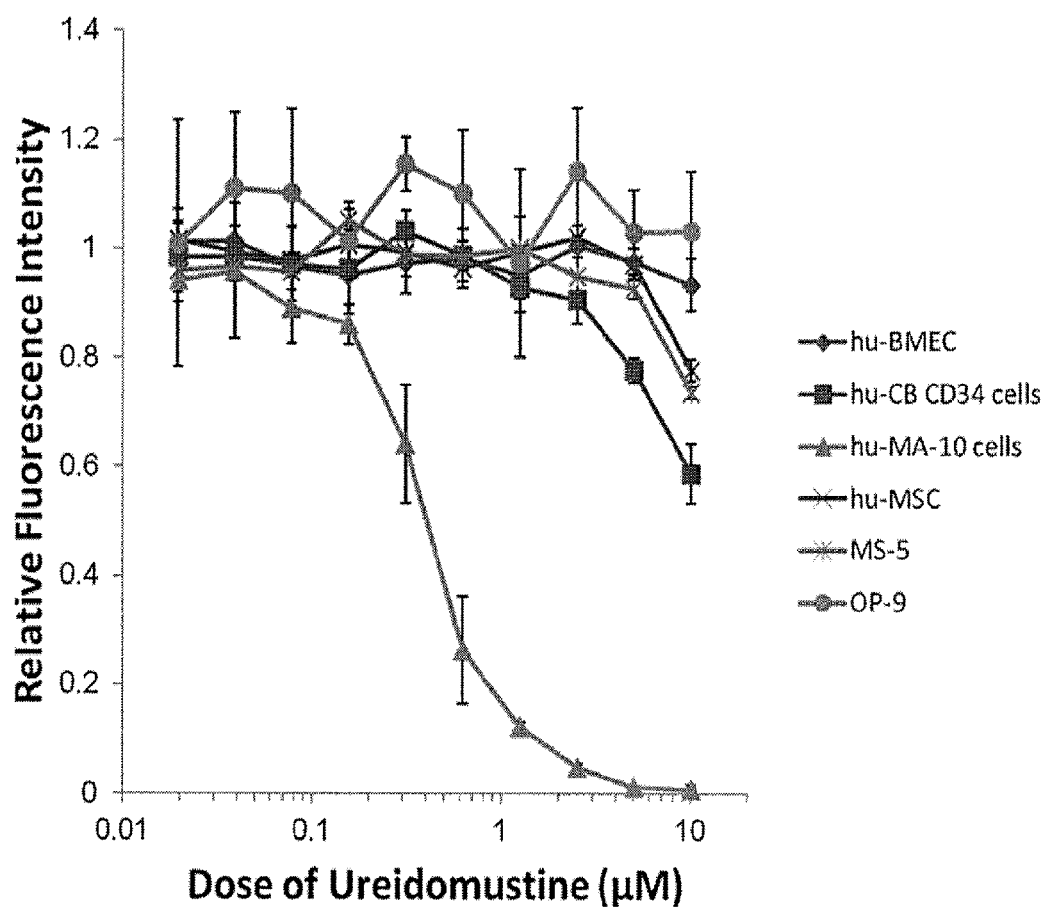
FIG. 2 shows a plot of dose of ureidomustine vs relative fluorescent intensity of normal cell types and a human acute myeloid leukemia (AML) cell line (MA-10).

FIG. 2 demonstrates effect of ureidomustine on the proliferation of various normal cell types compared to a human acute myeloid leukemia (AML) cell line.

Normal cells: Human cord blood CD34+ cells (hu-CB-CD34+). This subpopulation is enriched for hematopoietic progenitor cells (HPC ~30%) and hematopoietic stem cells (HSC ~5%). BM-derived endothelial cells (BMEC). Human mesenchymal stromal cells (MSC), murine MS-5 (BM-MSC) and murine OP9 (BM-MSC) cells. Human AML MA-10 cells: (hu-CB-CD34 cells transduced with MLL-AF9 fusion gene, cytokine-dependent). The relative fluorescence intensity represents the fluorescence intensity in the presence of ureidomustine divided by that in the absence of ureidomustine.

FIG. 2 shows the cytotoxicity of serial dilutions of BO-1055 as determined on various normal murine and human tissue types compared to an MLL-AF9 transformed leukemic cell line. Normal control tissues, including human bone marrow endothelium (BMEC), human MSC cells and murine MS-5 and OP9 bone marrow stromal cells were resistant to BO-1055 cytotoxicity (IC$_{50}$>10 µM), as were normal cord blood-CD34+ cells (IC$_{50}$>10 µM). This chemoresistance contrasts with the chemosensitivity seen with the MA-10 cell line derived from normal cord blood CD34+ cells retrovirally transfected with the MLL-AF9 leukemic translocation gene (IC$_{50}$ 0.35 µM) (Mulloy et al. 2003, Wunderlich and Mulloy 2009.) The introduction of a single leukemic gene into a normal HSC/HPC increased the toxicity of BO-1055>30-fold.

Example 4

In vivo Effects of BO-1055 Treatment on Peripheral Blood Hematologic Parameters of Normal C57131/6 Mice BO-1055 was administered to normal healthy mice using the MTD dose (30 mg/kg) and frequency (every other day x5) of i.v. This dose and schedule of drug administration found to produce regression of tumor cell line xenografts in Nude and NSG mice. There was no significant suppression in any of the 23/24 hematologic parameters evaluated (Table 3.). This is particularly striking in the case of neutrophils, red blood cells and platelets, whose levels are the most frequent dose limiting toxicities seen in clinic evaluation of alkylating drug therapy. There was a 3-4-fold increase in monocytes. The only negative effect was a modest reduction in WBC numbers due to mild lymphopenia at day 10 in the BO-treated group.

TABLE 3

Complete Blood Counts in healthy C57Bl/6 mice. Control PBS group n = 4 or BO-1055 treated with 30 mg/kg i.v on days 1, 3, 5, 8, 10. n = 4. RBC values are $10^6/\mu L$ All other values are $10^3/\mu L$

| Hematologic parameter | Control baseline | Control day 10 | BO-1055 baseline | BO-1055 day 10 |
|---|---|---|---|---|
| RBC (M/μL) | 9.62 ± 0.54 | 9.58 ± 0.24 | 9.22 ± 0.11 | 9.08 ± 0.18 |
| HGB (g/dL) | 13.90 ± 0.60 | 14.00 ± 0.21 | 13.50 ± 0.11 | 13.08 ± 0.25 |
| HCT (%) | 48.03 ± 2.24 | 48.43 ± 0.58 | 47.73 ± 0.66 | 46.30 ± 1.04 |
| MCV (fL) | 50.00 ± 0.59 | 50.57 ± 1.04 | 51.75 ± 0.27 | 51.03 ± 1.25 |
| MCH (pg) | 14.47 ± 0.23 | 14.60 ± 0.25 | 14.65 ± 0.10 | 14.40 ± 0.15 |
| MCHC (g/dL) | 28.93 ± 0.33 | 28.90 ± 0.12 | 28.30 ± 0.17 | 28.28 ± 0.42 |
| RDW-SD (fL) | 32.57 ± 0.66 | 33.20 ± 0.67 | 33.95 ± 0.69 | 32.48 ± 0.29 |
| RDW-CV (%) | 24.37 ± 0.64 | 24.23 ± 1.11 | 23.98 ± 0.44 | 23.18 ± 0.64 |
| RET (K/μL) | 404.7 ± 6.73 | 485.5 ± 84.3 | 419.4 ± 10.01 | 426.9 ± 5.92 |
| RET (%) | 4.23 ± 0.21 | 5.11 ± 1.00 | 4.55 ± 0.10 | 4.72 ± 0.37 |
| PLT (K/μL) | 908.7 ± 178.9 | 844.3 ± 181.3 | 1122.5 ± 38.4 | 1108.3 ± 76.1 |
| PDW (fL) | 7.20 ± 0.25 | 7.07 ± 0.2 | 6.65 ± 0.05 | 7.40 ± 0.24 |
| MPV (fL) | 6.30 ± 0.17 | 6.17 ± 0.22 | 6.05 ± 0.10 | 6.38 ± 0.09 |
| WBC (K/μL) | 8.63 ± 1.31 | 13.60 ± 0.96 | 8.13 ± 0.76 | 5.34 ± 0.99 |
| NEUT (K/μL) | 0.86 ± 0.10 | 1.92 ± 0.46 | 1.66 ± 0.30 | 1.90 ± 0.37 |
| LYMPH (K/μL) | 7.55 ± 1.21 | 11.34 ± 1.36 | 6.21 ± 0.67 | 2.90 ± 0.92 |
| MONO (K/μL) | 0.06 ± 0.02 | 0.09 ± 0.02 | 0.16 ± 0.04 | 0.39 ± 0.06 |
| EO (K/μL) | 0.15 ± 0.02 | 0.24 ± 0.03 | 0.08 ± 0.02 | 0.13 ± 0.03 |
| BASO (K/μL) | 0.01 ± 0.01 | 0.01 ± 0.01 | 0.03 ± 0.01 | 0.02 ± 0.01 |
| NEUT (%) | 10.07 ± 0.50 | 14.70 ± 4.57 | 20.48 ± 3.61 | 37.20 ± 7.11 |
| LYMPH (%) | 87.23 ± 0.78 | 82.77 ± 4.85 | 76.45 ± 3.60 | 51.63 ± 7.32 |
| MONO (%) | 0.73 ± 0.17 | 0.67 ± 0.07 | 1.83 ± 0.39 | 7.80 ± 1.29 |
| EO (%) | 1.87 ± 0.39 | 1.80 ± 0.36 | 0.95 ± 0.18 | 2.93 ± 1.18 |
| BASO (%) | 0.10 ± 0.06 | 0.07 ± 0.03 | 0.30 ± 0.08 | 0.45 ± 0.16 |

Example 5

Pathological Evaluation of Various Tissues of Mice Bearing Prostate 22Rv/HL2 Tumor Xenografts Recovered after Cessation of Treatment with BO-1055.

Figure 3:
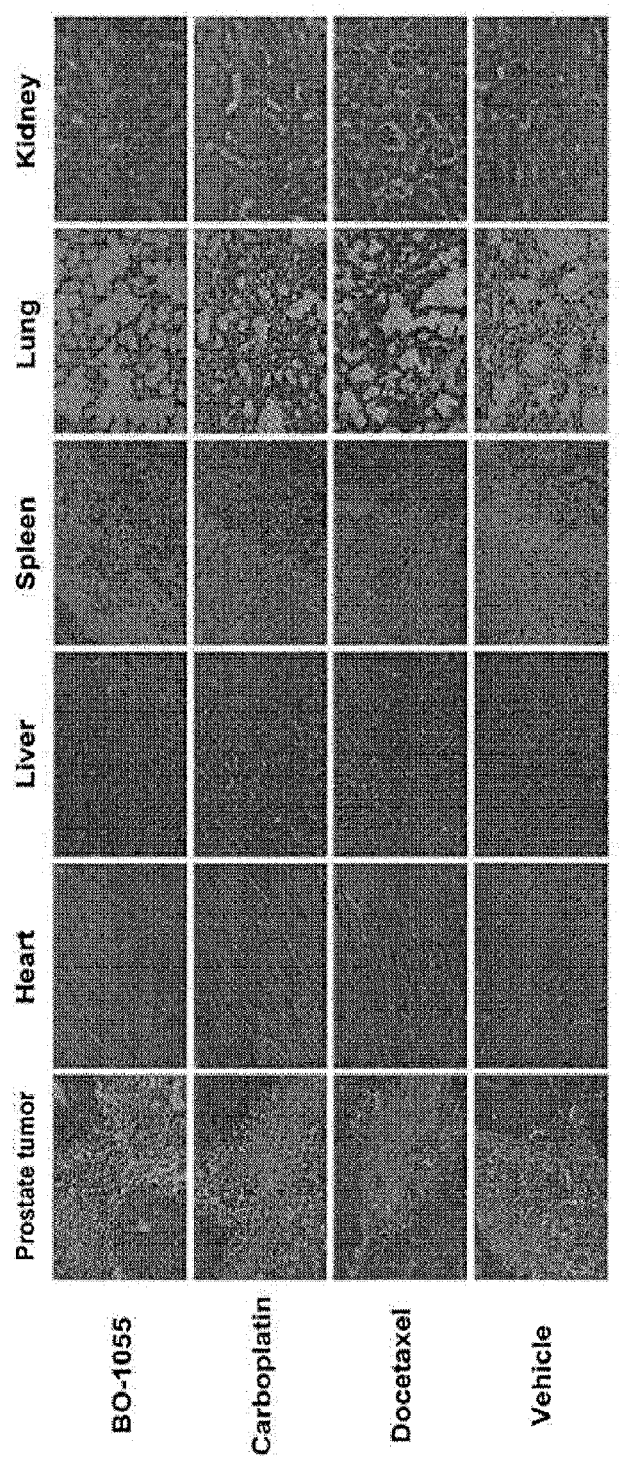
FIG. 3 shows photographs of pathological examination of different organs taken 42 days after administration of ureidomustine (BO-1055), carboplatin, docetaxel and control to mice.

FIG. 3 depicts the results of pathological examination of different organs from the ureidomustine (BO-1055), carboplatin, and docetaxel-treated mice 42 days after starting of drug treatment.

The inventors have examined the primary toxicity of BO-1055 and two positive control compounds (Carboplatin, Docetaxel) in nude mice bearing prostate 22Rv/HL2 tumor xenografts (orthotropic implantation in nude mice). The average body-weight of the drug-treated mice recovered on day 35-40, after cessation of treatment with BO-1055, indicating that ureidomustine has low toxicity to the host. We have also examined the pathologic changes in these treated mice (FIG. 3). Different organs of treated mice were removed, fixed, and stained on day 42 after onset of drug administration, for pathological examination.

There was no apparent pathological change in heart, liver, spleen, lung and kidney between the control group and the drug treated groups, indicating that ureidomustine and the two positive control compounds (Carboplatin, Docetaxel) have very little toxicity to the host and the treated mice rapidly recovered their body weight after ceasing drug treatment.

Example 6

Blood Chemistry and Complete Blood Count of Nude Mice with Orthotopic Implantation of the Prostate Cell Line 22Rv/HL2 24 Hrs after BO-1055 Treatment (30 m/Kg Every Second Day for 42 Days)

The blood was collected 24 hrs after the last treatment from the mice (n=3) bearing prostate 22Rv/HL2 (orthotropic implantation) for blood chemistry testing (Table 4) and complete blood count (Table 5). The results showed that AST (aspartate aminotransferase) was increased in all mice treated with Carboplatin, Docetaxel, and B01055 (Table 4). The blood urea nitrogen (BUN) is slightly increased in the BO-1055 treated mice, but does not change the level of uric acid (UA) in blood.

TABLE 4

Results of Blood Chemistry Test: blood was collected 24 hrs after the last drug treatment of the mice (n = 3).

| | AST (U/L) | ALT (U/L) | CREA (mg/dL) | BUN (mg/dL) | UA (mg/dL) |
|---|---|---|---|---|---|
| Vehicle | 77.10 | 50.60 | 0.32 | 25.02 | 3.30 |
| Carboplatin | 119.15 | 64.85 | 0.31 | 21.17 | 1.97 |
| BO-1055 | 102.17 | 56.83 | 0.38 | 37.23 | 3.73 |
| Docetaxel | 108.60 | 54.08 | 0.32 | 21.93 | 3.60 |

The complete blood count (Table 5) revealed that BO-1055 and both carboplatin and docetaxel lowered white blood cell (WBC), neutrophil (NEU), and the platelet (PLT) count. However, there is no significant difference in the degree of leukopenia resulting from treatment with the three compounds.

TABLE 5

Complete blood cell counts in nude mice with an orthotropic implanted human prostate cancer cell line 22Rv/HL2 and treated with BO-1055, carboplatin or docetaxel. (Blood was collected 24 hrs after the last drug treatment n = 3).

|  | WBC | NEU | LYM | MONO | EOS | BASO | RBC | PLT |
|---|---|---|---|---|---|---|---|---|
| Vehicle | 5.10* | 1.89 | 2.86 | 0.05 | 0.16 | 0.05 | 9.64 | 897 |
| Carboplatin | 1.97 | 1.13 | 0.60 | 0.07 | 0.13 | 0.03 | 9.37 | 369 |
| BO-1055 | 2.98 | 0.83 | 1.52 | 0.08 | 0.14 | 0.06 | 9.52 | 195 |
| Docetaxel | 2.49 | 1.34 | 0.66 | 0.04 | 0.12 | 0.08 | 7.55 | 308 |

*RBC values are $10^6/\mu L$ All other values are $10^3/\mu L$

Example 7

Determination of the Pharmacokinetic Profile of BO-1055.

The pharmacokinetics (PK) of ureidomustine were evaluated in healthy male Sprague Dawley rats following a single intravenous and oral administration of BO-1055 (Table 6). A single intravenous dose was administered via an indwelling catheter in the jugular vein to a group of 2 male rats at a dose level of 1.0 mg/kg. The formulations were prepared as a solution in 5.0% w/v DMSO with 10% w/v Cremophor in distilled water. The test compound, BO-1055 was administered once via oral gavage to another group of 2 male rats at a dose level of 10 mg/kg. The formulations were prepared as a solution in 0.5% w/v CMC in distilled water. Serial blood samples were collected from the jugular vein catheter up to 24 h post-dose from all animals in groups. Concentration levels of BO-1055 were determined in plasma using a validated LC-MS/MS assay with a lower limit of quantification (LLOQ) of 2.5 ng/mL. The plasma concentration-time data above the LLOQ at each dose level were used in the calculation of pharmacokinetic parameters of BO-1055 using the validated program WinNonlin™, version 5.2.1.

Pharmacokinetic parameters are summarized in Table 6.

The key observations from the toxicokinetic portion of this study are: (i) No quantifiable levels at any sampling time of BO-1055 were found after oral administration of 10 mg/kg (LLOQ: 2.5 ng/mL); (ii) There is no oral absorption after oral administration of BO-1055 (iii) BO-1055 exhibited low plasma clearance (Mean CL: 18.00 mL/min/kg); (iv) Mean apparent volume of distribution at steady state was 0.15 L/kg; (v) BO-1055 has a half-life of $t_{1/2}$=0.58 h in the rat model (n=2).

using a validated HPLC-photodiode array detection assay (Lin et al 2008). All pharmacokinetic analysis was carried out using the WinNonlin Standard Edition Version 1.0 (Scientific Consulting Inc., Apex, N.C., USA). The results showed that the mean apparent elimination half-life ($t_{1/2}$) of BO-1055 was 0.77 h (46.4 min) (Table 7). The area under curve (AUC), clearance (Cl) and maximum concentration (Cmax) were 267±65.3 min µg/mL, 39.4±10.6 mL/min per kg and 13.4±6.17 µg/mL, respectively. The results demonstrated that BO-1055 has an acceptable PK profile with a rapid distribution and a slow elimination after administration (10 mg/kg, iv. injection) in rats. After a short intravenous administration time at the dose of 10 mg/kg, ureidomustin was found to be quickly distributed to all organs in the rats, and accumulated mainly in the kidney, with only a limited amount detected in the brain (Chien et al. 2013).

TABLE 7

Pharmacokinetic parameters of BO-1055 (ureidomustine) following administration (10 mg/kg, via intravenous injection in rats (n = 5) (Chien et al. 2013)

| Pharmacokinetic Parameter | |
|---|---|
| $t_{1/2}$ | 46.4 ± 13.1 min |
| AUC | 267 ± 65.3 min µg/mL |
| Cl | 39.2 ± 10.6 mL/min per kg |
| Cmax | 13.4 ± 6.17 µg/mL |

$t_{1/2}$: half-life;
AUC: the area under curve;
Cl: Clearance;
Cmax: maximum concentration

TABLE 6

Summary of Pharmacokinetic parameters of BO-1055 (ureidomustine) following Intravenous or oral dose to rats (Chien et al 2013).

| Group | Dose (mg/kg) | C0 (ng/mL) | Cmax (ng/mL) | Tmax (h) | $t_{1/2}$ (h) | AUC (0-last) (h * ng/mL) | AUC (0-∞) (h * ng/mL) | CLss (mL/min/kg) | Vss (L/kg) |
|---|---|---|---|---|---|---|---|---|---|
| IV (N = 2) | 1 | 11980 | ND | ND | 0.58 | 925.81 | 934.93 | 18.00 | 0.15 |
| PO (N = 2) | 10 | ND | ND | ND | ND | ND | ND | ND | ND |

ND: Not determined.
Data is not appropriate for determination of PK parameter for the group.

The inventors further studied the PK of BO-1055.

Male Sprague-Dawley rats (6 weeks, 5 male rats) were treated with BO-1055 as a single intravenous administration via femoral vein by bolus injection (over 1 min) at a dose level of 10 mg/kg in 0.9% normal saline (NS). Serial blood samples were collected from the jugular vein at 0, 5, 10, 15, 30, 45, 60, 90, 120, 150, 180, 240, 300, 360 min after dosing. Concentration levels of BO-1055 were determined in plasma Example 8

Mechanism of Action of Ureidomustine
i) Ureidomustine Induces DNA Inter-strand Cross-linking (Kapuriya et al 2011)

The mechanism of action of ureidomustine was investigated by alkaline agarose gel shifting assay and compared with the alkylating drug Melphalan. The gel shows that ureidomustine is able to induce DNA inter-strand cross-linking, suggesting that DNA cross-linking may be the main mechanism of action for this agent.

Figure 4:
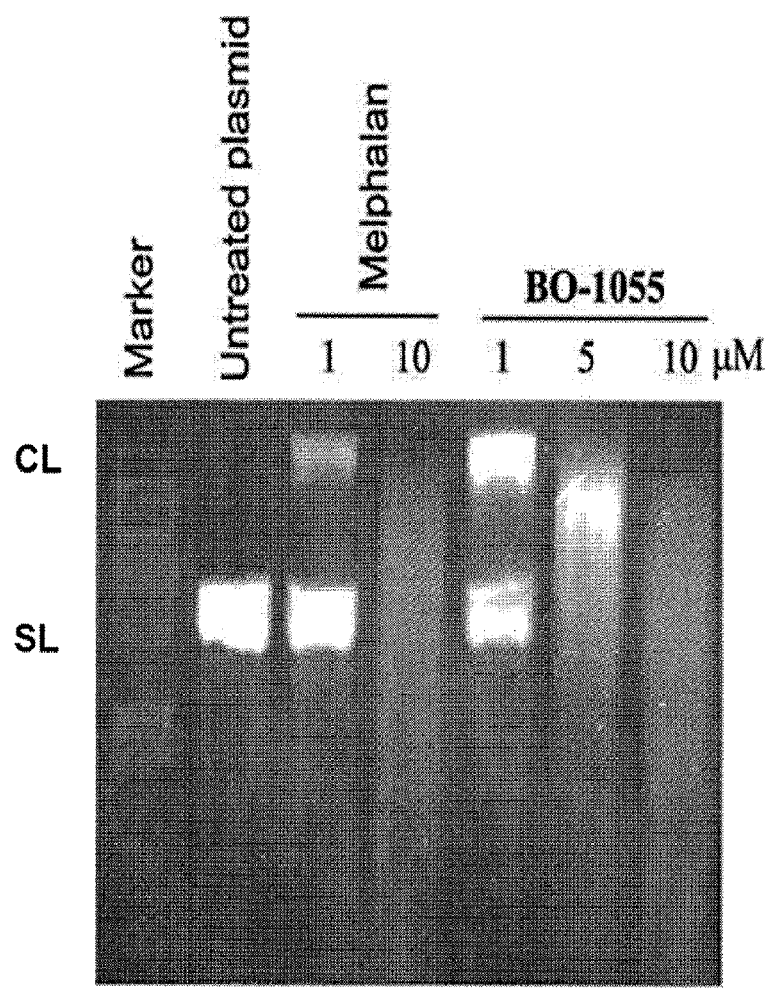
FIG. 4 shows a photograph of DNA cross-linking gel shift assay for ureidomustine.

FIG. 4 shows a representative DNA cross-linking gel shift assay for ureidomustine (BO-1055) at various concentrations as indicated. Control lane shows single stranded DNA (SL), while cross-linking (CL) shown in all tested lanes is DNA double-stranded cross linking. Melphalan (1 and 10 µM) was used as a positive control.

ii) Ureidomustine Induces G2M Arrest (Kapuriya et al 2011).

The inhibitory effect of ureidomustine on cell cycle distribution was studied in human non-small lung carcinoma H1299 cells. Ureidomustine treatment induced significant G2/M arrest in these cells. Furthermore, the inventors also found increased sub-G1 populations following ureidomustine treatment (FIG. 5).

Figure 5:
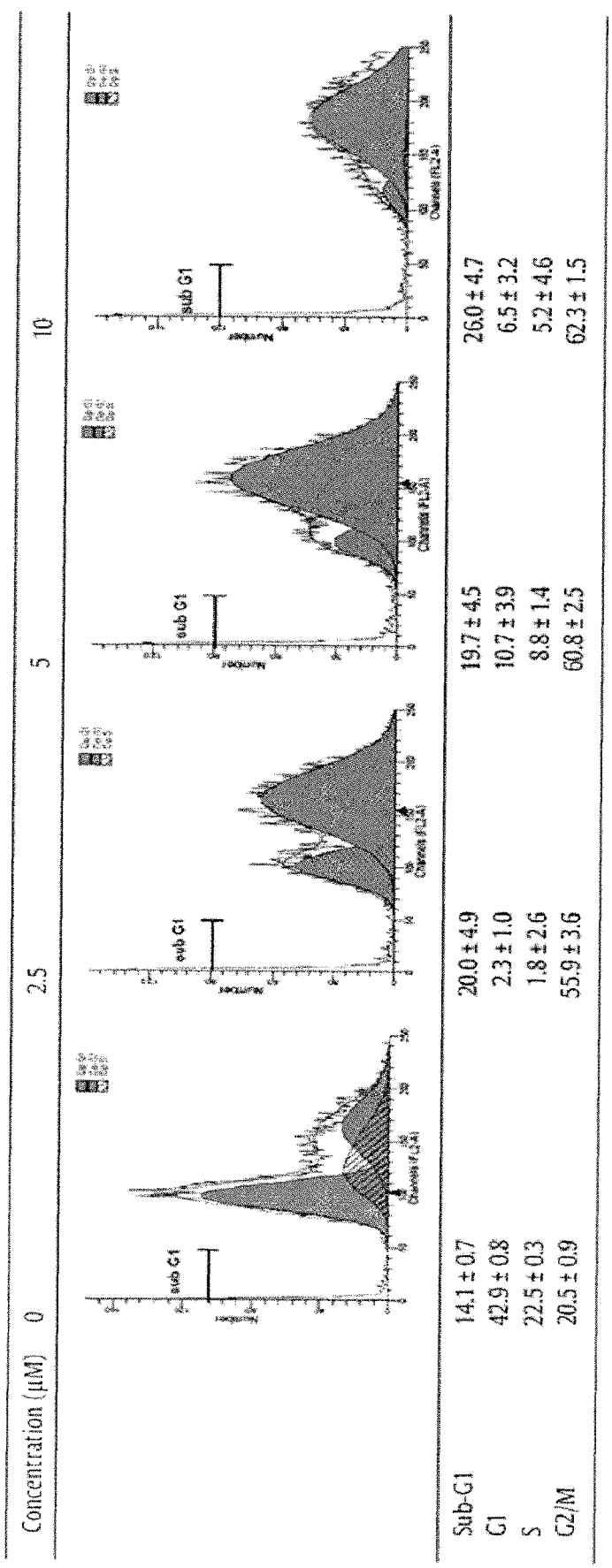
FIG. 5 shows a flow cytometry cell cycle distribution of non-small lung carcinoma H1299 cells following ureidomustine treatment.

FIG. 5 shows cell cycle inhibition in human non-small cell lung adenocarcinoma H1299 by treating with ureidomustine.

(iii) Absorption, Distribution, Metabolism, and Elimination (ADME) Studies of BO-1055

ADME studies were carried out and are summarized in Table 8. The Caco-2 intestinal cells penetration test indicates that compound BO-1055 cannot penetrate the intestinal cells and pharmacokinetic studies indicate that the drug cannot be administered and absorbed following oral administration. The drug/protein binding rate is high (99%) indicating that this can provide a drug reserve allowing slow drug release. The microsome stability test was 75%, indicating the compound may be removed via hepatic metabolism. Low hERG binding indicated that the tested compound is unlikely to produce cardiac toxicity.

TABLE 8

Summary of early ADME studies of ureidomustine

| Items for ADME studies | Evaluation Criteria | Test results |
| --- | --- | --- |
| Caco-2<br>Papp, apparent<br>permeability coefficient<br>(cm/sec). (10 µM)) | Papp (A to B)<br>High standard = 18.2 × 10−6 cm/sec<br>(Propranolol)<br>Low standard = 0.88 × 10−6 cm/sec<br>(Rodamin 123) | Papp (A to B) = ND (10 µM)<br>Papp (B to A) = 7.5 × 10−6 cm/sec<br>(10 µM)<br>Low intestinal permeability |
| P-glycoprotein (P-gp)<br>efflux transporter. | Efflux ratio < 2 | Efflux ratio: ND<br>Possible P-gp liabilities |
| Protein binding | High standard = 99%<br>(Warfarin, 1 µM)<br>Low standard = 17%<br>(Acetaminophen, 10 µM) | 99% (2 hr)<br>High Human plasma protein<br>binding = 1% free |
| Microsome Stability | High standard = 95%(60 mins)<br>(7-EC, 2 µM)<br>Low standard = 5%(60 mins)<br>(Warfarin, 2 µM) | 75% (60 mins turnover %)<br>(Positive control 7-<br>EC ≥ 82%)<br>High intrinsic clearance |
| hERG Binding assay for<br>identification of<br>potentially cardiotoxic<br>compounds<br>Inhibition ($IC_{50}$) | >1 µM<br>High liability: Astemizole<br>($IC_{50}$ = 4-6 nM) | 12.6 µM<br>low hERG binding. Not<br>cardiotoxic |
| Early PK (Oral<br>Bioavailability) | For oral<br>F > 20%, $t_{1/2}$ > 0.5 hr | No Oral Absorption<br>$t_{1/2}$ = 0.58 hr (IV) |

Example 9

Preclinical In Vivo Studies of Ureidomustine (BO-1055)

i) Non-GLP Acute 14-day Toxicity of Ureidomustine Following Intravenous Injection in ICR Mice.

The inventors have studied the acute intravenous injection 14-day toxicity of ureidomustine in ICR mice to determine the maximum tolerated dose (MTD) in tumor xenografted mice and optimize the drug treatment conditions (e.g. dosage and schedule). ureidomustine at different doses (50, 60, 70, 80, and 100 mg/kg in double distilled water) and a vehicle control group, were administrated to six ICR mice per group. The mice were observed for 14 days and mortality and body weight were recorded and the median lethal dose ($LD_{50}$) of ureidomustine was determined (Table 9). Acute mortality was first seen at 70 mg/k (1/6 mice)<1 hr after drug administered and at 80 mg/kg all mice died in <1 hr. The $LD_{50}$ of BO-1055 in these normal mice was 70 mg/kg.

TABLE 9

The acute intravenous injection 14-day toxicity of ureidomustine in normal ICR mice

| Dose mg/kg | Post dosing deaths at >1 hr | 1-4 hrs | SD2-5 | SD6 | SD7 | SD8 | SD9 | SD 10 | SD 11 | SD1 2-14 | Mortality (N/N)a | LD$_{50}$ mg/kg |
|---|---|---|---|---|---|---|---|---|---|---|---|---|
| 0b | 0 | 0 | 0000 | 0 | 0 | 0 | 0 | 0 | 0 | 0 | 0/6 | |
| 50 | 0 | 0 | 0000 | 0 | 0 | 0 | 0 | 0 | 0 | 0 | 0/6 | |
| 60 | 0 | 0 | 0000 | 0 | 0 | 0 | 0 | 0 | 0 | 0 | 0/6 | |
| 70 | 1 | 0 | 0000 | 0 | 0 | 0 | 0 | 0 | 0 | 0 | 1/6 | 70 |
| 80 | 6 | 0 | 0000 | 0 | 0 | 0 | 0 | 0 | 0 | 0 | 6/6 | |
| 100 | 6 | 0 | 0000 | 0 | 0 | 0 | 0 | 0 | 0 | 0 | 6/6 | | aN/N: Number of mice found dead/Number of mice observed. Post dosing (hrs) column shows the number of deaths that occurred within the 1st hr after drug injection or in the subsequent 3 hrs. SD = study day number after the injection of BO-1055.
bLD50: Median Lethal Dose. The LD$_{50}$ is calculated as 70 mg/kg with 95% confidence interval of 58.8~107.2 mg/kg. The formula is Log dose = 1.73 + 0.0233 probit K.
cVehicle: dd water ii) Studies on hERG Inhibition and Early ADME Studies of Ureidomustine.

The inventors examined the cardiac safety of ureidomustine using the hERG FP assay [Deacon et al. 2007]. The human ether-a-go-go related gene (hERG) encodes the inward rectifying voltage gated potassium channel in the heart (IKr) that is involved in cardiac repolarization. Inhibition of the hERG current causes QT interval prolongation resulting in potentially fatal ventricular tachyarrhythmia. A number of drugs have been withdrawn from late stage clinical trials due to these cardio toxic effects; therefore, it is important to identify inhibitors early in drug discovery.

hERK inhibition was studied using the hERG Fluorescence Polarization Assay to measure the binding of ureidomustine to the hERG receptor. The assay is based upon the ability of the test compound in displaying a fluorescent tracer from hERK receptor (Predictor™ hERG membrane) that produces a change in optical signal. The assay was performed in a black 383-well assay plate by determining the dose-response binding curve from the competitive binding of the test compound with fluorescent tracer. The IC$_{50}$ of hERG-specific binding by ureidomustine was 12.6±1.64 µM (n=3) versus astemizole (IC$_{50}$ 0.007 µM), indicating weak or no inhibition and little likelihood of cardiac arrhythmic side effects. The concentration-response curves for ureidomustine are shown in FIG. 6.

Figure 6:
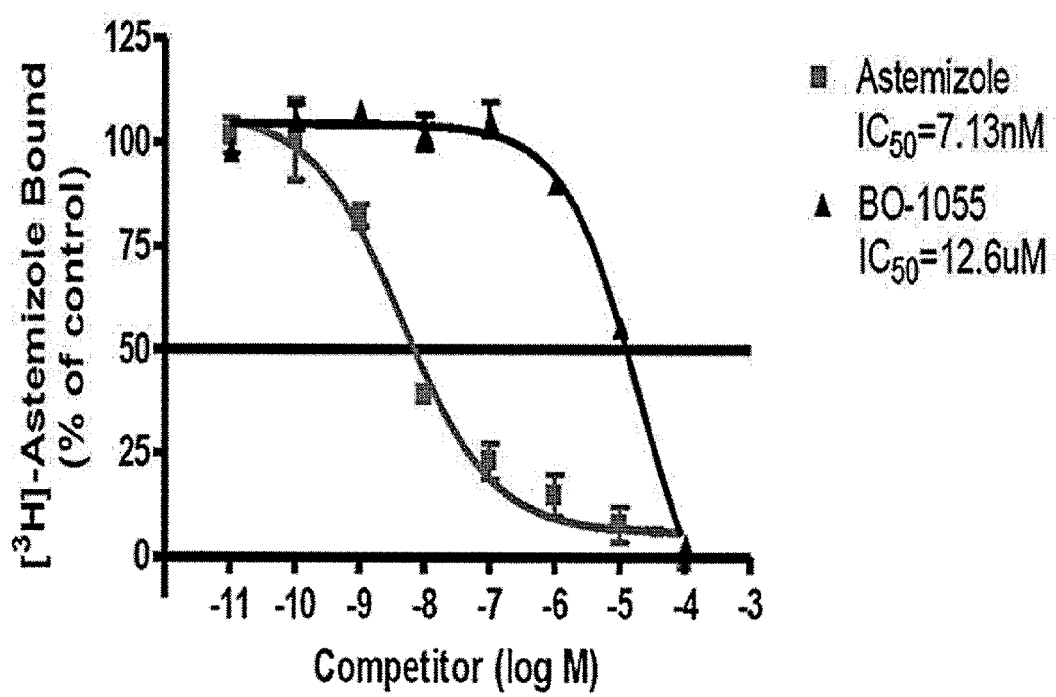
FIG. 6 shows a graphical representation of the hERG Fluorescence Polarization Assay of binding of ureidomustine to the hERG receptor.

FIG. 6 shows the results of evaluation of BO-1055 cardiotoxicity by hERG inhibition evaluation. Based on binding inhibition by BO-1055 (IC$_{50}$ 12.6 µM) compared to doxorubicin (IC$_{50}$ 0.03±0.03), a drug with well-known cardiotoxicity dose limiting toxicity, it was determined to be unlikely that the BO-1055 would exhibit cardiac arrhythmic side effects.

Example 10

Studies on the Caco-2 Permeability and P-Glycoprotein (P-Gp) Mediated Efflux in Caco-2 Cell Monolayers by Ureidomustine (Table 8).
(i) P-Glycoprotein (P-Gp) Mediated Efflux in Caco-2 Cell Monolayers:

P-glycoprotein (P-gp, Permeability glycoprotein) is a very well investigated efflux pump of the Multi Drug Resistant genes (MDR) subfamily. P-gp is energy dependent transporter protein involved in effluxing a number of drugs and impedes their absorption intracellularly. Permeability across Caco-2 cell monolayers is used to predict human permeability of drug candidates, to perform in-depth mechanistic and absorption studies and to study the effects of transporters on permeability and transporter-mediated drug-drug interactions.

The Caco-2 permeability assay is considered to be the industry gold standard for in vitro prediction of in vivo human intestinal permeability and bioavailability of orally administered drugs. The Caco-2 permeability assay uses an established method for predicting the absorption of therapeutic compounds across the GIT by measuring the rate of transport across a contiguous Caco-2 cell monolayer. Measuring transport apical to basolateral (A→B) and basolateral to apical (B→A) across the cell monolayer enables calculation of an efflux ratio and determines if a compound undergoes active efflux. The Caco-2 assay measures the passage of a test compound from a donor chamber into an acceptor chamber through a porous membrane on which a confluent Caco-2 monolayer forms a cellular barrier.

The results of Caco-2 permeability assay showed that the Papp coefficient of BO-1055 in A→B direction was not detected. The Papp coefficient in the B→A direction was 7.05×10−6 cm/sec. The mass balance of BO-1055 in A→B and B→A directions was <50%. A mass balance of >80% gives an acceptable approximation of the Papp. A significant fraction of BO-1055 disappeared during the transport experiment, a poor mass balance resulted and the Papp obtained became unreliable.

The result of this study is that ureidomustine is considered to be a very low permeable drug, indicating that this agent has poor oral absorption. In addition, the study on the P-gp mediated efflux in Caco-2 cell monolayers of ureidomustine showed that the P-gp efflux ratio (B→A/A→B) is >>2, indicating that this agent does not inhibit P-gp. The studies suggest that ureidomustine is not suitable for oral administration.

(ii) Microsome Stability

Drug metabolism or xenobiotic biotransformation plays an important role in drug discovery since it affects clearance, half-life and oral bioavailability. Liver is the principal organ involved in metabolism of xenobiotics. Liver microsomes are subcellular fractions comprising predominantly of endoplasmic reticulum containing cytochrome P450 enzymes, flavin-monooxygenases, carboxylesterases and epoxide hydrolase and hence provide a useful model of Phase I metabolism. Phase I reactions comprise oxidation, reduction and/or hydrolysis and require NADPH as a cofactor. Thus, incubation of potential drug candidates with liver microsomes can provide a measure of their inherent metabolic vulnerability towards these enzymes.

The metabolic stability of BO-1055 in rat liver microsomes (RLMs) was studied with 7-Ethoxycoumarin (7-EC) as a positive control. The results are shown in Table 10. Table 10 demonstrates that the apparent half-lives of BO-1055 and 7-EC in RLM were 29.7 and 23.5 min, respectively. BO-1055 was more stable than 7-EC in the pooled RLMs.

TABLE 10

Summary of metabolic stability parameters of BO-1055 and 7-ethoxycoumarin incubated in rat liver microsomes for 60 min.

| Compound | MR (nmol/min/mg) | $t^{1/2}$ (min) | % Remaining at 60 min | Matrix |
|---|---|---|---|---|
| BO-1055 | 0.0203 | 29.7 | 25 | RLM[2] |
| 7-EC[1] | 0.0448 | 23.5 | 18 | RLM |

MR: Metabolic Rate (MR (nmol/min/mg protein) = λ * C0/Cprotein)
[1]7-EC: 7-Ethoxycoumarin.
[2]RLM: Pooled rat liver microsomes.

Example 11

Plasma Stability and Protein Binding of BO-1055 (Ureidomustine)

In drug discovery, the information on drug-plasma protein binding is valuable in evaluating and understanding, the absorption, distribution, metabolism and excretion (ADME)-related properties and the pharmacokinetic profile of drug candidates. The binding of BO-1055 to plasma proteins of rat was studied by spiking BO-1055 (20 µM) into rat plasma and dialyzing against buffer until equilibrium was achieved. Concentrations of the BO-1055 in plasma and buffer were determined to calculate percentages of the drug that were unbound or bound to plasma proteins.

Figure 7:
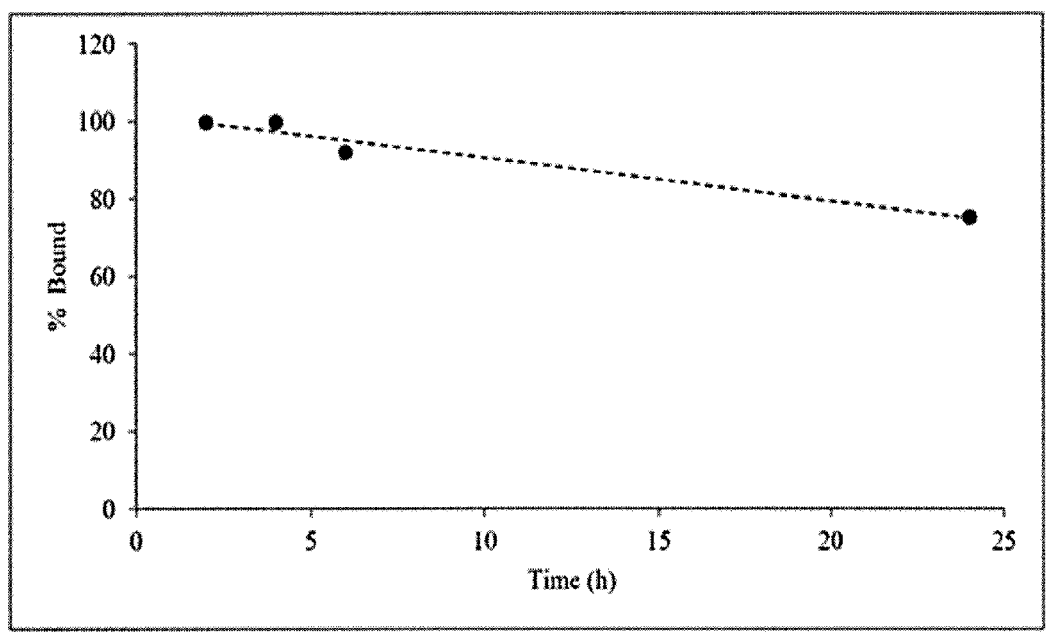
FIG. 7 shows a plot of ureidomustine bound to plasma proteins vs time.

The results are shown in FIG. 7 and Table 11. The mean bound values were 99.68, 99.69, 92.01, and 75.17% for incubation times of 2, 4, 6, and 24 h, respectively at a nominal spiked concentration of 20 µM (FIG. 7 and Table 11). FIG. 7 shows a time course to reach equilibrium of BO-1055 binding to rat plasma proteins using a multi-equilibrium dialysis method.

TABLE 11

Mean fractional binding determination of BO-1055 in rat plasma

| Incubation time (h) | % bound | CV (%) |
|---|---|---|
| 2 | 99.68 | 0.01 |
| 4 | 99.69 | 0.04 |
| 6 | 92.01 | 0.66 |
| 24 | 75.17 | 3.87 |

Example 12

BO-1055 (Ureidomustine) has a Broad Spectrum of Antitumor Activity.

The cytotoxicity of ureidomustine to variety of human solid tumor, sarcoma, leukemia, and lymphoma cell lines was examined. As shown in Table 12, the $IC_{50}$ values of ureidomustine against the tested cell lines were in sub-µM range in 30%. Whereas in a panel of 29 benign cell types none had $IC_{50}$ values of <5.00 µM and 27% had $IC_{50}$ values of >20->100 µM.

TABLE 12

Panel of Human Cancer Cell lines, Primary Patient Tumor Samples and multiple types of normal tissues used for cytotoxicity evaluation. Total number of lines of each cancer type/subtype and number separate columns showing number of lines per group sensitive to BO-1055 cytotoxicity ($IC_{50}$ < 1.00 µM) or with intermediate sensitivity ($IC_{50}$ 1.00-4.99 µM), low resistance ($IC_{50}$ 5.00-9.99 µM) and high resistance ($IC_{50}$ ≥10.0 µM).

| Cancer Cell Lines Cancer types/subtypes | Total Lines No. | $IC_{50}$ µM <1.00 Sensitive | $IC_{50}$ µM 1.00-4.99 Intermed | $IC_{50}$ µM 5.00-9.99 Low rest. | $IC_{50}$ µM ≥10.0 Resistant |
|---|---|---|---|---|---|
| Breast Cancer | 10 | 3 | 1 | 0 | 6 |
| Colorectal cancer | 4 | 1 | 0 | 0 | 3 |
| Glioblastoma | 4 | 0 | 1 | 2 | 1 |
| AML Transformed CB, BM | 6 | 5 | 1 | 0 | 0 |
| Leukemia AML | 9 | 3 | 3 | 1 | 2 |
| Leukemia AML JAK2-V617 | 4 | 0 | 0 | 0 | 4 |
| Leukemia T-ALL, B-ALL, Non-T/B | 5 | 4 | 1 | 0 | 0 |
| Myeloma | 9 | 1 | 2 | 1 | 5 |
| Ovarian cancer | 11 | 0 | 3 | 0 | 8 |
| Leukemia Primary | 9 | 5 | 1 | 3 | 0 |
| Lymphoma B-Cell DLBCL (GCB) | 11 | 4 | 7 | 0 | 0 |
| Lymphoma B-Cell DLBCL (ABC) | 4 | 1 | 3 | 0 | 0 |
| Lymphoma Mantle Cell | 7 | 4 | 2 | 0 | 1 |
| Lymphoma B cell (Murine) | 2 | 2 | 0 | 0 | 0 |
| Prostate Cancer | 3 | 0 | 2 | 0 | 1 |
| Renal Cancer | 3 | 0 | 1 | 1 | 1 |
| Sarcoma, Ewing's | 8 | 7 | 1 | 0 | 0 |
| Sarcoma, Desmoplastic SRCT | 2 | 0 | 2 | 0 | 0 |
| Sarcoma, Osteosarcoma | 4 | 0 | 1 | 0 | 3 |
| Sarcoma, Rhabdomyosarcoma | 4 | 3 | 0 | 0 | 1 |

TABLE 12-continued

Panel of Human Cancer Cell lines, Primary Patient Tumor Samples and multiple types of normal tissues used for cytotoxicity evaluation. Total number of lines of each cancer type/subtype and number separate columns showing number of lines per group sensitive to BO-1055 cytotoxicity ($IC_{50}$ < 1.00 µM) or with intermediate sensitivity ($IC_{50}$ 1.00-4.99 µM), low resistance ($IC_{50}$ 5.00-9.99 µM) and high resistance ($IC_{50}$ ≥10.0 µM).

| Cancer Cell Lines Cancer types/subtypes | Total Lines No. | $IC_{50}$ µM <1.00 Sensitive | $IC_{50}$ µM 1.00-4.99 Intermed | $IC_{50}$ µM 5.00-9.99 Low rest. | $IC_{50}$ µM ≥10.0 Resistant |
|---|---|---|---|---|---|
| Sarcoma, Synovial | 1 | 1 | 0 | 0 | 0 |
| Lung Cancer NSCLC | 28 | 2 | 8 | 1 | 17 |
| Lung Adenosquamous + Squamous | 12 | 1 | 3 | 3 | 5 |
| Lung Cancer Large Cell | 4 | 0 | 1 | 1 | 2 |
| Lung Cancer Small Cell | 10 | 5 | 1 | 0 | 4 |
| Total No. Cancer Cell Lines | 174 | 52 | 44 | 14 | 63 |
| Normal tissue Multiple Types | 25 | 0 | 0 | 4 | 21 |
| Total No. lines normal + tumor | 199 | 52 | 44 | 18 | 84 |

Example 13

BO-1055 Cytotoxicity ($IC_{50}$ µM) Against Human Cancer Cell Lines and Primary Human Tumor Samples In Vitro and In Vivo in Xenograft Models.

The cytotoxicity of BO-1055 was evaluated against panels of human cancer cell lines in vitro. Comparisons were made with other therapeutic alkylating agents and conventional chemotherapeutic agents. Where in vivo studies were undertaken, data is presented on tumor growth kinetics with and without BO-1055 treatment using xenograft models in Nude or NSG mice.

Data are presented in alphabetic order based on tumor type and subtypes.

Example 13A

Leukemia

It is estimated that in 2012 there were 352,000 cases of leukemia of all types world-wide and 265,000 deaths, with incidence and mortality rates varying across the world.

i) Subtypes of Leukemia:

Leukemia can be subdivided into acute myeloid leukemia (AML), acute lymphoid or lymphoblastic leukemia (ALL, T-cell or B-cell subtypes), bi-phenotypic leukemia, chronic lymphocytic leukemia (CLL, T-cell or B-cell subtypes) and chronic myeloid leukemia (CML). The latter has both a chronic phase and acute phase blastic crisis. Chronic myelomonocytic leukemia (CMML) is another variant form presenting as a myelodysplastic syndrome characterized by abnormal clonal myeloid proliferation and by progression to acute myelogenous leukemia (AML). A sub group of CMML is characterized by a t(5;12)(q33;p13) balanced chromosomal translocation that fuses PDGFRβ to an ets-like gene tel (Golub et al 1994). The FAB classification based on morphology recognizes 8 leukemia subgroups, but more recent sub-classifications are based on molecular features.

The development of effective treatment strategies for most forms of acute myeloid leukemia (AML) has languished for the past several decades. There are a number of reasons for this, including the considerable heterogeneity of this disease and paucity of molecular markers that can be used to predict clinical outcomes and responsiveness to different therapies.

The inventors have evaluated the cytotoxicity of ureidomustine against the human T-cell leukemia line CCRF-CEM, a subline, CCRF-CEM/Taxol that is 330-fold resistant to taxol, and a subline CCRF-CEM/VBL that is 680-fold resistant to vinblastine. As shown in Table 13, BO-1055 has only a 9.4- or 6.2-fold reduced cytotoxicity to CCRF-CEM/Taxol and CCRF-CEM/VBL, respectively, in comparison with the corresponding $IC_{50}$ of the parent CCRF-CEM cell line, indicating that this agent is not significantly cross-resistance to either Taxol or Vinblastine. This data also supports other evidence showing that that BO-1055 is not a good substrate for the membrane multidrug resistance transporters (i.e., p-glycoprotein) nor does it interact with mutated tubulin.

TABLE 13

Ureidomustine (BO-1055) toxicity to the human T-cell leukemia cell line CCRF-CM and on Paclitaxel-resistant (CCRF-CEM/Taxol) or vinblastine-resistant (CCRF-CEM/VBL) sublines ($IC_{50}$ µM)

| Compound. | CCRF-CEM (µM) | CCRF-CEM/Taxol a (µM) | CCRF-CEM/VBL b (µM) |
|---|---|---|---|
| ureidomustine | 0.13 ± 0.002 | 1.22 ± 0.02 [9.4x] c | 0.80 ± 0.01 [6.2x] | a CCRF-CEM/Tax is 330-times more resistant to the parental cell lines CCRF-CEM;
b CCRF-CEM/BVL is 980-times more resistant to the parental cell lines CCRF-CEM;
c Numbers in the brackets are fold of cross-resistant determined by comparison with the corresponding $IC_{50}$ of the parent cell line.

ii) Development of MLL-AF9-Immortalized Human Hematopoietic Cells Lines

Chromosomal rearrangements of the MLL gene are associated with high-risk infant, pediatric, adult, and therapy-induced acute leukemias. So far, about 80 different direct MLL fusions and about 120 reciprocal MLL fusions have been characterized at the molecular level. The MLL-AF9 fusion gene originates from the translocation t(9;11)(p22;q23) and is associated with aggressive leukemias of both the myeloid and lymphoid lineage in infants, whereas in adults, this translocation is mainly associated with acute myeloid leukemia. Depending on extrinsic cues, human neonatal CD34+ cells are readily immortalized along either the myeloid or lymphoid lineage upon MLL-AF9 expression and give rise to mainly lymphoid leukemia in immunocompromised mice. In contrast, immortalization of adult bone marrow CD34+ cells is more difficult to achieve and is myeloid-biased, even when MLL-AF9 is expressed in purified hematopoietic stem cells (HSCs) (Horton et al. 2013). Transcriptome analysis identified enrichment of HSC but not progenitor gene signatures in MLL-AF9-expressing cells.

Although not observed in adult cells, neonatal cells expressing MLL-AF9 were enriched for gene signatures associated with poor prognosis, resistance to chemotherapeutic agents and MYC signaling. These results indicate that neonatal cells are inherently more prone to MLL-AF9-mediated immortalization than adult cells (Horton et al. 2013). Mulloy and associates (Wei et al 2008) have shown that expression of MLL-AF9 in human CD34+ cells induces acute myeloid, lymphoid, or mixed-lineage leukemia in immuno-deficient mice. Some leukemia stem cells (LSC) were multipotent and could be lineage directed by altering either the growth factors or the recipient strain of mouse, highlighting the importance of micro-environmental cues. Other LSC were strictly lineage committed, demonstrating the heterogeneity of the stem cell compartment in MLL disease.

Targeting the Rac signaling pathway by pharmacologic or genetic means resulted in rapid and specific apoptosis of MLL-AF9 cells, suggesting that the Rac signaling pathway may be a valid therapeutic target in MLL-rearranged AML. As expected for immortal cells, all of the cell lines we have tested are telomerase positive.

Whether the MLL-AF9 proteins are activating hTERT expression/activity themselves or are promoting the growth of a cell that normally expresses hTERT remains to be determined. MLL t(9;11) is believed to be prognostically favorable in AML-M5 compared to other genetic alterations involving MLL. MLL is a histone methyltransferase deemed a positive global regulator of gene transcription. This protein belongs to the group of histone-modifying enzymes comprising transactivation domain 9aaTAD and is involved in the epigenetic maintenance of transcriptional memory.

iii) MLL-AF9 Cell Lines Used for Evaluation of BO-1055 Cytotoxicity
   a) Growth factor-dependent & cell density growth dependent cell lines. Human cord blood CD34+ cells transduced with MLL-AF9 gene: MA-10, MA-18. Human bone marrow CD34+ cells transduced with MLL-AF9 gene: MA-23. Human cord blood CD34+ cells transduced with MLL-AF9 and N-ras genes: MA-9.3, MA-9.6.
   b) Growth factor independent leukemic cell lines. Human MA-10 cells transduced with Flt3 ITD (W51) were adapted to in vitro proliferation without growth factors (Moore Laboratory). Human AML cell lines THP-1 (MLL-AF9); MOLM-13 (MLL-AF9 & Flt3 ITD); Kasumi (AML1-ETO); MV4;11 (MLL-AF4 & Flt3 ITD); Set2 (Jak2 V617); HEL (Jak2 V617).

iv) BO-1055 is Highly Cytotoxic to Acute Myeloid Leukemic Cell Lines, but not to Leukemic Cell Lines with Mutated JAK2T.

Figure 8:
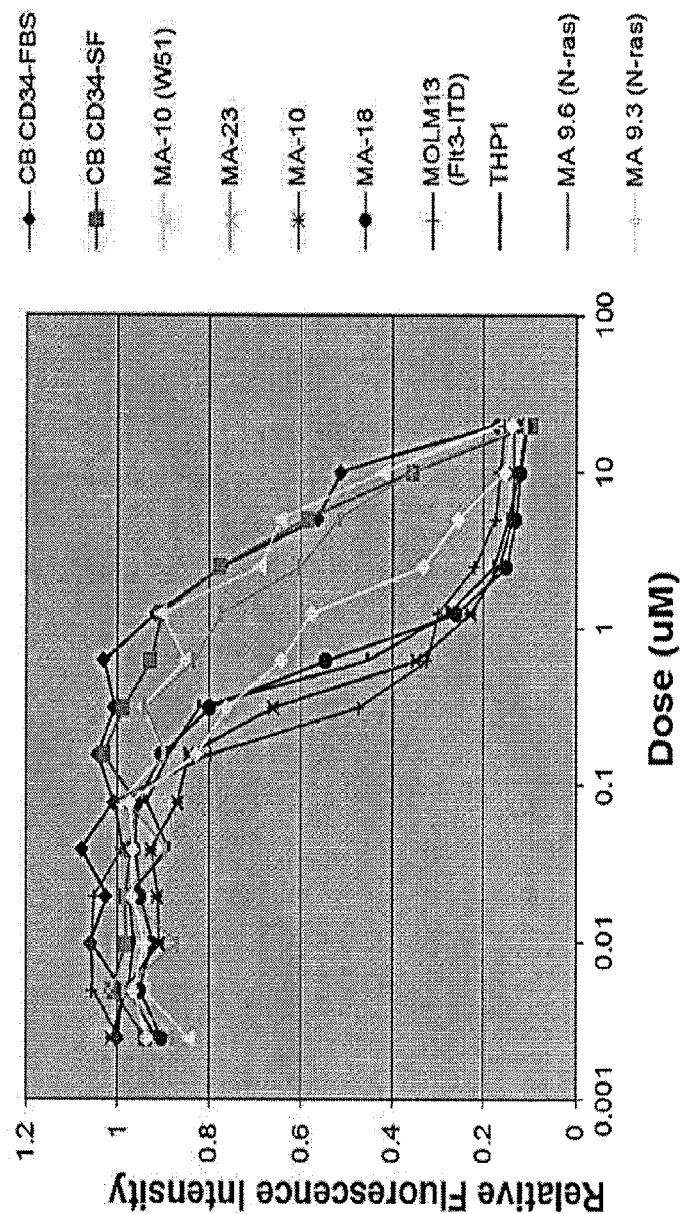
FIG. 8 shows alamar blue fluorescence intensity dose-response curves of BO-1055 cytotoxicity at 72 hrs against various leukemic cell lines and normal cord blood CD34+ HSC/HPC.

As shown in Table 14 and FIG. 8, BO-1055 was highly cytotoxic to 3/7AML cell lines ($IC_{50}$ 0.18-0.45 µM), moderately cytotoxic to one ($IC_{50}$ 1.50 µM), with two JAK2 V617 mutant lines highly resistant ($IC_{50} \geq 10$ µM) and one AML-ETO AML line highly resistant ($IC_{50}$ 80.0 µM). The cell lines developed by transduction of MLL-AF9 into normal CB CD34+ cells (MA10, MA18) or adult BM CD34+ cells (MA23), were uniformly highly sensitive to BO-1055 ($IC_{50}$ 0.25-0.40 uM (FIG. 8). The normal CB CD34+ cells transduced with two oncogenes were also highly sensitive to BO-1055, either MLL-AF9+Flt3ITD transduced ($IC_{50}$ 0.40 uM) or MLL-AF9+N-RASmut ($IC_{50}$ 0.81-2.91 uM). When compared to the cytotoxicity against normal CB CD34+($IC_{50}$ 9.9-10.2 uM) it can be concluded that the introduction of the MLL-AF9 oncogenic fusion genes into a normal CB or BM CD34+ cell increases BO-1055 cytotoxicity 25-40-fold. The addition of a second oncogene (Flt3ITD or N-Ras) did not further enhance sensitivity to BO-1055 over that observed with MLL-AF9 only.

v) BO-1055 is Highly Cytotoxic to Acute Myeloid Leukemia Stem Cells in Some Molecular Subtypes but not in Others.

BO-1055 cytotoxicity to leukemic stem cells (LSC) was determined using six primary pediatric AML samples of different molecular subtypes. The assay for LSC was undertaken using the MS5 co-culture assay with measurement of week 2 cobblestone area-forming cells ((Schuringa et al 2004, Chung et al 2005, Moore et al 2007). As shown in Table 14, LSCs from three patient samples were very sensitive to BO-1055 ($IC_{50}$ 0.12-0.90 µM). These examples are poor prognosis molecular subtypes (Monosomy 7, MLL-AF9 and Flt3ITD) indicating that BO-1055 may be an effective therapy in this group of AML that otherwise have a very poor prognosis. The patients with del17 and good prognosis NPM1 mutation and Inversion 16 were more sensitive to BO-1055 ($IC_{50}$ 6.25-7.0 µM) than normal HSCs but the therapeutic window was narrow

TABLE 14

$IC_{50}$ (µM) of BO-1055, Temozolomide (TZM) and Melphalan on a panel of 27 leukemia cell lines including AML, T-ALL and primary patient samples of AML of different molecular subtypes and HSC transformed with MLL-AF9 ± NRAS or Flt3ITD.

| Leukemia Acute Myeloid (mutations, translocations) | BO-1055 | TMZ | Melph |
|---|---|---|---|
| HL-60 CDKN2A, NRAS, p53 del. | 1.50 | 49.0 | 0.17 |
| Kasumi-1 AML-ETO | 80.0 | 389.0 | 0.004 |
| MOLM13 MLL-AF9 | 0.18 | | |
| MV4; 11 MLL-AF4 + Flt3ITD | 0.30 | | |
| THP-1 MLL-MLLT3, CDKN2A/B del, PTEN del. | 0.45 | | |
| AML JAK2-V617 mut | | | |
| HEL | ≥10.0 | | |
| SET2 | ≥10.0 | | |
| Leukemia AML HSC-derived | | | |
| AML 9.3 MLL-AF9 + NRAS | 0.81 | | |
| AML 9.6 MLL-AF9 + NRAS | 2.91 | | |
| MA-10 CB + MLL-AF9 | 0.35 | | |
| MA-10-W51 CB MLL-AF9 + Flt3ITD | 0.40 | | |
| MA-18 CB + MLL-AF9 | 0.40 | | |
| MA-23 BM + MLL-AF9 | 0.25 | | |
| AML Patients LSC | | | |
| AML-1 Monosomy 7 | <0.20 | | |
| AML-2 MLL-AF9 | 0.12 | | 7.00 |
| AML-3 Flt3ITD | 0.90 | | |
| AML-4 t-AML, del17(p) | 7.50 | | |
| AML-5 NPM1 | 7.50 | | |
| AML-6 Inversion 16 | 6.25 | | |
| Leukemia T-ALL | | | |
| CCRF-CEM | 0.68 | 424.0 | 0.001 |
| CCRF-CEM/VBL | 0.80 | | |
| CCRF-CEM/Taxol | 1.22 | 502.0 | |
| COG-LL-317 | | 181.0 | 0.001 |
| JURKAT | 2.50 | 2.07 | 0.25 |
| MOLT-4 | | 181.5. | 0.001 |
| Patient Samples B-ALL, T-ALL | | | |
| Human B-ALL | 1.05 | | 30.0 |
| Human T-ALL | 1.00 | | |

(vi) Dose-Response Analysis of BO-1055 Cytotoxicity Comparing Normal CB CD34+ Cells to AML and A.Mon.L Cell Lines and Oncogene-Transduced CD34+ Cells.

As shown in FIG. 8 and Table 14, normal hematopoietic progenitor cells (CB CD34+FBS or SF) were resistant to BO-1055 ($IC_{50}$ 9.9-10.2 µM). In contrast, the A. Mon. L cell lines THP1 and MOLM13 were highly sensitive ($IC_{50}$ 0.18-0.45 µM). The CB-derived MLL-AF9 transduced lines MA-10 and MA-18 and the BM-derived MLL-AF9 transduced line MA-23 were highly sensitive to BO-1055 cytotoxicity ($IC_{50}$ 0.25-0.40 µM). The MA10 W51 cell line (CB MLL-AF9+Flt3ITD) was maintained as growth factor independent and growth factor (hGM-CSF or hIL-3) dependent sub-lines. The former was more resistant to BO-1055 cytotoxicity ($IC_{50}$~10 µM) than the latter ($IC_{50}$ 0.28-0.40 µM). The MA-9.3 and MA-9.6 CB MLL-AF9+NRAS lines diverged in sensitivity to BO1055 with the former being highly sensitive ($IC_{50}$ 0.81 µM) and the latter less sensitivity ($IC_{50}$ 2.91 µM).

Figure 9:
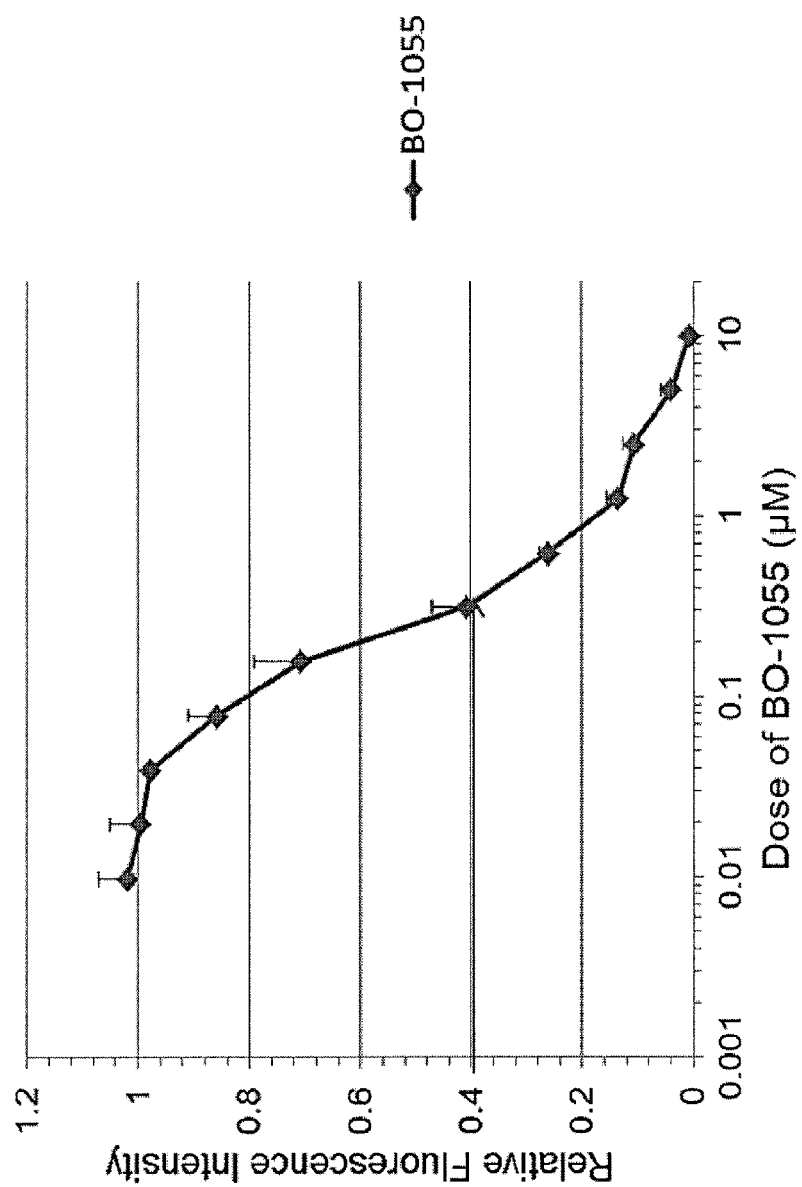
FIG. 9 shows a plot of dose of ureidomustine vs relative fluorescent intensity of growth factor dependent MA-10-W51 cells.

FIG. 9 shows effect of BO-1055 on the proliferation of growth factor dependent MA-10-W51 cells (normal CD34+ transduced with MLL-AF9 fusion gene and mutated Flt3ITD). A dose titration comparison of BO-1055 and BO-1978 on growth factor dependent MA-10-W51 cells shows that both compounds were highly cytotoxic, with BO-1978 more so than BO-1055.

(vii) "Therapeutic Window" of BO-1055, Four Alkylating Drugs, a Microtubule Binding Drug, Topoisomerase Inhibitors, an HSP90 Inhibitor and an Anthracycline Antitumor Antibiotic, Determined by Comparison of $IC_{50}$ Against 5 Normal Human Tissues and Three Malignant Leukemias-an AML Cell Line, a Primary AML and a Primary B-ALL.

The therapeutic window obtained with BO-1055 on the MV4; 11 AML cell line and primary pediatric AML-2 and B-ALL cells emphasizes BO-10555 lack of toxicity on normal bronchial epithelium (Bci-NSI), Fallopian tube epithelium (FTEC), endothelium (HUVEC), bone marrow mesenchymal stroma (huMSC), and normal cord blood hematopoietic progenitor cells (CD34+ cells, CFC). This contrasted with the high cytotoxicity of BO-1055 against the leukemias (Table 15). Of note is the lack of a therapeutic window with the alkylating drugs 4-HC (active metabolite of cyclophosphamide), bendamustine, cisplatin, topoisomerase inhibitors etoposide and SN38, the HSP90 inhibitor PU-H71, an anthracycline antitumor antibiotic (doxorubicin) and a microtubule binding alkaloid (vincristine), due primarily to their toxicity to normal CFC.

TABLE 15

Therapeutic window determinations of BO-1055, alkylating drugs and other chemotherapeutic drugs, comparing their toxicity ($IC_{50}$ µM) against five normal human tissue types to toxicity against an AML cell line (MV4; 11), a primary AML (AML-2) and a primary B-ALL.

| 1. Chemical | CD34+ | HUVEC | huMSC | NSI | FTEC | MV4; 11 |
|---|---|---|---|---|---|---|
| BO-1055 | 50.00 | 166.67 | 66.67 | 133.33 | 266.67 | 1.00 |
| 4-HC | 1.34 | 27.00 | 27.00 | 12.00 | 8.33 | 1.00 |
| Benamustine | 0.17 | 2.50 | 5.00 | 2.50 | 6.67 | 1.00 |
| Melphalan | 7.00 | 320.00 | 160.00 | ND | ND | ND |
| Cisplatin | 0.75 | 6.25 | 2.50 | 3.75 | 12.50 | 1.00 |
| Doxorubicin | 10.53 | 18.42 | 23.68 | 26.32 | 328.95 | 1.00 |
| Etoposide | 0.23 | 0.90 | 180.00 | 1.28 | 512.82 | 1.00 |
| PUH71 | 1.00 | 7.78 | 14.00 | 33.33 | 1777.8 | 1.00 |
| SN-38 | 1.17 | 66.67 | 33.33 | 83.33 | 333.33 | 1.00 |
| Vincristine | 5.20 | 0.56 | 14.00 | 444.44 | 555.56 | 1.00 |

TABLE 15-continued

Therapeutic window determinations of BO-1055, alkylating drugs and other chemotherapeutic drugs, comparing their toxicity ($IC_{50}$ µM) against five normal human tissue types to toxicity against an AML cell line (MV4; 11), a primary AML (AML-2) and a primary B-ALL.

| 2. Chemical | CD34+ | HUVEC | huMSC | Bci- | FTEC | AML-2 |
|---|---|---|---|---|---|---|
| BO-1055 | 48.00 | 160.00 | 64.00 | 128.00 | 256.00 | 1.00 |
| 4-HC | 0.64 | 12.96 | 12.96 | 5.76 | 4.00 | 1.00 |
| Benamustine | 0.50 | 7.50 | 15.00 | 7.50 | 20.00 | 1.00 |
| Melphalan | 1.00 | 45.71 | 22.86 | ND | 45.71 | 1.00 |
| Cisplatin | 0.10 | 0.83 | 0.33 | 0.50 | 1.67 | 1.00 |
| Doxorubicin | 1.03 | 1.79 | 2.31 | 2.56 | 32.05 | 1.00 |
| Etoposide | 0.94 | 3.68 | 738.95 | 5.26 | 2105.3 | 1.00 |
| PUH71 | 0.50 | 3.89 | 7.00 | 16.67 | 888.89 | 1.00 |
| SN-38 | 7.00 | 400.00 | 200.00 | 500.00 | 2000.0 | 1.00 |
| Vincristine | 2.60 | 0.28 | 7.00 | 222.22 | 277.78 | 1.00 |

| 3. Chemical | CD34+ | HUVEC | huMSC | Bci- | FTEC | B-ALL |
|---|---|---|---|---|---|---|
| BO-1055 | 12.00 | 40.00 | 16.00 | 32.00 | 64.00 | 1.00 |
| 4-HC | 0.40 | 8.10 | 8.10 | 3.60 | 333.33 | 1.00 |
| Benamustine | 0.13 | 1.88 | 3.75 | 1.88 | 555.56 | 1.00 |
| Melphalan | 0.23 | 10.67 | 5.33 | ND | 1.67 | 1.00 |
| Cisplatin | 0.10 | 0.83 | 0.33 | 0.50 | 20.00 | 1.00 |
| Doxorubicin | 1.03 | 1.79 | 2.31 | 2.56 | 256.00 | 1.00 |
| Etoposide | 0.94 | 3.68 | 738.95 | 5.26 | 160.00 | 1.00 |
| PUH71 | 0.29 | 2.24 | 4.04 | 9.62 | 32.05 | 1.00 |
| SN-38 | 0.78 | 44.44 | 22.22 | 55.56 | 2105.3 | 1.00 |
| Vincristine | 0.16 | 0.02 | 0.42 | 13.33 | 45.71 | 1.00 |

(viii) Determination of Tumor-initiating Cell Frequency in Xenografts of THP-1 Monocytic Leukemia with and without Exogenous hGM-CSF Administration.

In order to determine the number of leukemic cells needed to ensure engraftment, NSG mice were injected i.v. with from $1\times10^3$-$3\times10^6$ GFP-Luciferase transduced THP-1 AML cells into eight NSG mice.

Figure 10:
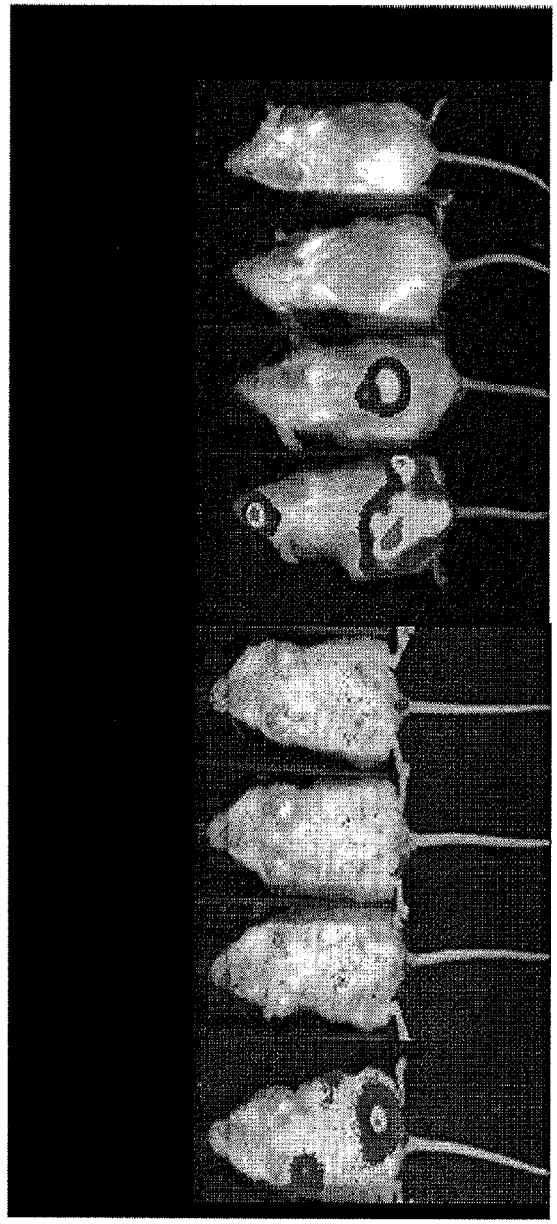
FIG. 10A shows a bioimaging photograph panel of four mice injected with $1 \times 10^3$-$3 \times 10^6$ GFP-Luciferase transduced THP-1 AML cells and not further treated.
FIG. 10B shows a bioimaging photograph panel of four mice injected with $1 \times 10^3$-$1 \times 10^6$ GFP-Luciferase transduced THP-1 AML cells and also implanted subcutaneously with an osmotic minipump at the time of tumor injection that released 1 ug of human GM-CSF per day over 40 days.

Four engrafted mice were not further treated (FIG. 10A) and four were implanted s.c. with an osmotic minipump (Alzet) at the time of tumor injection that released 1 µg of human GM-CSF per day over 40 days (FIG. 10B). Mice in both groups were bioimaged at 7 weeks.

As shown in FIGS. 10A and 10B, in the absence of exogenous human GM-CSF engraftment was only detected with the highest dose of THP-1 cells ($3\times10^6$). Increased engraftment was evident in mice treated with hGM-CSF with both $1\times10^6$ and $1\times10^5$-30-fold increase in detection of tumor-initiating cells in this cell line.

(ix) BO-1055 Treatment of NSG Mice Transplanted with the Human MLL-AF9-Translocated AML Cell Line MV4;11.

MSG mice were transplanted with $10^5$ MV4;11-GFP/Luciferase transduced cells injected i.v. into each of ten male 12 wk-old NSG mice. The cytotoxicity of BO-1055 (30 mg/kg every second day beginning on d14 x5) was determined in 5 NSG mice with 5 control mice receiving media alone.

Figure 11:
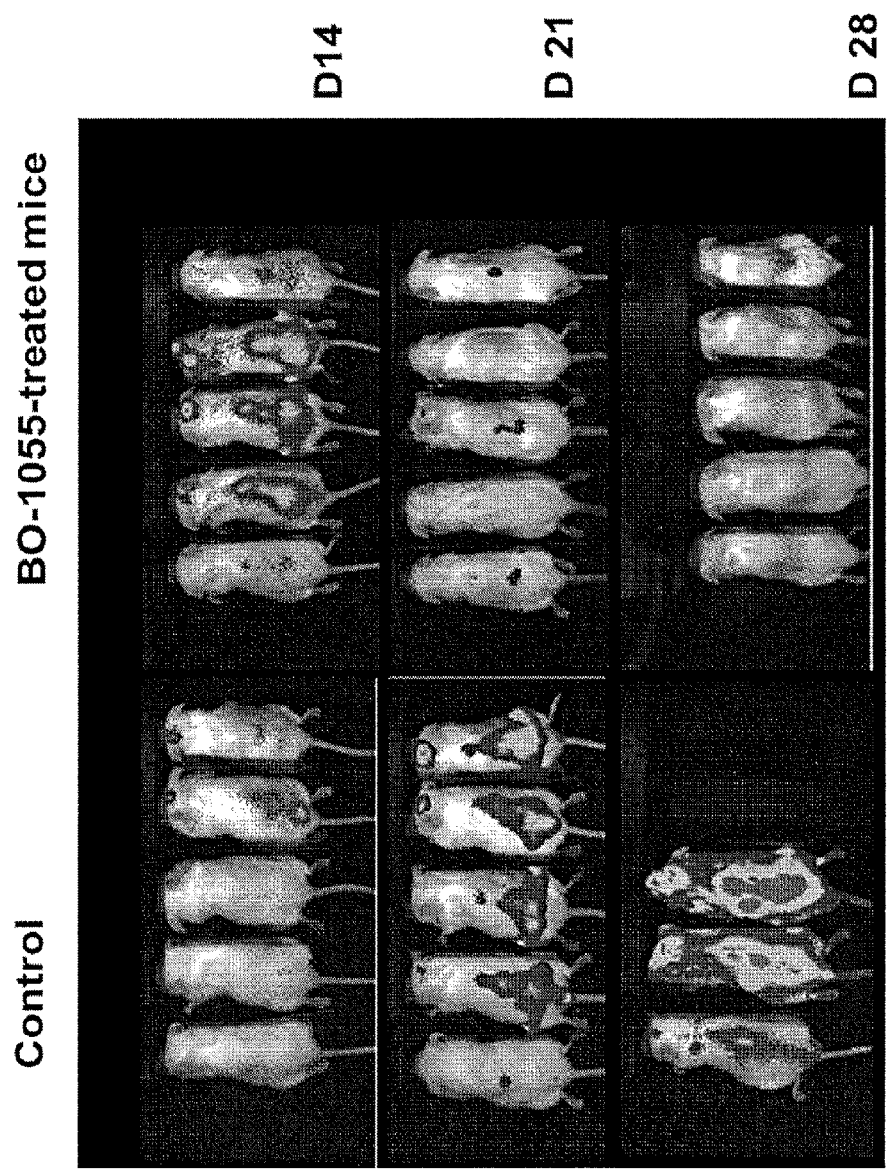
FIG. 11 depicts six bioimaging photograph panels of five mice each. The three panels on the left show mice which were only injected with MV4-11-GFP-Luciferase cells; and the three panels on the right show mice which were injected with MV4-11-GFP-Luciferase cells and were further treated with ureidomustine.

FIG. 11 shows the results of this experiment. The three panels on the left show mice which were only injected with MV4-11-GFP-Luciferase cells; and the three panels on the right show mice which were injected with MV4-11-GFP-Luciferase cells and were further treated with ureidomustine.

As shown in FIG. 11, 4/5 control mice (the left panel) showed rapidly growing tumor by day 28 with one mouse with only low engraftment. In the BO-1055 treated group (the right panel) at this time there was a very significant reduction in tumor engraftment compared to a week earlier with no tumor detected in 2 mice and very small tumor remaining in 3 mice. By day 28 there was no significantly detectable tumor in any of the five BO-1055 treated mice. In the control group at this time two mice had been euthanized due to massive tumor and the remaining mice showed extensive tumor requiring their euthanasia shortly after the day 28 imaging.

x) BO-1055 Treatment of NSG Mice Transplanted with the Human MA10 Cells Expressing GFP/Luciferase MA10 is an hGM-CSF-dependent AML cell line developed by retroviral transduction of the MLL-AF9 fusion oncogene and the activating Flt3 mutation (FltITD) into normal human CD34+ hematopoietic stem cells and progenitors. In the absence of GM-CSF in vitro or in vivo in NSG mice, MA10 cells did not proliferate. GM-CSF is species restricted, the human cytokine has no activity in mice and mouse GM-CSF is not active on human cells.

The inventors showed that daily i.p. injections of 1 μg of human GM-CSF into NSG mice transplanted with MA10 cells would support their engraftment and expansion (data not shown). The inventors also showed that s.c. implantation of an osmotic minipump (Alzet) releasing 1 ug/day of human GM-CSF for 42 days would sustain the continued expansion of MA10 cells.

Figure 12:
FIG. 12 depicts bioimaging photographs of mice which were transplanted with MA10 cells expressing GFP/Luciferase with: a) no cytokine support (on the left) and b) administration of human GM-CSF by minipump implant (right).

FIG. 12 demonstrates the results of transplantation i.v. of one million MA10 cells expressing GFP/Luciferase in NSG mice with no cytokine support (left) or with administration of human GM-CSF by minipump implant (right). Bioimaging was done at 28 days.

FIG. 12 shows comparative engraftment of MA10 with or without the minipump at day 18 post i.v. injection of one million cells. By 18-25 days there was significant leukemia engraftment demonstrated by luciferase bioimaging only in the presence of GM-CSF (two mice on the right) with no engraftment without hGM-CSF (two mice on left). This dramatic response of a human leukemia xenograft to BO-1055 monotherapy was particularly remarkable since, in contrast to nude mouse xenografts there was no functional NK cell or residual T or B-cell function that could facilitate tumor eradication after drug debulking by a chemotherapeutic agent.

xi) Xenograft Studies of BO-1055 in NSG Mice Transplanted with MA-10-W51 Cord Blood CD34+ Cells Transduced with MLL-AF9 and a Constitutively Active Flt3 Internal Tandem Duplication (W51) and Treated with Single Dose BO-1055.

NSG mice (group of six) were implanted s.c with minipumps producing hGM-CSF and were injected i.v. with $10^6$ MA-10-W51 cells representing a poor prognosis leukemia developed by transduction of cord blood CD34+ cells with MLL-AF9 and Flt3ITD oncogenes. At 10 days after leukemic cell injection a single dose of BO-1055 of 30 mg/kg was administered to half the mice with the remainder getting an injection of media alone.

Figure 13:
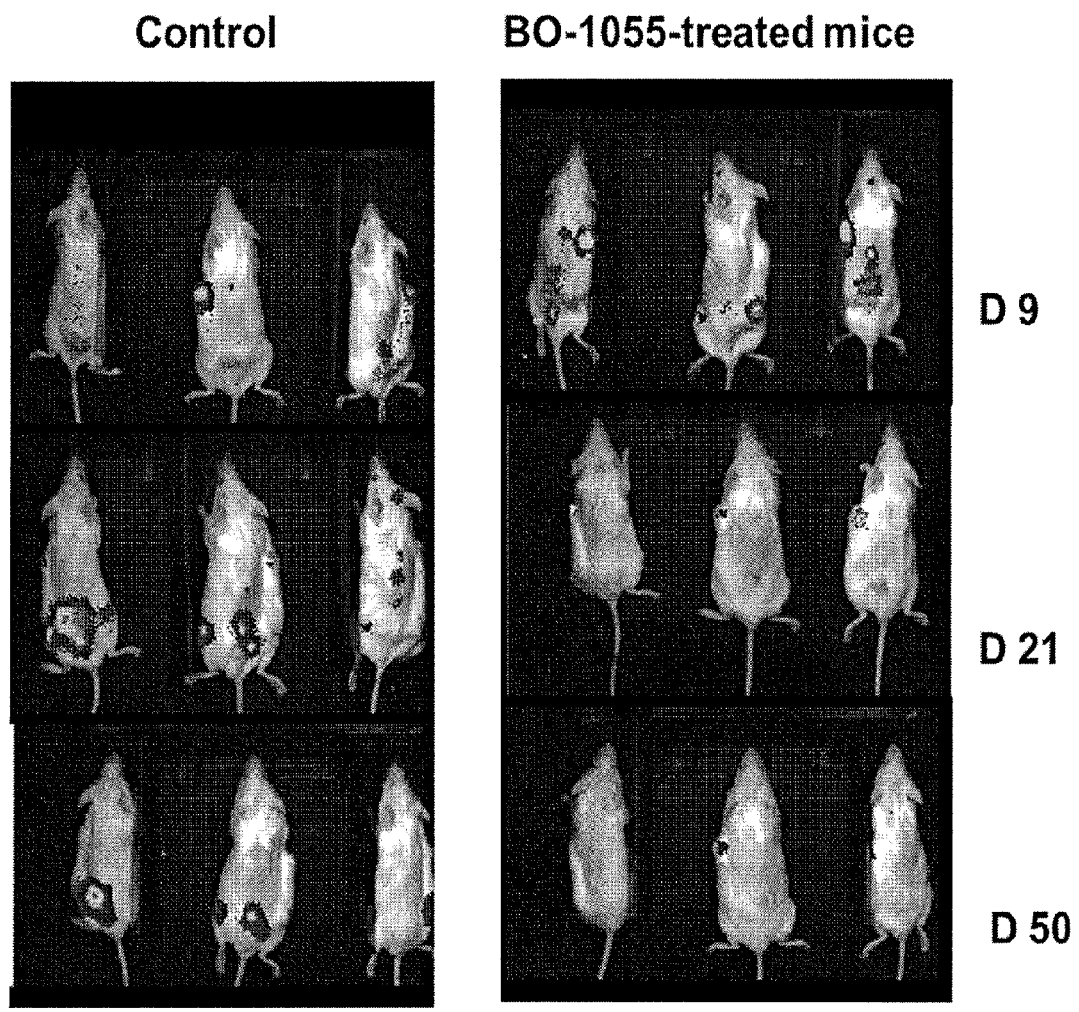
FIG. 13 depicts bioimaging photographs of six mice each transplanted with MA-10-W51-GFP-Luciferase cells; the three mice on the left received a control injection, and the three mice on the right received ureidomustine injection.

As shown in FIG. 13, this leukemia grew slowly but by day 50 was clearly engrafted in all control mice (on the left) whereas in the BO-1055 treated mice (on the right), it was undetectable or borderline engrafted at best. This tumor suppressive effect was particularly remarkable since it was obtained with only a single dose of 30 mg/kg BO-1055.

xii) In Vitro and In Vivo Cytotoxicity of BO-1055 Against a Primary (MLL-AF9+) Pediatric AML.

A sample of bone marrow from a pediatric patient with MLL-AF9+ AML was obtained at diagnosis and transduced with a lentivector expressing a GFP/luciferase fusion gene. GFP+CD34+ cells were isolated by FACS and $10^5$ cell injected i.v. into each of six 12 wk old NSG mice. Mice were imaged at intervals and at day 35 after initial engraftment, half the mice began BO-1055 treatment (30 mg/kg every other day ×5) and half received control medium.

Figure 14:
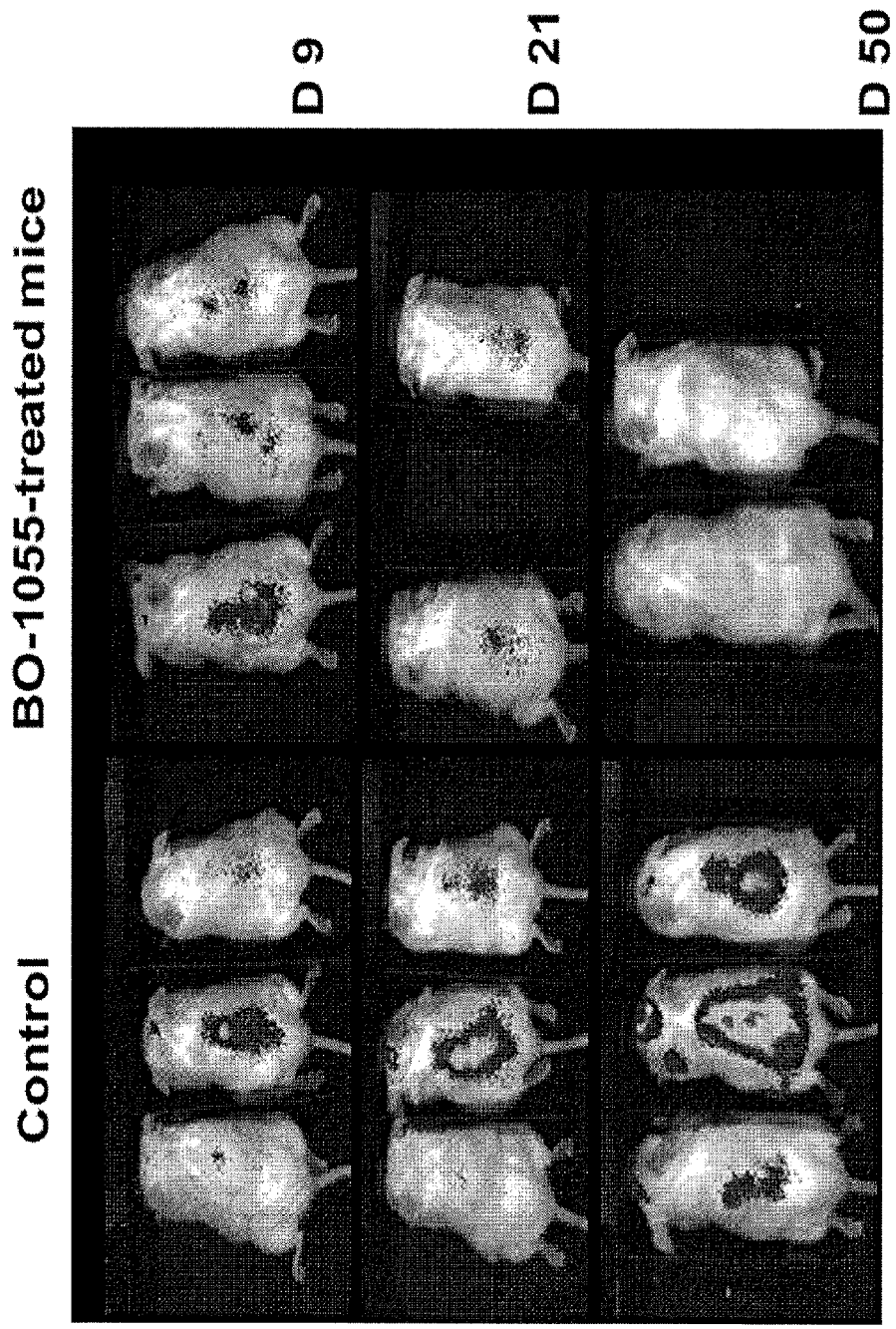
FIG. 14 depicts six bioimaging photograph panels of five mice each. The three panels on the left show mice which were only injected with AML-2-CD34+-GFP-Luciferase cells; and the three panels on the right show mice which were injected with AML-2-CD34+-GFP-Luciferase cells and were further treated with ureidomustine.

As shown in FIG. 14, there was no detectable leukemia in the treated mice whereas all the control mice had progressively growing leukemia. One mouse in the treated group died 24 hrs after initiation of treatment but unrelated to therapy. BO-1055 treated mice showed tumor regression with no detectable tumor by day 47 (4 days after the last drug treatment).

xiii) Kaplan-Meyer Survival Analysis of NSG Mice Engrafted with Second Passage MLL-AF9+AML-2.

Figure 15:
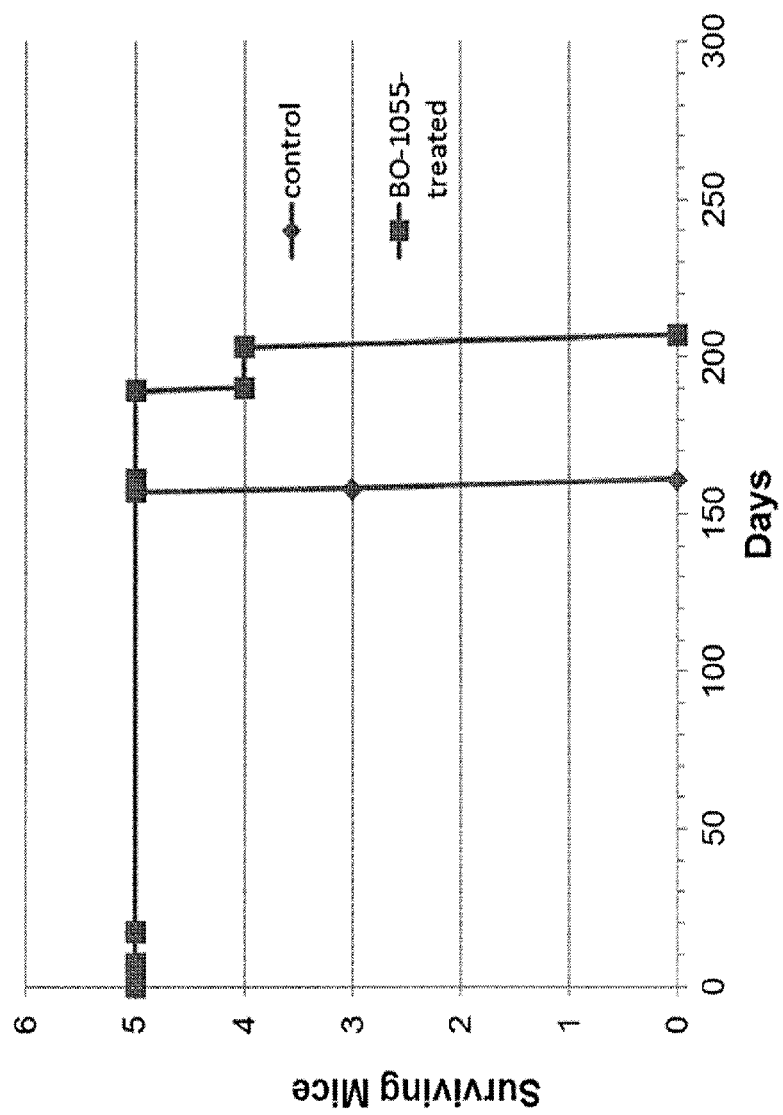
FIG. 15 is a chart of days after administration of ureidomustine vs the number of surviving mice engrafted with primary patient-derived AML-2 CD34+ cells.

As shown in FIG. 15, NSG mice injected i.v with $6×10^6$ cells from a primary AML sample from a pediatric patient with MLL-AF9+ leukemia all died by 160 days whereas the group treated with BO-1055 (30 mg/kg Q10D2x) beginning at day 7 after leukemic cell injection lived 48 days longer. This response was particularly significant in view of the relatively large number of leukemic cells injected, and the poor prognosis phenotype of the leukemia.

xiv) In Vitro and In vivo Cytotoxicity of BO-1055 Against a Primary Pediatric B-ALL.

A sample of bone marrow from a pediatric patient with B-ALL was cultured in vitro in the presence or absence of BO-1055 titrated over a dose range from 0.001-20.0 μm.

Figure 16:
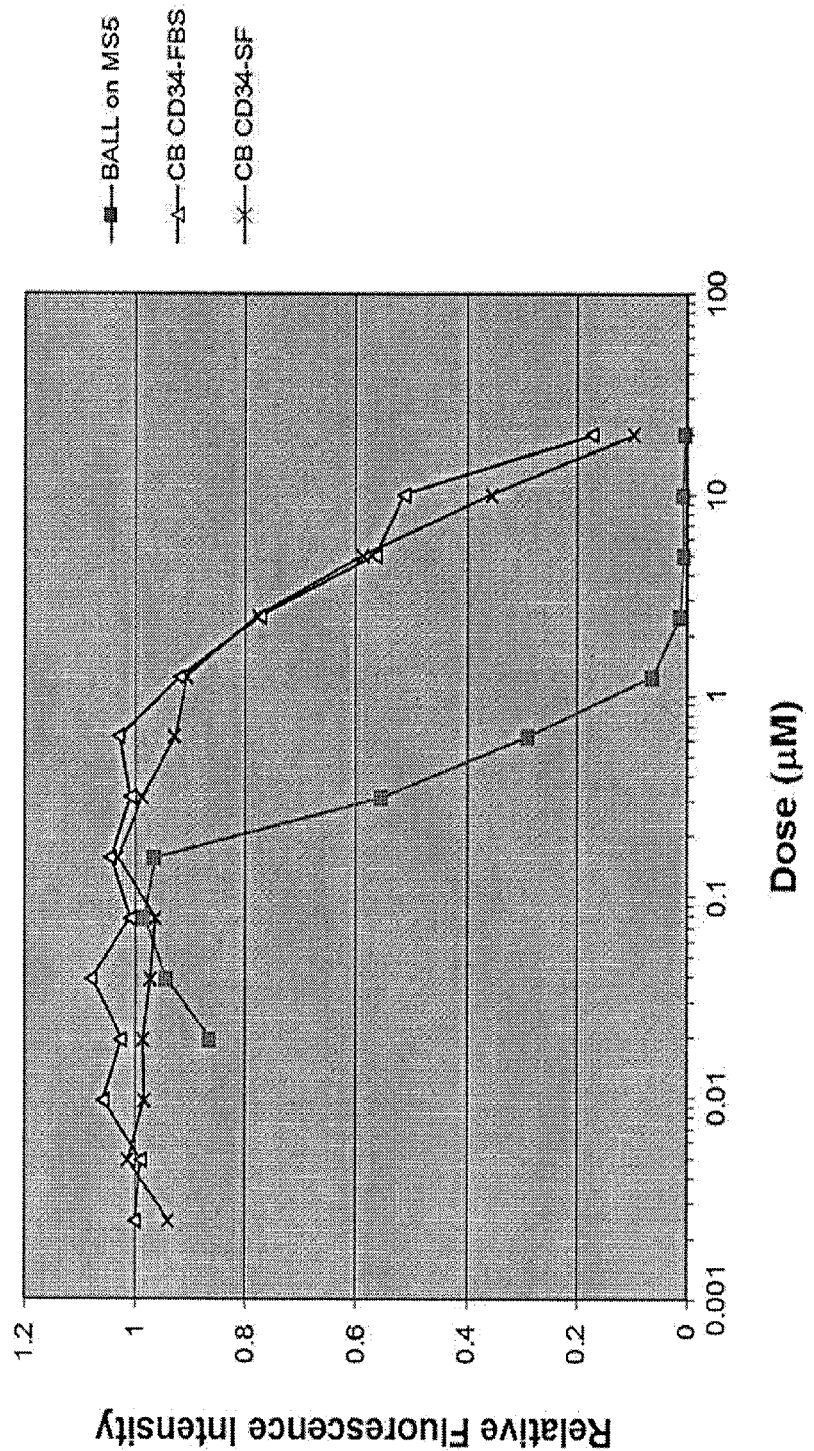
FIG. 16 shows alamar blue fluorescence intensity dose-response curves of BO-1055 cytotoxicity at 72 hrs against a primary patient pre-B ALL leukemia. compared to normal cord blood CD34+ HPC/HSC

The dose response curve was compared to that obtained using normal cord blood CD34+ cells maintained in FBS-containing media or in serum free media (FIG. 16) BO-1055 was highly cytotoxic to the B-ALL cells ($IC_{50}$ 0.30 μM) while the normal cord blood CD34+ cells in either FCS-containing media or in serum-free medium ("serum replacement" medium with supplements), were relatively resistant to BO-1055 toxicity ($IC_{50}$ 8.5-10.5 μM). The B-ALL cells were then transduced with a lentivirus vector expressing a GFP/Luciferase fusion gene and GFP+CD34+ cells were selected by FACS (FIG. 17).

xv) FACS Analysis of Primary B-ALL.

Figure 17:
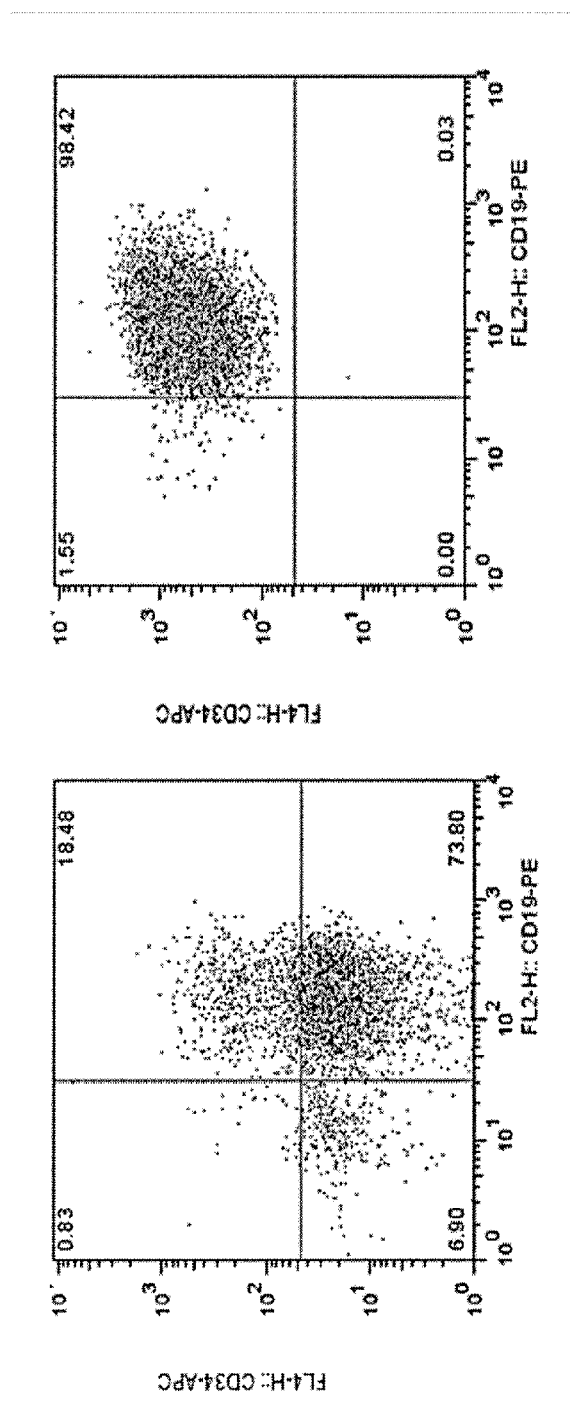
FIG. 17 shows a flow cytometry distribution of pre-B-ALL cells expressing CD19 and/or CD34 following ureidomustine treatment.

FIG. 17 demonstrates the results of the experiment whereby primary B-ALL Cells were separated by Ficoll density gradient and light density cells further selected by a CD34 affinity column and then FACS analyzed for CD34 and CD19 expression.

By combined CD34 and the B-cell marker CD19 in FACS analysis, 19.3% of cells in the primary sample were CD34. The vast majority of these CD34 cells were CD34+CD19+ double positive. After affinity column separation, 100% were CD34+ and 98.4% were double positive CD34+ CD19+(FIG. 17).

xvi). Organ Distribution of Primary Pediatric B-ALL Cells after Transplantation in NSG Mice.

NSG mice were transplanted with either 2 million CD34+ B-ALL cells or 2 million unseparated cells. Following engraftment, the organ distribution was determined by FACS analysis using monoclonal antibodies to human CD34 and human CD19 (Table 16). Massive spleen enlargement was evident with splenic cellularities of 310-400 million cells, an increase in cellularity compared to normal NSG mice of 30-40-fold. The 63-74% of this increase was due to expansion of human CD19+ cells and of these, 50-54% were CD34+B-ALL cells. The engrafted cells also extensively infiltrated the bone marrow with 37-56 million cells per femur and of these 92-96% were human CD19+ and 68-81% were human CD34+CD19+. The B-ALL cells were also present in the peripheral blood (1% human CD34+CD19+ and 2% CD34-CD19+ cells)

TABLE 16

Engraftment and tissue distribution human primary B-ALL cells following transplantation in NSG mice.

| Tissue | Cell number | hCD34+CD19+ | hCD34−CD19+ |
|---|---|---|---|
| #1* Spleen | 370 million, | 50.17% | 12.62% |
| #1 BM | 40 million | 81.18% | 14.68% |
| #2* Spleen | 310 million | 53.53% | 12.24% |
| #2 BM | 37 million | 74.44% | 20.97% |
| #3* Spleen | 390 million | 46.59% | 20.67% |
| #3* BM | 41 million | 79.13% | 16.02% |
| #4 Spleen | 310 million | 48.95% | 17.73% |
| #4 BM | 38 million | 68.20% | 27.64% |
| #5 Spleen | 400 million | 50.43% | 23.44% |
| #5 BM | 56 million | 68.22% | 24.33% |

*#1-#3 received 2 million CD34+ cells, #4-#5 received 2 million unbound cells.

xvii) Effect of BO-1055 on NSG Mice Transplanted i.v. With Primary Pre-B-ALL-GFP-Lu Cells The six mice transplanted with the primary Pre-B-ALL cells used in FIG. 19 showed rapid tumor growth and suppression of tumor growth within 7 days of initiation of BO-1055 treatment (Q10D2× beginning at day 7) (FIG. 18).

Figure 18:
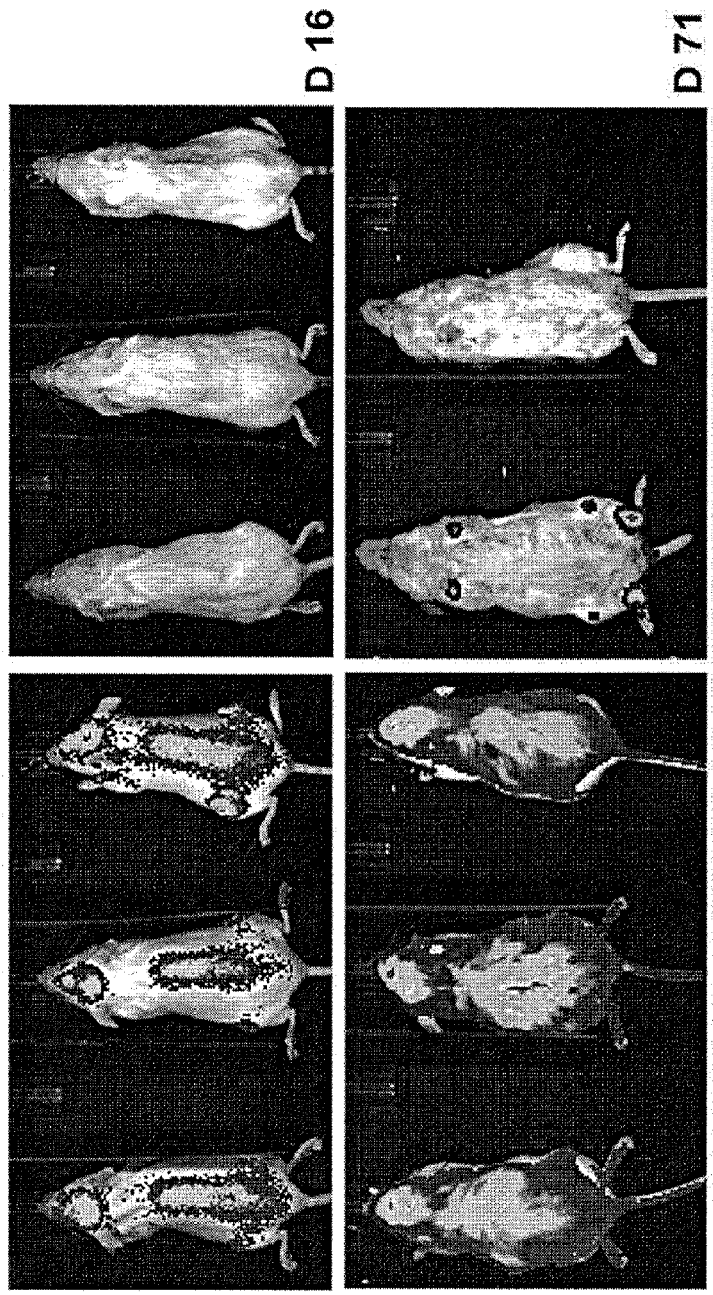
FIG. 18 shows four bioimaging photograph panels of three mice each. The three panels on the left show mice which were only injected with Pre-B-ALL CD34-GFP-Luciferase cells and control media; and the three panels on the right show mice which were injected with Pre-B-ALL CD34-GFP-Luciferase cells and were further treated with ureidomustine.

FIG. 18 shows four bioimaging photograph panels of three mice each. The three panels on the left show mice which were only injected with Pre-B-ALL CD34-GFP-Luciferase cells and control media; and the three panels on the right show mice which were injected with Pre-B-ALL CD34-GFP-Luciferase cells and were further treated with ureidomustine.

By 71 days, control mice had extensive tumor infiltration, primarily within the bone marrow of the spine and cranium whereas one of the two surviving BO-1055 treated mice had no detectable tumor and the other had small leukemia foci primarily in the heads of the femur and humerus. A third mouse died of causes unrelated to tumor development or therapy. This data shows a significant 2 log reduction of tumor growth in the BO-1055 treated mice.

Figure 19:
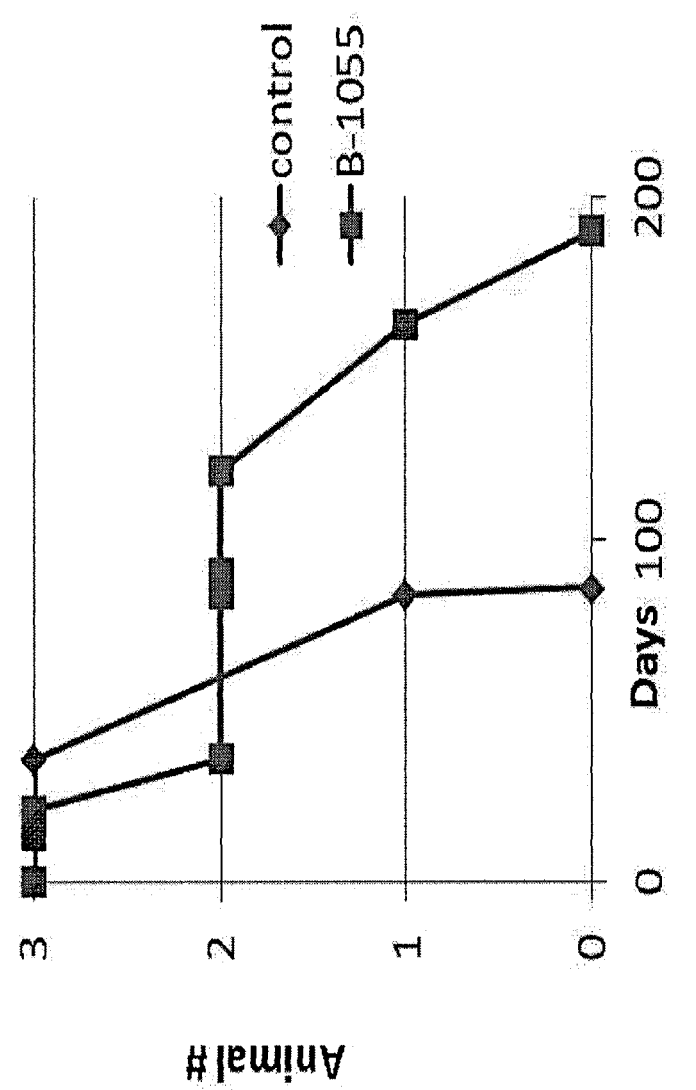
FIG. 19 shows a survival analysis chart of mice engrafted with pre-B-ALL cells treated with ureidomustine and control.

A Kaplan-Meyer survival curve calculated for primary B-ALL tumor-bearing mice in the xenograft study with or without BO-1055 treatment is shown in FIG. 19. This schedule of BO-1055 had a very significant effect on overall survival of tumor-bearing mice with the drug treated group surviving ~100 days longer than the control-treated group.

Example 13B

Lung Cancer

There were 1.6 million cases of lung cancer world-wide in 2014. There were 224,210 new cases in the US with 159,260 deaths and a 5-year survival of 16.8%. If diagnosed at an early stage (IA) 5-year survival is 49% but if diagnosed at stage IV it is 1%.

(i) Lung Cancer Subtypes.

Lung cancer is a large and exceptionally heterogeneous family of malignancies. Over 50 different histological variants are explicitly recognized within the 2004 revision of the World Health Organization (WHO) typing system (Brambilla et al. 2001). Lung cancers are broadly classified by histological type into non-small cell lung cancer (NSCLC) and small cell lung cancer (SCLC).

(ii) Non-Small Cell Lung Cancer (NSCLC)

NSCLC can be subdivided into adenocarcinoma, large cell carcinoma and squamous cell carcinoma. Adenocarcinomas are the most frequent (40% of all lung cancers) followed by squamous (30%), small-cell (13-15%), and large-cell (9-10%) (Travis et al. 2004). Rare subtypes are giant cell carcinoma, sarcomatoid carcinoma, rhabdoid carcinoma and papillary adenocarcinoma. Bronchioalveolar carcinoma is a subtype of adenocarcinoma that occurs more frequently in women non-smokers and has a better prognosis. Numerous cell lines have been derived from these subtypes, and some lines may have features of more than one subtype e.g. adenosquamous lines. Mutations in the K-Ras proto-oncogene are responsible for 10-30% of lung adenocarcinomas and about 4% of non-small-cell lung carcinomas involve an EML4-ALK tyrosine kinase fusion gene (Sasaiki et al 2010). Mutations and amplification of the epidermal growth factor receptor (EGFR) are common in NSCLC and provide the basis for treatment with EGFR-inhibitors. Her2/neu is affected less frequently (Dempke et al. 2010). Other genes that are often mutated or amplified are c-MET, NKX2-1, LKB1, PIK3CA and BRAF (Dempke et al. 2010, Dela Cruz et al. 2011).

(iii) Cytotoxicity of BO-1055 Compared to Four Alkylating Drugs on a Panel of 43 NSCLC Cell Lines.

An extensive panel of NSCL lines was assembled to cover morphological subtypes including adenocarcinoma (30 lines), adenosquamous (4 lines) and squamous (9 lines).

Table 17 shows the $IC_{50}$ values of BO-1055 compared to four other alkylating chemotherapeutic agents-the alkylating platinum drugs carboplatin and cisplatin, and the alkylating drugs melphalan and BCNU (bendamustine) on a panel of 45 human cell lines representative of non-small cell lung cancer adenocarcinoma, squamous cell carcinoma and cell lines showing mixed adeno- and squamous morphology. Of these, 38 lines were evaluated for BO-1055 cytotoxicity and 18 were found to be resistant ($IC_{50} \geq 10$ uM), 6 were weakly resistant ($IC_{50}$ 5.0-9.9 uM), 13 were weakly sensitive ($IC_{50}$ 1.0-4.9) and only 1 was highly sensitive ($IC_{50}$<1.0 uM). In the adenocarcinoma group 9/26 lines were in the moderately to highly BO-1055 chemo-sensitive group, including lines with mutations in EGFR, KRAS (×2) HER2/4, EML4-ALK (×2), TP53, BRAF, and deleted SMARCA4. In the squamous and adeno-squamous group 5/12 lines were moderately sensitive and 7/12 were moderately to highly resistant to BO-1055. Oncogenes upregulated or mutated in the moderately sensitive group included PIK3C, KRAS, FGFR, CDKN2A, and TP53.

From these observations it can be concluded that the cytotoxicity of BO-1055 is not significantly determined by the mutation status of the cancer since cell lines with the same mutation can be sensitive or resistant. The molecular basis for differential sensitivity to BO-1055 in lung cancer cell lines remains to be determined.

TABLE 17

The cytotoxicity ($IC_{50}$ μM) of BO-1055 compared to 4 alkylating drugs, carboplatin, cisplatin, melphalan, and BCNU on 30 NSCLC adenocarcinomas, 4 lung adeno-squamous cell lines, and 9 lung squamous cell cancer lines.

| | 1055 | Carb | Cisp | Melph | BCNU |
|---|---|---|---|---|---|
| NSCLC (mutation) | | | | | |
| CALU-1 (KRAS) | ≥20.0 | 96.18 | ≥20.0 | | |
| CALU-3 HER2, CDKN2A, p53 | ≥10.0 | 84.50 | ≥100.0 | | |
| CALU-6 (KRAS) | 3.31 | 14.70 | 3.25 | | |
| CL1-0 | 14.6 | | | | |

TABLE 17-continued

The cytotoxicity (IC$_{50}$ μM) of BO-1055 compared to 4 alkylating drugs, carboplatin, cisplatin, melphalan, and BCNU on 30 NSCLC adenocarcinomas, 4 lung adeno-squamous cell lines, and 9 lung squamous cell cancer lines.

| | 1055 | Carb | Cisp | Melph | BCNU |
|---|---|---|---|---|---|
| CL100T1 | ≥10.0 | | 2.80 | | |
| CL1-5 | 6.08 | | | | |
| CL141T (TP53) | ≥10.0 | | 2.45 | | |
| CL97 | ≥10.0 | | ≤15.0 | | |
| H125 no mutations* | | | 1.50 | 8.20 | ≥100.0 |
| H1395 (BRAF, STK11) | ≥10.0 | 17.41 | ≥15.0 | | |
| H1650 (EGFR, PTEN del) | 6.20 | 69.70 | 7.51 | | |
| H1666 (BRAF) | ≥10.0 | 90.71 | ≥20.0 | | |
| H1755 (BRAF) | ≥20.0 | 41.41 | ≥15.0 | | |
| H1781 (HER2/4) | 0.39 | 3.99 | 1.67 | | |
| H1975 (EGFR) | ≥10.0 | 60.16 | ≥10.0 | | |
| H1993 (MET amp.) | 6.72 | | | | |
| H2228 (EML4-ALK) | 1.70 | 8.62 | ≥25.0 | | |
| H23 KRAS p53 STK1 SMARKA4 | | | 2.50 | 8.70 | ≥100.0 |
| H3122 (EML4-ALK) | 4.87 | 109.0 | ≥30.0 | | |
| H3255 (EGFR) | 2.04 | 24.28 | ≥25.0 | | |
| H358 KRAS | | | 5.90 | ≥30.0 | ≥75.0 |
| H522 (KRAS, TP53, SMARCA4 del) | 3.00 | | | ≥30.0 | |
| H525 | 1.40 | 72.70 | 7.74 | | |
| HCC364 (BRAF) | 4.00 | 172.0 | ≥75.0 | | |
| HCC5 (PIK3CA) | ≥10.0 | | | | |
| HCC827 (EGFR, KRAS, MET amp). | 5.53 | 138.4 | | | |
| HEL299 | | | 1.80 | | |
| MOR | | | 3.90 | | |
| PC9 (EGFR) | ≥10.0 | 32.10 | 8.12 | | |
| PC9/gefb4 Gefetinib resistant | ≥10.0 | | ≥35.0 | | |
| SK-LU-1 (KRAS) | 4.23 | 42.38 | 6.94 | | |
| Lung Adenosquamous | | | | | |
| H1373 (KRAS) | ≥10.0 | 29.30 | 9.46 | | |
| H322 None reported | | ≥10.0 | ≥10.0 | ≥75.0 | ≥200.0 |
| H596 (PIK3CA) | 4.00 | 34.10 | ≥10.0 | ≥55.0 | ≥225.0 |
| H647 (KRAS) | ≥10.0 | 25.50 | 8.75 | ≥55.0 | ≥150.0 |
| Lung Squamous Cell Ca | | | | | |
| A549 CDKN2A KRAS STK11 (del SMARK4, LKB1) | 1.40 | 41.30 | ≥30.0 | ≥10.0 | |
| A549-DR Cisplatin resistant | ≥10.0 | | | | |
| EBC1 (MET amp) | 4.51 | 168.0 | ≥100.0 | | |
| H1703 (FGFR, TP53, CDKN2A/SMARCA4) | 1.67 | ≥80.0 | ≥20.0 | | |
| H226 none reported | | | 2.90 | ≥55.0 | ≥150.0 |
| H520 (FGFR) | 5.00 | 75.61 | 9.10 | ≥25.0 | ≥120.0 |
| HCC15 (HER4, NRAS, MET) | 6.15 | 173.0 | ≥85.0 | | |
| HCC2450 (PIK3C) | 3.00 | 34.53 | ≥80.0 | | |
| PC1 (jap) | ≥10.0 | 57.42 | ≥20.0 | | |
| SK-MES-1 (KRAS) | ≥10.0 | 160.0 | ≥50.0 | | |

*COSMIC Catalogue of Somatic Mutations in Cancer (iv) Large-Cell Lung Carcinoma (LCLC).

Of the non-small cell lung cancers, this type is usually discovered at a later stage. LCLCs tend to grow quickly and spread to nearby lymph nodes and into the thoracic wall. It also can spread to more distant organs, even when the tumor in the lung is relatively small. There are approximately 20,000 new cases annually in the U.S.

One clinically significant subtype of LCLC is "large-cell neuroendocrine carcinoma" (LCNEC), which is believed to derive from neuroendocrine cells. In addition, a "subvariant", called "combined large-cell neuroendocrine carcinoma" (or c-LCNEC), is recognized under the new WHO classification. To be designated a c-LCNEC, the tumor must contain at least 10% LCNEC cells, in combination with at least 10% of other forms of NSCLC.

(v) Cytotoxicity of 42 BO-compounds Against 4 Large-Cell Lung Cancer Lines.

The inventors have evaluated the cytotoxicity of BO-1055 42 to four Large-Cell Lung Cancer lines (H1299, H299, H460, and SHP77). As shown in Table 18, the tested cell lines were in the moderately to highly chemo-sensitive to BO-1055.

TABLE 18

Cytotoxicity (IC$_{50}$ μM) of BO-1055 against four Large-Cell Lung Cancer lines. (Note SHP77 is considered to be a derivative of SCLC or to be mixed SCLC/LCLC)

| Large-Cell Lung Cancer | LCLC mutations | 1055 |
|---|---|---|
| H1299 | TP53 NRAS, SMARCA4 | 10.4 |
| H299 | NRAS | 5.34 |
| H460 | PIK3CA, KRAS, LKB1. (TP53wt) | 6.20 |
| SHP77* | SCLC variant large cell | ≥40.0 |

(vi). Small-Cell Lung Carcinoma (SCLC).

This lung carcinoma is derived from neuroepithelial or neuroendocrine cells of the bronchioles and may express CD44. The cells contain dense neurosecretory granules which give this tumor an endocrine/paraneoplastic syndrome association. Most cases arise in the larger airways, grow quickly and spread early in the course of the disease with 60-70% metastasis at presentation.

(vii) Combined Small-cell Lung Carcinoma (c-SCLC).

This is considered a variant of CLC under the current World Health Organization lung tumor classification scheme. It is a multiphase lung cancer that contains a component of SCLC admixed with one (or more) components of NSCLC. While the true incidence of c-SCLC is unknown, case series suggest that they may account for as many as 25% to 30% of all cases of SCLC, and for 4% to 6% of all lung cancer cases. EGFR mutations are very rare (<5%) in "pure" SCLC, but they are considerably more common (about 15%-20%) in c-SCLC. These positive tumors are more likely to respond to treatment with EGFR-TKI's. c-SCLC appear to express female hormone (i.e. estrogen and/or progesterone) receptors in a high (50%-67%) proportion of cases, similar to breast carcinomas. However, it is at present unknown whether blockade of these receptors affects the growth of c-SCLC.

(viii) Cytotoxicity of BO-1055 on Variant Forms of Small Cell Lung Cancer Cell Lines.

Three examples of the variant form of SCLC are provided by the NCI cell lines H82, H211 and H526. As shown in Table 19, two lines were highly sensitive to BO-1055 ($IC_{50}$ 0.34-0.39 µM), while one was moderately sensitive ($IC_{50}$ 2.00 µM)

TABLE 19

Cytotoxicity ($IC_{50}$ µM) of BO-1055 on three variant Small Cell Lung Cancer cell lines ($IC_{50}$ µM ± S.D.)

| $IC_{50}$ (µM) | H82 | H211 | H524 |
|---|---|---|---|
| BO-1055 | 0.39 ± 0.05 | 2.00 ± 1.01 | 0.34 ± 0.01 |

(ix) Cytotoxicity of BO-1055 on a Panel of SCLC Lines Compared to the Toxicity of Other Alkylating Drugs and Chemotherapeutic Agents.

Eleven SCLC lines, including classic and variant forms of SCLC, were evaluated for BO-1055 72 hr cytotoxicity using the alamar blue assay (Table 20). Six lines including 3 classic and 3 variant were very sensitive ($IC_{50}$ 0.05-0.39 µM) with a Therapeutic Index (TI) range of 25-200. One was moderately sensitive ($IC_{50}$ 2.00 µM) with a TI of 5 and four, including 2 classic and 2 variant were resistant ($IC_{50}$ 20-40 µM) with a TI of 0.4-1.6. The three alkylating agents (cisplatin, melphalan and BCNU (carmustine)) also showed high cytotoxicity against some lines, and resistance with others.

With cisplatin treatment, 3/19 lines were highly sensitive ($IC_{50}$<1.0 µM), 14/19 were moderately sensitive ($IC_{50}$ 1.0-4.9 µM) and 2/19 were highly resistant ($IC_{50}$ >10.0 µM).

Similarly, with melphalan, 4/16 lines were highly sensitive, 5/16 moderately sensitive, 2/16 moderately resistant and 5/16 highly resistant. All lines tested were highly resistant to BCNU/carmustine. The anthracycline antitumor antibiotic doxorubicin was highly cytotoxic to all 17 lines it was tested on. Doxorubicin is not a component of any of the main protocols for combination chemotherapy of SCLC, possible a reflection on the potential severe side effects, particularly cardiotoxicity. Vincristine was highly cytotoxic to 16/17 lines with one moderately sensitive. VP-16/etoposide showed a mixed patter of toxicity with 6/16 lines highly sensitive, 5/16 moderately sensitive, 2/16 moderately resistant and 3 highly resistant. There was no evidence of cross resistance between alkylating agents and BO-1055. For example, the H82 line was very sensitive to BO-1055 but highly resistant to cisplatin, melphalan and BCNU as well as etoposide, and was the most resistant of all lines tested to doxorubicin.

TABLE 20

Cytotoxicity ($IC_{50}$ µM) of BO-1055 compared to three alkylating drugs (Cisplatin, Melphalan, BCNU/Carmustine), an anthracyclin antitumor antibiotic (Doxorubicin/Adriamycin), a vinca alkaloid tubulin binder and cell cycle inhibitor (Vincristine/Oncovin) and a topoisomerase II inhibitor (VP-16/Etoposide) screened on a panel of 21 SCLC cell lines, including classical and variant examples.

| SCLC LINES | BO-1055 | Cisp | Melph | BCNU | Doxo | Vinc | VP-16 |
|---|---|---|---|---|---|---|---|
| DMS-79 classic | 0.05 | | | | | | |
| H128 classic | | 4.79 | ≥20 | ≥75 | 0.10 | 0.005 | ≥25 |
| H146 classic | | 3.77 | ≥15.0 | ≥95 | 0.14 | 2.90 | 2.90 |
| H187 classic | | 1.01 | 1.80 | ≥35 | 0.03 | 0.001 | 0.60 |
| H209 classic | | 0.31 | 0.20 | ≥35 | 0.03 | 0.001 | 0.50 |
| H211 variant | 2.00 | 1.21 | | | 0.15 | 0.002 | |
| H249 classic | | 1.51 | ≥10.0 | ≥75 | 0.13 | 0.001 | 4.10 |
| H345 classic | 23.0 | | | | | | |
| H417 variant | | 2.01 | 0.80 | ≥75 | 0.01 | 0.002 | 3.70 |
| H524 variant | 0.34 | 0.41 | 2.79 | ≥45 | 0.02 | 0.001 | 1.40 |
| H526 variant | 0.12 | 2.85 | 0.10 | ≥30 | 0.01 | 0.136 | 0.80 |
| H562 classic | 0.25 | 1.39 | 2.80 | ≥35 | 0.17 | 0.001 | 5.50 |
| H60 classic | | 2.09 | ≥10.0 | 36.0 | 0.13 | 0.002 | ≥20 |
| H69 classic | <20.0 | 3.42 | 6.30 | 103.1 | 0.06 | 0.003 | 0.40 |
| H678 classic | | 3.81 | 0.10 | ≥125 | 0.01 | 0.002 | 0.31 |
| H719 classic | | 1.12 | 7.91 | ≥100 | 0.09 | 0.002 | ≥10 |
| H82 variant | 0.39 | ≥20.0 | 84.0 | ≥150 | 0.23 | 0.007 | 9.70 |
| H841 variant | | ≥20.0 | 3.60 | | 0.02 | 0.002 | 0.60 |

TABLE 20-continued

Cytotoxicity (IC$_{50}$ µM) of BO-1055 compared to three alkylating drugs (Cisplatin, Melphalan, BCNU/Carmustine), an anthracyclin antitumor antibiotic (Doxorubicin/Adriamycin), a vinca alkaloid tubulin binder and cell cycle inhibitor (Vincristine/Oncovin) and a topoisomerase II inhibitor (VP-16/Etoposide) screened on a panel of 21 SCLC cell lines, including classical and variant examples.

| SCLC LINES | BO-1055 | Cisp | Melph | BCNU | Doxo | Vinc | VP-16 |
|---|---|---|---|---|---|---|---|
| H889 classic | 0.25 | 0.41 | 2.79 | ≥45 | 0.02 | 0.001 | 1.40 |
| N-417 variant | 30.0 | | | | | | |
| SHP-77 variant | 40.0 | | | | | | |

(x) Determination of the Therapeutic Window of BO-1055 on the SCLC Cell Line H526 Compared to Other Alkylating Drugs and Chemotherapeutic Agents.

The "Therapeutic Window" (TW) was calculated from in vitro cytotoxicity determinations (IC$_{50}$ values) of BO-1055 on the malignant cell line, in this example (Table 20) the SCLC variant line H526, compared to the cytotoxicity of the compound on a panel of normal human tissues. The benign tissues included (a) human umbilical cord as a neonatal source of endothelial cells (HUVEC); (b) adult human bone marrow mesenchymal cells (huMSC); (c) normal human lung bronchial epithelium immortalized by retroviral transduction of hTERT (Bci-NSI); (d) normal human Fallopian tube basal epithelium immortalized by retroviral transduction of hTERT (FTEC) and (e) human cord blood-derived CD34+ hematopoietic cells, a population comprised of hematopoietic stem cells (HSC 5%) and hematopoietic progenitor cells (CFC 95%) of the erythroid, granulocyte/monocyte, megakaryocyte and B-lymphocyte lineages.

There was an excellent therapeutic window of 100-533-fold for BO 1055 between its toxicity against H526 and lack of toxicity against the panel of normal tissues screened. This was in marked contrast to the significantly smaller therapeutic window evident in the comparison with other drugs, including the alkylating drugs 4-Hydroxycyclophosphamide (4-HC), bendamustine, melphalan and cisplatin, and also with the topoisomerase inhibitors etoposide, SN38, the HSP90 inhibitor PUH71 and the microtubule binding alkaloid Vincristine.

TABLE 21

The therapeutic window (TW) obtained with BO-1055 on the H526 variant SCLC cell line compared to its lack of toxicity on normal epithelium, endothelium, mesenchymal stroma and normal hematopoietic progenitor cells (CFC). Data normalized to a value of 1.00 for H526.

| Chemicals | CD34+ | HUVEC | huMSC | Bci- | FTEC | H526 |
|---|---|---|---|---|---|---|
| BO-1055 | 100.0 | 333.33 | 133.33 | 266.67 | 533.33 | 1.00 |
| 4-HC | 1.68 | 33.75 | 33.75 | 15.00 | 10.42 | 1.00 |
| Benamustine | 1.60 | 24.00 | 48.00 | 24.00 | 64.00 | 1.00 |
| Melphalan | 1.20 | 10.00 | 4.00 | 6.00 | 20.00 | 1.00 |
| Cisplatin | 33.33 | 58.33 | 75.00 | 83.33 | 1041.7 | 1.00 |
| Doxorubicin | 0.23 | 0.90 | 180.00 | 1.28 | 512.82 | 1.00 |
| Etoposide | 0.75 | 5.83 | 10.50 | 25.00 | 1333.3 | 1.00 |
| PUH71 | 0.70 | 40.00 | 20.00 | 50.00 | 200.00 | 1.00 |
| SN-38 | 8.67 | 0.93 | 23.33 | 740.74 | 925.93 | 1.00 |

(xi) In vivo Studies of NSG Mouse Xenografts of the Small Cell Lung Cancer Cell Line H526 Treated with BO-1055.

Xenografts of GFP/Luciferase-labeled H526 were established in groups of ten NSG male mice aged 12 wks by subcutaneous injection of 50,000 tumor cells. Luciferase bioimaging was done at day 12 and five mice were then injected intravenously with 30 mg/kg BO-1055 and 5 mice with culture medium as the control. BO-1055 or control medium injections were repeated every second day from day 12 to day 30 and bioimaging done at day 12 at baseline and at day 21, 26 and 30 during drug treatment.

Figure 20:
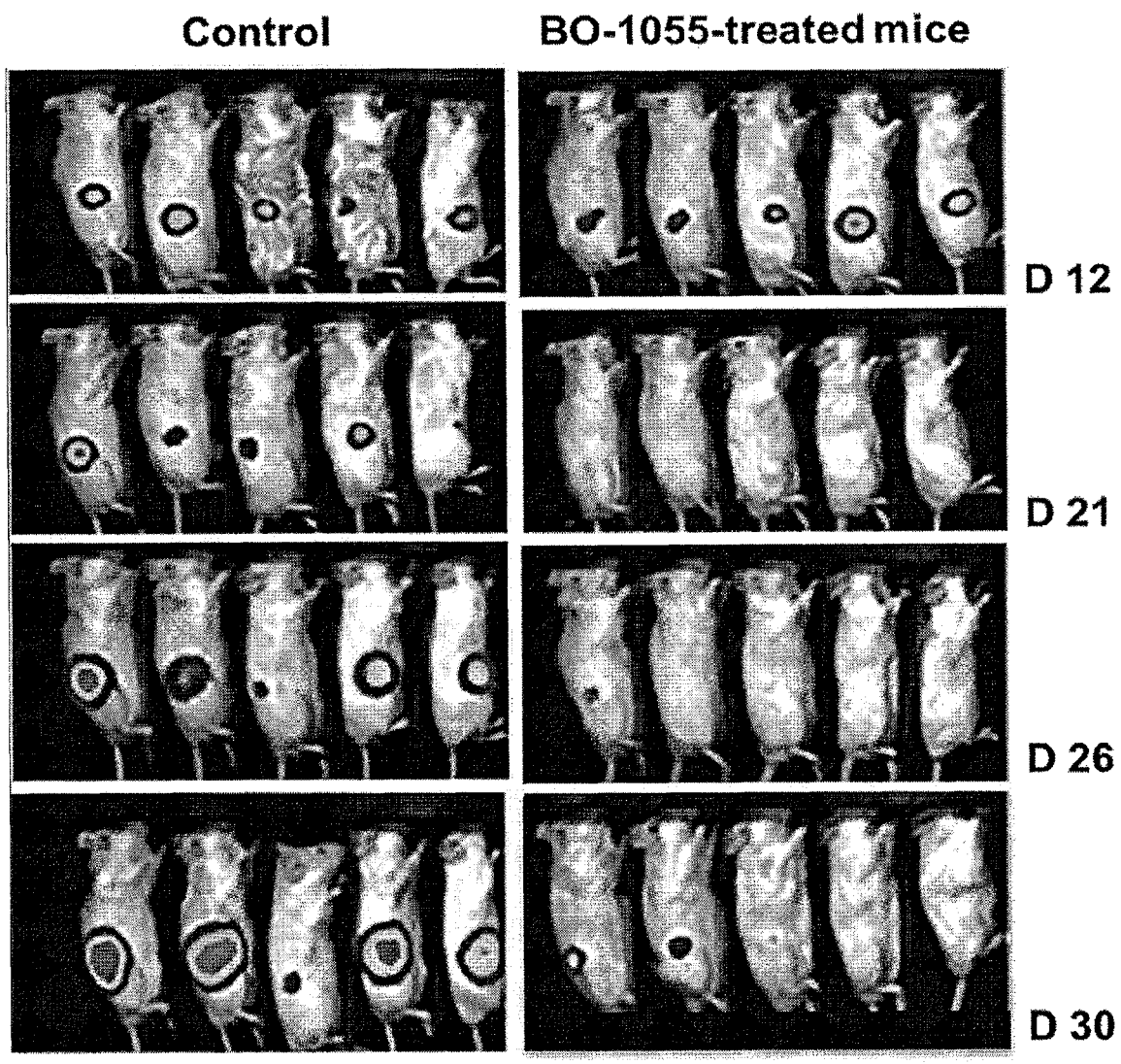
FIG. 20 shows eight bioimaging photograph panels of five mice each. The four panels on the left show mice which were only injected with GFP-Lu-SCLC H526 cells and control media; and the four panels on the right show mice which were injected with SCLC H526 cells and were further treated with ureidomustine.

FIG. 20 shows eight bioimaging photograph panels of five mice each. The four panels on the left show mice which were only injected with GFP-Lu-SCLC H526 cells and control media; and the four panels on the right show mice which were injected with SCLC H526 cells and were further treated with ureidomustine.

As can be seen in FIG. 20, progressive tumor growth was seen in 4/5 control mice from d12 to d30 (one mouse had engrafted tumor at baseline but did not show progressive tumor growth. In BO-1055-treated mice no tumor was detectable through d26 and at d30 3/5 treated mice were still tumor-free.

Figure 21:
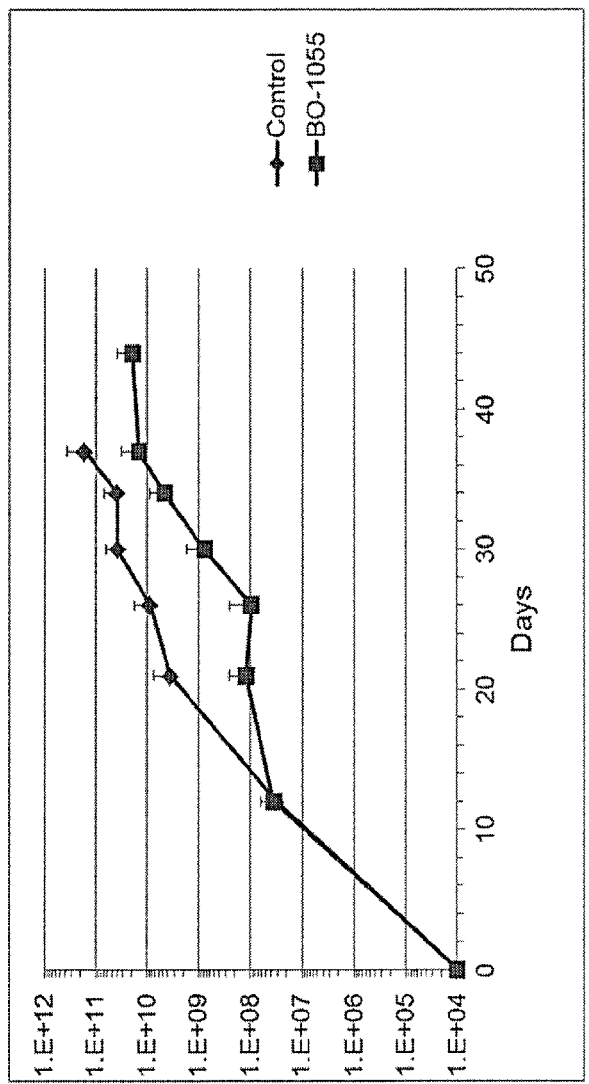
FIG. 21 shows a logarithmic chart of the growth of GFP-Lu-SCLC H526 cells in the mice depicted in FIG. 20.

The data was expressed as total photon emissions in FIG. 21 that shows between day 20 and 30 there was a two log difference in total photon emission between the treated and control mice.

(xii) In Vivo Studies of Nude Mice Bearing SCLC H526 Xenografts Treated with BO-1055

Figure 22A:
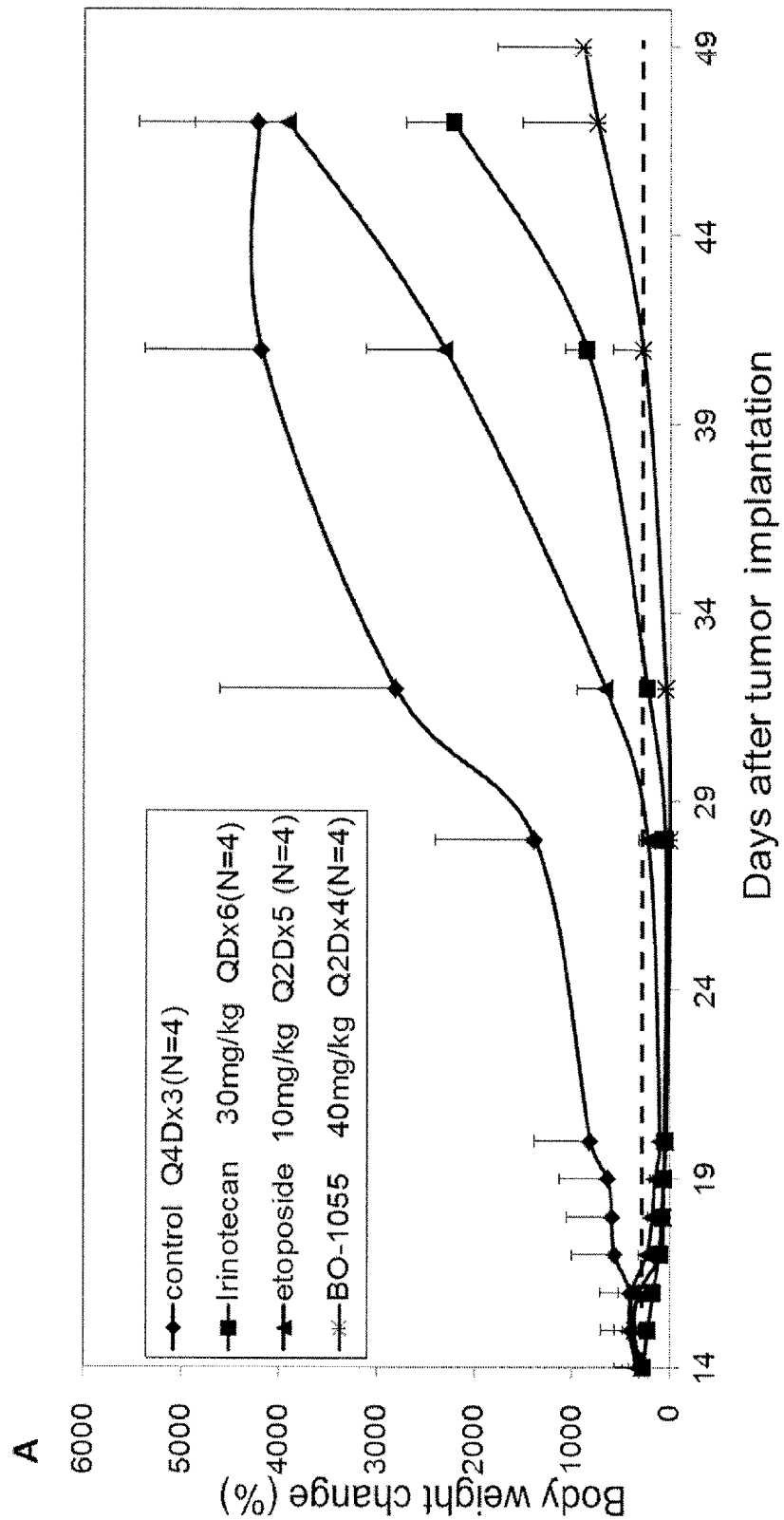
FIG. 22A is a chart of average tumor size vs days after tumor implantation in various mice bearing SCLC H526 xenografts (s.c.), after intravenous injection of ureidomustine or irinotecan or etoposide.
Figure 22B:
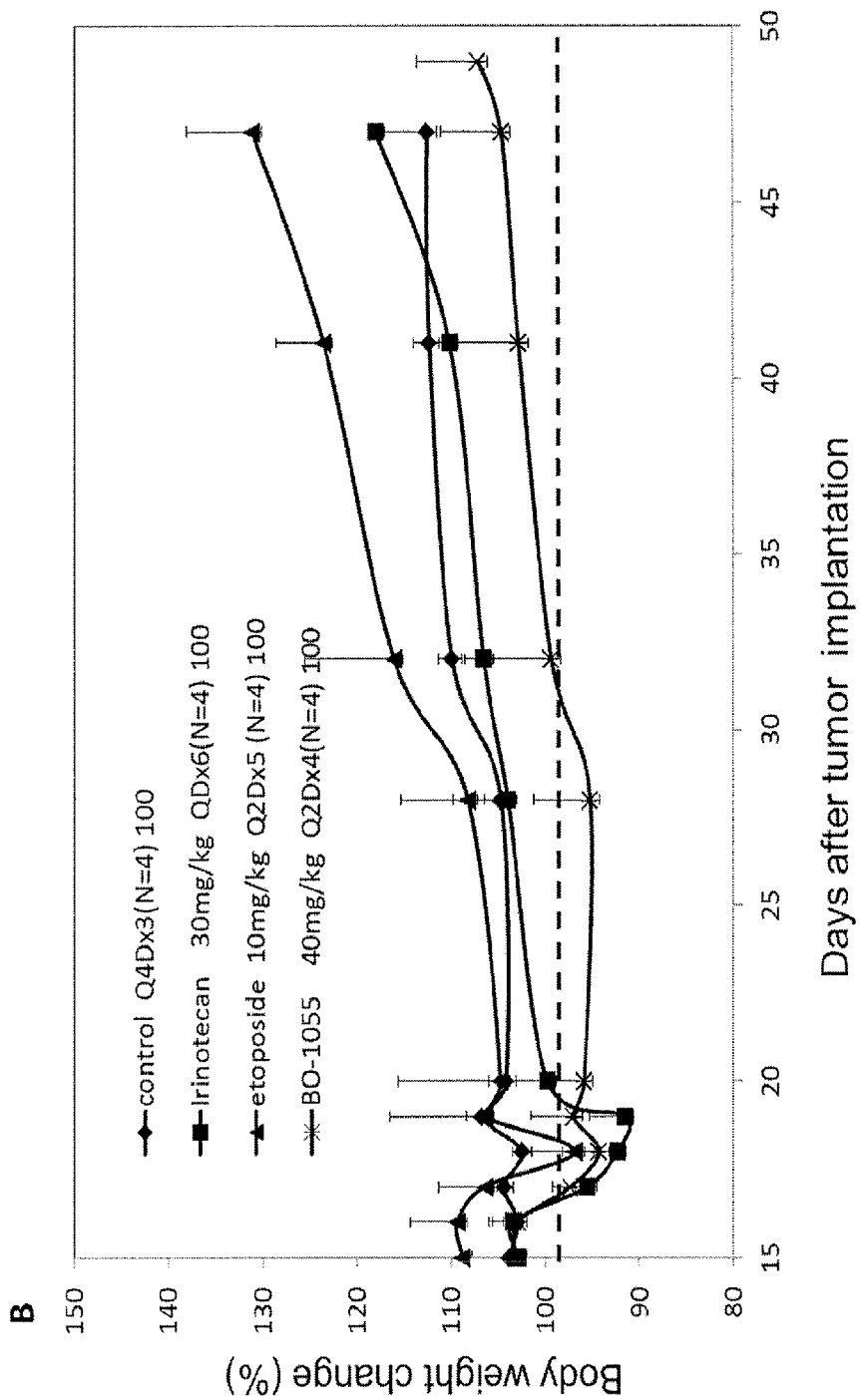
FIG. 22B is a chart of average body weight changes vs days after tumor implantation in the same mice.

The inventors also evaluated the therapeutic efficacy of BO-1055 in nude mice bearing SCLC H526 xenograft. Four mice were treated with BO-1055 with 40 mg/kg, via intravenous injection, once every two days for four times. Irinotecan (30 mg/kg, once every day for 6 times, iv injection, n=4) and etoposide (30 mg/kg, once every two days for 6 times, iv injection, n=4) were used as the positive control. As shown in FIGS. 22A and 22B, BO-1055 is more effective than Irinotecan or etoposide.

Mice bearing tumor were sacrificed when the tumor volume was greater than 2000 mm$^3$. The control and positive control mice were sacrificed on 47d; the BO-1055 treated mice (n=4): 3/4 complete remission (CR)-+on 28d, 2/4 CR on 32d; 1/4 CR on 77d.

Example 13C

Lymphoma

Lymphomas are tumors of the lymphatic system and are 3-4% of all cancers and the 7th most common form of cancer in adults and the 3rd most common in children. There were 566,000 cases worldwide in 2012 and 305,000 deaths.

There are dozens of subtypes of lymphoma, some are considered curable while others have a very poor prognosis. Therapeutic options involve some combination of chemotherapy, radiation therapy, targeted therapy and surgery.

A number of these subtypes are discussed below.

(i) Hodgkin Lymphoma (HL)

This form of lymphoma is marked by the presence of Reed-Sternberg cells. There are two major types of Hodgkin lymphoma, the most common is the Nodular sclerosis form found mostly in young adults. The second-most common form is the Mixed-cellularity subtype most common in men and more likely to be diagnosed at an advanced stage. The Epstein-Barr virus is involved in 70% of these cases.

(ii) Non-Hodgkin Lymphoma (NHL)

There were 70,800 new cases of NHL in the U.S. in 2014 and of these, 10% were T-cell lymphomas and 90% B-cell lymphomas. There are a number of subtypes of B-cell NHL with differing prognoses and therapeutic response.

(iii) Follicular Lymphoma

This is the second most common form of lymphoma in the United States and Europe with 14,160 new cases in 2014. It occurs in older adults, usually involves lymph nodes, bone marrow and spleen, associated with t(14;18) translocation overexpressing Bcl-2 It is most often indolent, and grows very slowly. There is no known cure; however, more than 85% of patients live for at least five years after diagnosis, and 50% live longer than 12 years. Drugs such as bendamustine (Treanda) and lenalidomide (Revlimid), usually in combination with rituximab, have been shown to be effective for this subtype and can be used as part of first-line treatment. Over time, follicular lymphoma may turn into DLBCL which then requires more aggressive treatment.

(iv) Primary Mediastinal B-Cell Lymphoma.

This lymphoma mainly affects people from their teenage years to their early 30s. Many patients are cured with a combination of chemotherapy and radiation therapy. However, even with this treatment, about 20 percent of patients have progressive disease.

(v) Peripheral T-Cell Lymphoma not Otherwise Specified

This is the most common T-cell lymphoma and usually presents as a mix of small to large CD3+ lymphoid cells with irregular nuclear contours. It can be further subdivided into several rare variants but all are often disseminated and generally aggressive tumors.

(vi) Mycosis Fungoides

This is the most common cutaneous lymphoid malignancy presenting with localized or more generalized skin lymphoid cell infiltration and is generally indolent. In a more aggressive variant, Sezary's disease, there is skin erythema and peripheral blood involvement. Overall survival at 5 years is 75%

(vii) Diffuse Large B-Cell Lymphoma (DLBCL)

This is the most common form of lymphoma. It comprises ~35% of NHL in North America and 60% of all aggressive cases. There were 21,240 new cases in the U.S. in 2014. DLBCL can be subdivided into those with a germinal center B-cell (GCB) origin and those with an activated B-cell (ABC) origin. DLBCL is an aggressive form of NHL that involves organs other than the lymph nodes about 40% of the time.

(viii) Establishment of a Panel of Lymphoma Cell Lines Incorporating Human DLBCL Cell Lines Representing ABC and GBC Subgroups; Human Mantle Cell Lymphoma Lines and a Murine B-Cell Lymphoma.

(a) Cell lines and methods: Diffuse large B-cell lymphoma (DLBCL) cell lines LY1, Ly8, Ly10, Ly18 were cultured in IMDM medium and Ly3, Ly19, SUDHL-4, SUDHL-6, Pfeifer, Farage, Toledo, Karpas-422, HBL1, U2932 were cultured in RPMI. Mantle cell lymphoma (MCL) cell lines JEKO-1, Mino, Granta-519, NECB-1, Z-138, REC-1 and HBL2 were cultured routinely in RPMI medium. All medium was supplemented with 10% FBS, 1% L-glutamine, 1% penicillin, and streptomycin. Cell lines were obtained from the American Type Culture Collection (ATCC, Manassas, Va., USA) or from MSKCC investigators after authenticated by STR profiling at GRCF DNA Services (Johns Hopkins University, Baltimore, Md.) using a Profiling Kit (PowerPlex 16HS).

(b) Spontaneous murine B-cell lymphoma. We have also maintained a CD19+B-cell lymphoma that arose spontaneously in a Nude mouse, by repeated passages in NSG mice following either intraperitoneal or subcutaneous injection plus Matrigel or by intravenous injection. This primary lymphoma is similar to the human DLBCL and was used to determine cytotoxicity of BO-compounds with treatment in vitro in the presence or absence of murine MS5 stromal cells that are necessary for long-term in vitro maintenance of the lymphoma cells.

(ix) Phenotype and Molecular Features of the Diffuse Large B-cell Lymphoma (DLBCL) Cell Lines.

As shown in Table 25, the twelve human Non-Hodgkin Lymphoma cell lines used to evaluate BO-1055 cytotoxicity were examples of DLBCL that could be further subdivided into subtypes based on derivation from germinal center B-cells (GCB) or activated B-cells (ABC). Eight of the lines had TP53 mutations and seven had the BCL2 t(14;18) translocation. This translocation is present in ~70% of follicular lymphomas and ~30% of diffuse large B-cell lymphomas. Other types of BCL2 gene rearrangement or amplification were found in two lines and three lines had wild type (wt) BCL2. The BCL6 gene was wild type in 5/10 lines, amplified in 3/10, translocated in one and deleted in one.

The BCL6 gene status was matched to the level of BCL6 protein produced by each cell line. Myc was amplified or rearranged in 4/12 lines.

Table 22 also shows the clinical status of the patient at the time the cells were obtained for cell line production. Five lines were obtained at the time of first diagnosis and seven at relapse. Cytogenetic studies of the lines showed that 3 had normal numbers of chromosomes, 5 were hyperdiploid and 3 were near tetraploid or hypertetraploid.

TABLE 22

Origin and molecular features of Diffuse Large B-Cell Lymphoma (DLBCL) cell lines of Germinal Center B-cell (GCB) subtype or Activated B-cell (ABC) subtype.

| Cell Line | DLBCL Subtype | Clinical Status | TP53 status | Ploidy | BCL2 status | BCL6 prot. | BCL6 gene | Myc status |
|---|---|---|---|---|---|---|---|---|
| Ly1 | GCB | Rel. | Mut. | 46-47, xy | t (14, 18) | +++ | Amp. | Amp, |
| Ly3 | ABC | Rel. | Wt | 72-75 xy | Amp | ++ | Amp. | Wt |
| Ly8 | GCB | Dx | Mut. | 46-48 x | t (14, 18) | + | Trans | Rea. |
| Ly10 | ABC | Dx | Wt | 46 xx | Wt | ++ | Wt | Wt |
| Ly18 | GCB | Dx | Mut. | 96-98 xxx | Rea | nd | Wt | Rea. |

TABLE 22-continued

Origin and molecular features of Diffuse Large B-Cell Lymphoma (DLBCL) cell lines of Germinal Center B-cell (GCB) subtype or Activated B-cell (ABC) subtype.

| Cell Line | DLBCL Subtype | Clinical Status | TP53 status | Ploidy | BCL2 status | BCL6 prot. | BCL6 gene | Myc status |
|---|---|---|---|---|---|---|---|---|
| Ly19 | GCB | Rel. | Mut. | nd | t (14, 18) | nd | Nd | Wt |
| SUDHL-4 | GCB | Dx | Mut. | 47-51 xxy | t (14, 18) | + | Amp. | Wt |
| SUDHL-6 | GCB | Dx | Wt | 42-48 x | t (14, 18) | ++ | Wt | Wt |
| Pfeiffer | GCB | Rel. | Mut. | 46 xy | t (14, 18) | +/− | Nd | Wt |
| Farage | GCB | Rel. | Mut. | 46 xx | Wt | ++ | Wt | Wt |
| Toledo | GCB | Rel. | nd | >2n xx | Wt | − | Del. | Wt |
| Karpas-422 | GCB | Rel. | Wt | 44-48 xx | t (14, 18) | ++ | Wt | Rea. |

Mut = mutated gene,
Wt—wild type gene,
Amp = amplified gene,
Rea = Rearrangement,
Del = deleted gene,
Trans = translocated,
Dx = at diagnosis,
Rel = at relapse,
nd = not determined.

(x) Cytotoxicity of BO-1055 on Lymphoma Cell Lines.

The in vitro cytotoxicity of BO-1055 was determined on: (a) sixteen human DLBCL cell lines, 12 of the GCB subgroup and 4 of the ABC subgroup: (b) seven human mantle cell lymphoma lines and (c) one primary murine B-cell lymphoma in the presence or absence of a supportive stromal monolayer (Table 23).

Based on 21-25 lines evaluated, the three lymphoma subgroups and the murine B-cell lymphoma did not diverge significantly in overall drug responsiveness.

TABLE 23

Comparison of the cytotoxicity (IC$_{50}$ µM) of BO-1055 screened against 24 lymphoma lines, including examples of human DLBCL subtypes GCB and ABC, Mantle Cell Lymphoma and a spontaneous murine B-cell lymphoma.

| Lymphoma B-Cell | DLBCL subtype GCB (mutations) | BO-1055 |
|---|---|---|
| Farage | p53mut.Myc,Bcl6,Bcl2cWt | 0.44 |
| Karpas-422 | p53wt t(14,18) BcI6 Wt,Myc Rear. | 5.85 |
| Ly1 (OCH-Ly1) | p53mut t(14,18) Myc, BcI6 amp. Stg IV | 3.86 |
| LY18 (OCH-Ly18) | p53mut.BcI2,Myc rearranged | 0.61 |
| LY19 (OCH-Ly19) | p53mut t(14,18) Myc wt | 0.29 |
| LY7 (OCH-Ly7) | p53mut | 5.06 |
| Ly8 (OCH-Ly8) | p53mut. t(14,18)BcI6 trans.Myc rear. | 0.22 |
| Pfeiffer | p53mut t(14,18 BcI6 +/−,Myc wt | 3.87 |
| SUDHL-4 | p53mut t(14,18),BcI6 amp.Myc wt | 1.95 |
| SUDHL-5 | t(14,18), | 4.14 |
| SUDHL-6 | p53wt t(14118).BcI6,Myc wt | 5.93 |
| Toledo | p53?Bcl2wt,BcI6 del.Myc wt | 8.95 |
| Lymphoma B-Cell | DLBCL subtypeABC (mutations) | BO-1055 |
| HBL1 Ly10 (OCH-Ly10) |  | 0.87 |
|  | p53wt BcI2/6wt Myc wt | 0.12 |
| Ly3 (OCH-Ly3) | p53wt BcI2/6 amp. | 3.50 |
| U2932 |  | 2.22 |
| Mantle Cell | t(11; 14) (q13;q32) | BO-1055 |
| Granta-519 | CD5-p53wt. CCND1+ | 5.50 |
| HBL2 | CD5+ p53 Mut | 0.16 |
| JEKO-1 | CD5+ p53WT BcI2+,CCND1+ | 0.27 |
| Mino | CD5+ p53 mut, BcI2+CCND1+ | 0.11 |
| NECB-1 | CD5 p53 del | 7.71 |
| REC-1 | CD5− p53 WT | 12.50 |
| Z-138 | CD5− p53 WT | 0.30 |
| Lymphoma B-cell | Murine | BO-1055 |
| Murine BCL | Spontaneous NSG CD19+ | 0.46 |
| Murine BCL | on irrad MS5 stroma | 0.80 |

Data showing IC$_{50}$ µM for BO-1055.

(xi) Comparison of Cytotoxicity of BO-1055 and 33 Chemotherapeutic Agents Including Pathway Targeting Agents, HSP90 and HSP70 Inhibitors, Proteasome Inhibitor, Cisplatin, Doxorubicin, and Bortezomib, Screened Against 40 Lymphoma Cell Lines.

The cytotoxicity (IC$_{50}$ µM) of BO-1055 was compared to that of a panel of anticancer drugs—compounds that including pathway targeting agents, HSP90 and HSP70 Inhibitors, proteasome inhibitors, cisplatin, doxorubicin, and bortezomib. These were evaluated for cytotoxicity against various lymphoma cell lines, including human DLBCL GBC and ABC subtypes, mantle cell lymphoma, as shown in Table 24.

This Table shows data (IC$_{50}$ µM) that is available on publically accessible site (Broad Institute, Sanger Institute) and data generated by Drs T. L. Su and Lee of Academica Sinica, Taiwan and Dr M. A. S. Moore and colleagues at MSKCC.

(a) Properties of compounds evaluated for cytotoxicity comparison with BO-1055 in Table 24.

ARN: ARN-231 ovarian cancer stem cell inhibitor (Moore M A unpublished).

TT46 HSP70 inhibitor (Kang et al 2014).

PUH71: HSP90 inhibitor (Ambati et al. 2014a, Jhaveri et al. 2014).
17-AAG/Tanespimycin: HSP90 inhibitor (Jhaveri et al. 2014).
Bort: Bortezomib/Velcade: Proteasome inhibitor.
Cisp: Cisplatin alkylating platinum drug. Doxo: Doxorubicin, an anthracycline antitumor antibiotic.
TK: TKI258, Dovitinib, an EGFR, FGFR1, PDGFRbeta, VEGFR-1, KDR inhibitor. Phase3 Novartis.
AEW:AEW541, an IGFR inhibitor, preclinical, Novartis.
SOR: Sorafenib/Nexavar, Flt3, c-KIT, PDGFRβ, RET, Raf kinase B, Raf kinase C, VEGFR-1, KDR, FLT4 inhibitor, FDA approve 2005. Bayer
TOPO: Topotecan/Hycamtin, a topoisomerase 1 inhibitor. FDA approved 1996. GlaxoSmithKline.

(b) Cytotoxicity of various compounds described in (xiii) (a) on a panel of various human lymphomas cell lines representing different tumor subgroups Ten lines were highly sensitive ($IC_{50}$ 0.11-0.87 μM), 6 lines were moderately sensitive ($IC_{50}$ 1.95-4.14 μM), 6 lines were moderately resistant ($IC_{50}$ 5.06-8.95 μM) and only 1 line was highly resistant ($IC_{50}$ 12.5 μM), Of 27 lines screened with BO-1055, 11 lines were highly sensitive (defined as $IC_{50} <1$ μM) with $IC_{50}$ 0.12-0.84 μM. 14 lines were moderately sensitive (defined as $IC_{50}$ 1.00-4.99 μM) with $IC_{50}$ from 1.08-4.90 μM (TI 2.04-9.03). Two lines were resistant ($IC_{50} >10.0$ μM). Evaluation of BO-1055 cytotoxicity upon sub-classification of the DLBCL lines into ABC and GBC types did not reveal significant differences. In the ABC group of 4 cell lines one line was very sensitive ($IC_{50}<1.0$ μM) and three were moderately sensitive ($IC_{50}$ 1.0-4.9 μM).

In the GBC group of 10 lines, 4 were very sensitive, 4 were moderately sensitive, 1 was moderately resistant and 1 was highly resistant to BO-1055. TP53 status did not seem to determine BO-1055 sensitivity since eight lines with TP53 mutations had a range of $IC_{50}$ values (0.29-4.90 μM), as did 4 TP53 wild type lines ($IC_{50}$ 0.12-7.02 μM). BCL2 mutation status likewise did not determine BO-1055 toxicity since the lines with WT Bcl2 had an $IC_{50}$ range of 0.12 to >10.0 μM and the mutated/rearranged/amplified BCL2 lines had a similar range ($IC_{50}$ 0.29-4.9 μM).

TABLE 24

The cytotoxicity ($IC_{50}$ μM) of B0-1055 compared to various anticancer agents including pathway targeting agents, HSP90 and HSP70 Inhibitors, pro teasome inhibitor, cisplatin, doxorubicin, bortezomib, screened against various lymphoma cell lines including human DLBCL GBC and ABC subtypes, mantle cell lymphoma.

| Lymphoma DLBCL(GCB) | BO-1055 | ARN | TT46 | PUH 71 | 17-AAG | Bort | Cisp | Doxo | TK | AEW | SOR | TOPO |
|---|---|---|---|---|---|---|---|---|---|---|---|---|
| Farage | 0.44 | nd | nd | nd | nd | nd | >10.0 | 0.273 | nd | Nd | nd | nd |
| Karpas-422 | 5.85 | 1.32 | 0.22 | 0.45 | nd | 0.019 | >10.0 | 0.211 | nd | Nd | nd | nd |
| LY I | 3.86 | 0.31 | 0.20 | 0.26 | nd | 0.005 | >10.0 | 0.011 | nd | Nd | nd | nd |
| LY8 | 0.22 | nd | nd | nd | nd | nd | >10.0 | 0.093 | nd | Nd | nd | nd |
| LY18 | 0.61 | nd | 0.22 | 0.27 | nd | 0.010 | >10.0 | 0.097 | nd | Nd | nd | nd |
| LY19 | 0.29 | nd | nd | nd | nd | nd | >10.0 | 0.121 | nd | Nd | nd | nd |
| LY7 | 5.06 | nd | nd | nd | nd | nd | nd | nd | nd | Nd | nd | nd |
| LY8 | 0.22 | nd | 0.95 | 0.81 | nd | 0.078 | >10.0 | 0.084 | 3.35 | 4.09 | >8.0 | 0.19 |
| Pfeiffer | 3.87 | 0.90 | 0.08 | 0.41 | 0.45 | 0.004 | >10.0 | 0.061 | 2.38 | 3.75 | 4.57 | 0.06 |
| SUDHL-4 | 1.95 | 0.50 | 0.19 | 0.20 | 0.05 | 0.003 | >20.0 | 0.206 | 4.19 | 0.40 | 5.62 | 0.12 |
| SUDHL-5 | 4.14 | nd | 0.40 | 0.41 | nd | 0.018 | nd | 0.912 | nd | Nd | nd | nd |
| SUDHL-6 | 5.93 | 0.38 | 0.68 | 0.05 | nd | 0.001 | >10.0 | 0.195 | 0.21 | 0.18 | >8.0 | 0.11 |
| Toledo | 8.95 | >10.0 | >10.0 | 2.66 | 0.37 | 0.108 | >10.0 | >10.0 | nd | Nd | nd | nd |

| Lymphoma DLBCL(ABC) | BO-1055 | ARN | TT46 | PUH 71 | 17-AAG | Bort | Cisp | Doxo | TK | AEW | SOR | TOPO |
|---|---|---|---|---|---|---|---|---|---|---|---|---|
| HBLI | 0.87 | 0.28 | 0.16 | 1.67 | 1.23 | 0.004 | >10.0 | 0.211 | nd | Nd | nd | nd |
| LY10 | 0.12 | nd | nd | 0.14 | nd | nd | >10.0 | 0.084 | 28.0 | 28.0 | 28.0 | 2.60 |
| LY3 | 3.50 | 0.85 | 1.80 | 2.78 | nd | 0.021 | >10.0 | 0.023 | nd | Nd | nd | nd |
| U2932 | 2.22 | 1.35 | 0.25 | 0.49 | 0.03 | 0.005 | >20.0 | 0.050 | nd | Nd | nd | nd |

| Lymphoma Murine B | BO-1055 | ARN | TT46 | PUH 71 | 17-AAG | Bort | Doxo Cisp | TK Doxo | AEW TK | SOR AEW | TOPO SOR | TOPO |
|---|---|---|---|---|---|---|---|---|---|---|---|---|
| CD19+ | 0.46 | nd | nd | 0.24 | nd | 0.006 | nd | 0.124 | nd | Nd | nd | nd |
| On stroma | 0.80 | 0.98 | 0.14 | nd | nd | nd | >10 | 0.001 | nd | Nd | nd | nd |

| Lymphoma Mantle Cell | BO-1055 | ARN | TT46 | PUH 71 | 17-AAG | Bort | Doxo Cisp | TK Doxo | AEW TK | SOR AEW | TOPO SOR | TOPO |
|---|---|---|---|---|---|---|---|---|---|---|---|---|
| Granta-519 | 5.50 | nd | 0.25 | 1.22 | nd | 0.008 | >10.0 | 0.41 | 3.40 | 28.0 | 28.0 | 0.05 |
| HBL2 | 0.16 | nd | nd | nd | nd | nd | >10.0 | 0.03 | nd | Nd | nd | nd |
| JEKO-1 | 0.27 | nd | 0.25 | 0.26 | nd | nd | 12.5 | 0.04 | nd | Nd | nd | nd |
| Mino | 0.11 | nd | 0.22 | 0.26 | nd | 0.042 | >10.0 | 0.07 | 1.60 | 5.57 | 28.0 | 0.05 |
| NECB-1 | 7.71 | nd | 1.55 | 1.66 | nd | 0.143 | >10.0 | 1.23 | nd | Nd | nd | nd |
| REC-1 | 12.5 | nd | nd | nd | nd | nd | >10.0 | 0.05 | nd | Nd | nd | nd |
| Z-138 | 0.30 | nd | nd | 0.06 | nd | 0.008 | >10.0 | 0.34 | nd | Nd | nd | nd |

| Lymphoma DLBCL (GCB) | | | | | | | | | | | | |
|---|---|---|---|---|---|---|---|---|---|---|---|---|
| Karpas-422 | 5.85 | 1.32 | 0.22 | 1.52 | nd | 0.066 | >10.0 | 0.56 | nd | Nd | nd | nd |
| LY1 | 3.86 | 0.31 | 0.20 | 0.308 | nd | 0.005 | >10.0 | 0.11 | nd | Nd | nd | nd |

TABLE 24-continued

The cytotoxicity (IC$_{50}$ µM) of B0-1055 compared to various anticancer
agents including pathway targeting agents, HSP90 and HSP70 Inhibitors,
pro teasome inhibitor, cisplatin, doxorubicin, bortezomib, screened against
various lymphoma cell lines including human DLBCL GBC and ABC subtypes,
mantle cell lymphoma.

| Pfeiffer | 3.87 | 0.90 | 0.08 | 0.108 | 0.45 | 0.004 | >10.0 | 0.061 | 2.38 | 3.75 | 4.57 | 0.06 |
| SU-DHL-4 | 1.95 | 0.50 | 0.19 | 0.20 | 0.051 | 0.003 | >20.0 | 0.21 | 4.19 | 0.40 | 5.62 | 0.11 | nd=not determined*Spontaneous B-cell lymphoma that originated in a NOD-SCID-IL2Rγnull mouse. Cytotoxicity determined on lymphoma cells with no stromal support. On co-culture with irradiated MS5 stroma cytotoxicity (IC$_{50}$) of BO-1055 was 0.80 µM and of Cisplatin was >10.0 µM *Data on BO-1055 generated by Dr M.A.S Moore at MSKCC and Dr T.L. Su at Academia Sinica. Data on ARN generated by Dr M.A.S. Moore and colleagues at MSKCC. Data on TT46 and PUH71 from Drs G. Chinosis, M.A.S. Moore and E Caldas at MSKCC, Data on isofludalone, synthesized by Dr S Danishefsky and colleagues at MSKCC, was generated by Dr MAS Moore and colleagues at MSKCC. Data on SAHA, first developed at MSKCC, was from multiple sources.

(xii) Cytotoxicity of Combinations of BO-1055 and Doxorubicin on DLBCL (ABC Subtype) Cell Line OCY-LY3.

Combination indices (CIs) were calculated using the Chou-Talalay method (Chou and Talaley 1984) which stipulates that a CI>1 indicates antagonism, a CI=1 indicates an additive effect, and a CI<1 indicates synergy. Multiple studies have established that Chou-Talalay analysis is applicable to drug-drug interactions (Chou 2010). OCY-LY3 cells were incubated for 72 h with increasing concentrations of drugs (8 fold serial dilutions from 20 uM-0.02 uM) as single drug or drug combination (Cte corresponds to IC$_{50}$ for respective drug). After treatment, the cells were assessed by Alamar Blue.

FIG. 23A: Proliferation inhibition curve and IC$_{50}$ obtained by GraphPad Prism. Figure Cytotoxicity of BO-1055 or Doxorubicin as monotherapy or in combination on the DLBCL (ABC subtype) cell line OCI-LY3.

FIG. 23B: Proliferation inhibition curve and IC$_{50}$ obtained by GraphPad Prism.C. Normalized. Fa-Ci Plot: Effect oriented.

Figure 23C:
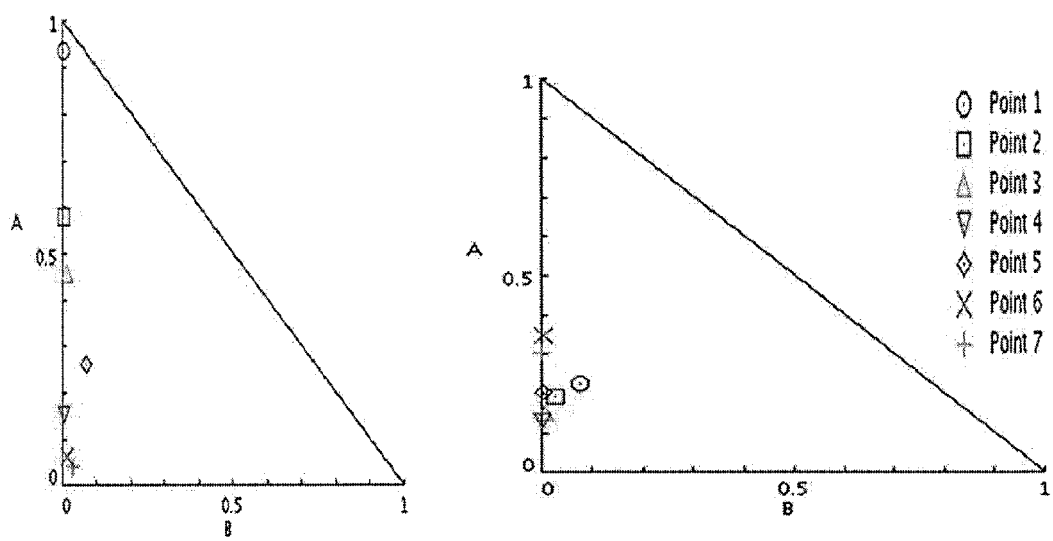
FIG. 23C depicts an isobologram obtained by GraphPad Prism on the same cells; the panel on the left depicts B01055 Cte+DOXO Var.; while the panel on the right depicts DOXO Var+B01055 Cte.

FIG. 23C: Isobologram for combination of BO-1055 and Doxorubicin: Left: B01055 Cte+DOXO Var. Right: DOXO Var+B01055 Cte (Chou 2010). Dose oriented-where CI<1=Synergism; CI=1=Additive; CI>1=Antagonism. Values were calculated by CompuSyn software (Chou and Talalay 1984, Chou 2010).

Isobologram:

(xiii) Cytotoxicity of Combinations of BO-1055 and HSP Inhibitors (PUH71, TT46), Bortezomib, and Doxorubicin Determined on DLBCL (GBC) Cell Lines.

Drugs were titrated at 7-9 different concentrations in combination with BO-1055 at its IC$_{50}$ or drugs were added at a dose corresponding to the IC$_{50}$ of each and combined with 7-9 different concentrations of BO-1055. The target cell lines were 12 human DLBCL cell lines of the GBC subgroup.

The results of the combination studies on DLBCL (GBC) cell lines using a combination of: 1) BO-1055 and the HSP90 inhibitor PUH71; and 2) BO-1055 and HSP70 inhibitor TT46 are shown in Table 25 which gives the IC$_{50}$ data for each drug in single agent treatment and the combination index for the combined therapy, wherein one drug is used at its IC$_{50}$ µM, and the other drug is titrated over 8 serial dilutions (Chou 2010).

In Comb-1, BO-1055 is a variable and the HSP inhibitors are used at their IC$_{50}$ µM dose. In Comb-2,PUH71 or TT46 is a variable, and BO-1055 is used at its IC$_{50}$ µM dose. The upper section of Table 25 presents data for PUH71, while the bottom section of Table 25 presents data for TT46.

Of the 11 evaluable data sets with BO-1055 and PUH71, PUH71 was synergistic with BO-1055 in both combinations against Z-138 but in contrast, TT46 was antagonistic in both combinations against the same cell line. PUH71 was dually antagonistic to GRANTA whereas TT46 was synergistic in combo-1 and antagonistic in combo-2 against GRANTA. Both HSP inhibitors were antagonistic against REC-1 in both combinations with BO-1055. PUH71 was dually synergistic with BO-1055 against MINO whereas TT46 was synergistic with BO-1055 against this cell line only in combo-1 and antagonistic in combo-2. Both PUH71 and TT46 were synergistic with BO-1055 against NECB1 in combo-1 and antagonistic in combo-2.

TABLE 25

The potential additive or synergistic cytotoxicities of B0-1055, and of
PUH71, TT46, bortezomib, and doxorubicin determined on DLBCL (GBC) cell lines

| Lines DLBCL (GCB) | BO-1055 IC$_{50}$ (µM) | PUH71 IC$_{50}$ (µM) | Comb-1 BO-1055 Var) PUH71 Cte) | Comb-2 PUH71 Var) BO-1055 Cte) | CI values Fa = 0.5 Comb-1 Comb-2 | Effect Comb-1 Comb-2 |
|---|---|---|---|---|---|---|
| OCY-LY1 | 3.186 | 0.208 | Complete Effect | 0.206 | 0.223 0.971 | Synergistic Additive |
| OCY-LY7 | 5.061 | 0.391 | 5.124 | 0.387 | 1.105 1.542 | Antagonistic Antagonistic |
| OCI-LY8 | 0.224 | 0.814 | 0.029 | 0.273 | 0.602 0.993 | Synergistic Additive |
| OCI-LY18 | 0.608 | 0.274 | 0.586 | 0.167 | 1.341 0.067 | Antagonistic Synergistic |
| OCI-LY19 | 0.287 | 0.221 | — | — | — | — |

TABLE 25-continued

The potential additive or synergistic cytotoxicities of BO-1055, and of PUH71, TT46, bortezomib, and doxorubicin determined on DLBCL (GBC) cell lines

| | | | | | | |
|---|---|---|---|---|---|---|
| SUDHL4 | 1.954 | 0.379 | 0.580 | 0.232 | 0.932 | Additive |
| | | | | | 0.976 | Additive |
| SUDHL5 | 4.137 | 0.336 | Complete Effect | Complete Effect | 0.422 | Synergistic |
| | | | | | 0.320 | Synergistic |
| SUDHL6 | 5.931 | 0.672 | 5.141 | 0.487 | 1.214 | Antagonistic |
| | | | | | 0.916 | Additive |
| FARAGE | 0.444 | 0.785 | 1.840 | 1.221 | 5.632 | Antagonistic |
| | | | | | 3.218 | Antagonistic |
| PFEIFER | 3.874 | 0.335 | 2.580 | 0.372 | 1.234 | Antagonistic |
| | | | | | 1.121 | Antagonistic |
| TOLEDO | 8.950 | 10.92 | 9.901 | 12.569 | 4.327 | Antagonistic |
| | | | | | 5.002 | Antagonistic |
| KARPAS-422 | 5.847 | 1.520 | 2.467 | 0.781 | 0.292 | Synergistic |
| | | | | | 0.193 | Synergistic |

| DLBCL Lines (GCB) | BO-1055 IC$_{50}$ (µM) | TT46 IC$_{50}$ (µM) | Comb-1 BO-1055 (Var) TT46 (Cte) | Comb-2 TT46 (Var) BO-1055 (Cte) | CI (Fa = 0.5) Comb-1 Comb-2 | Effect Comb-1 Comb-2 |
|---|---|---|---|---|---|---|
| OCY-LY1 | 3.091 | 0.199 | Complete Effect | 0.277 | 0.235 | Synergistic |
| | | | | | 1.156 | Antagonistic |
| OCY-LY7 | 5.016 | 1.697 | 5.448 | 1.726 | 5.391 | Antagonistic |
| | | | | | 1.297 | Antagonistic |
| OCI-LY8 | 0.394 | 0.478 | 0.174 | 0.482 | 0.795 | Synergistic |
| | | | | | 2.491 | Antagonistic |
| OCI-LY18 | 0.398 | 0.220 | 0.450 | 0.118 | 1.631 | Antagonistic |
| | | | | | 0.189 | Synergistic |
| OCI-LY19 | 0.287 | 0.217 | — | — | — | — |
| SUDHL4 | 1.639 | 0.124 | 2.016 | 0.230 | 4.693 | Antagonistic |
| | | | | | 4.324 | Antagonistic |
| SUDHL5 | 3.945 | 0.402 | Complete Effect | Complete Effect | 0.126 | Synergistic |
| | | | | | 0.215 | Synergistic |
| SUDHL6 | 3.241 | 0.682 | 3.248 | 0.510 | 2.284 | Antagonistic |
| | | | | | 3.234 | Antagonistic |
| FARAGE | 0.978 | 1.479 | Complete Effect | Complete Effect | 0.344 | Synergistic |
| | | | | | 0.231 | Synergistic |
| PFEIFER | 4.783 | 0.054 | 4.521 | 0.100 | 2.456 | Antagonistic |
| | | | | | 1.038 | Antagonistic |
| TOLEDO | 7.821 | 25.00 | 12.863 | 24.660 | 8.087 | Antagonistic |
| | | | | | 2.345 | Antagonistic |
| KARPAS-422 | 6.989 | 0.215 | 1.169 | 0.125 | 0.360 | Synergistic |
| | | | | | 0.874 | Synergistic |

(xiv) Mantle Cell Lymphoma (MCL)

MCL is one of the rarest of the non-Hodgkin lymphomas (NHLs), comprising about 6% of NHL cases (4960 new cases in 2014). It most often appears in people older than 60 and is much more common in men than women by a ratio of 4 to 1. There are ~15,000 patients with MLC presently in the U.S.

It results from a malignant transformation of a CD5 positive antigen-naive pre-germinal center B-cell within the mantle zone that surrounds the normal lymph node germinal center follicles. In humans, the CD5 gene is located on the long arm of chromosome 11. CD5 serves to mitigate activating signals from the BCR so that the B-1 cells can only be activated by very strong stimuli (such as bacterial proteins) and not by normal tissue proteins. The MCL cells can metastasize to other lymph nodes or tissues, such as the marrow, liver and gastrointestinal tract. MCL is identified by overexpression of the cyclin D1 protein due to a translocation at t(11;14)(q13;q32). Additional genetic abnormalities involving the p53 pathway, are important for disease development and progression (see Table 25). MCL is difficult to treat and seldom considered cured. Median survival times were about 3 years, but are now estimated as approaching 6 years for new patients.

(xv) Cytotoxicity of BO-1055, Cyclophosphamide, Doxorubicin, Paclitaxel and Panobinostat on Mantle Cell Lymphoma Cell Lines As shown in Table 26, the mean IC$_{50}$±SD (µM) values of BO-1055 on various MCL cell lines were as follows:
JEKO-1 (0.266±0.27),
Z-138 (0.182±0.15),
HBL2 (0.161±0.34).

The inventors' results indicated that BO-1055 has a significant therapeutic window (50-100-fold) between its toxicity against human B-cell lymphomas and various normal human cell types. Treatment with BO-1055 resulted in accumulation of cells in S-phase and up-regulation of proteins involved in DNA repair [MRE11, p-P95/NBS1 (ser343), RAD50, p-ATR (ser428)] while Bcl-6, an important B-cell lymphoma biomarker, was down-regulated.

TABLE 26

Cytotoxicity (IC$_{50}$ µM) of BO-1055 on a panel of 7 human Mantle Cell Lymphoma cell lines. For comparison, cytotoxicity data is shown for doxorubicin (DNA intercalating anthracycline), paclitaxel (microtubule binding drug), cisplatin (alkylating platinum drug), and panobinostat (HDAC inhibitor).

| Mantle Cell Lymphoma | Mutations and markers | BO-1055 | Doxorubicin | Paclitaxel | Cisplatin | Panobinostat |
|---|---|---|---|---|---|---|
| Granta-519 | CD5− TP53wt. CyclinD1 amp. | 1.450 | 0.412 | 0.049 | >10.0 | 0.041 |
| HBL2 | CD5+ TP53 Mut | 0.161 | 0.028 | 0.016 | >10.0 | 0.013 |
| JEKO-1 | CD5+TP53 wt, Bcl2+, CyclinD1 | 0.266 | 0.035 | 0.017 | 12.5 | 0.210 |
| Mino | CD5+TP53mut, Bcl2+ CyclinD1 amp. | 0.583 | 0.065 | 0.025 | >10.0 | 0.291 |
| NECB-1 | CD5+ TP53 del | 8.410 | 0.163 | 0.064 | >10.0 | 0.020 |
| REC-1 | CD5− TP53 WT | >10.0 | 0.051 | 0.021 | >10.0 | 0.060 |
| Z-138 | CD5− TP53 WT | 0.182 | 0.033 | 0.012 | >10.0 | Nd |

(xvi) Measurement of the Therapeutic Window of BO-1055, Four Alkylating Drugs and Four Other Chemotherapeutic Agents on the MCL Line JEKO-1 Compared with Five Normal Tissues.

The Therapeutic Window (TW) was calculated from the IC$_{50}$ data presented in Table 26 that shows the 72 hr cytotoxicity (IC$_{50}$ uM) obtained with eleven compounds against a panel of benign tissues and the MCL cell line JEKO-1.

Table 27 shows the calculated therapeutic window for each compound. The upper part of Table 27 shows the IC$_{50}$ µM values for the ten compounds against the five normal human tissues and the MCL cell line JEKO-1. The lower part of the table expresses the data as the fold difference of the IC$_{50}$ values between the benign tissues relative to the IC$_{50}$ on Jeko-1.

BO-1055 has the best TW of all the drugs screened when normal hematopoietic cell toxicity is used as a determinant of potential dose limiting toxicity. The TW comparing the MCL data to the non-hematopoietic normal tissues further supports the position of BO-1055 as a highly active antineoplastic drug with remarkable selectivity and minimal damage to normal tissues at a drug dose that is highly toxic to malignant cells. The TW of BO-1055 observed when comparing other benign tissues to the MCL lines is also excellent due to lack of significant toxicity to normal epithelium, endothelium, and mesenchymal stroma.

There was a lack of a therapeutic window with the alkylating drugs 4-HC, Bendamustine and Cisplatin as well as with Etoposide, HSP90 inhibitor PU-H71 and Topoisomerase inhibitor SN38 due to the toxicity of these drugs to normal hematopoietic progenitor cells.

IC$_{50}$ (µM) was determined on cord blood hematopoietic progenitors (CD34+ cells, CFC), endothelium (HUVEC), bone marrow mesenchymal stem cells (huMSC), human hTERT immortalized epithelium of lung bronchus (Bci-NSI) and Fallopian tube (FTEC).

TABLE 27

Measurement of the Therapeutic Window (TW) of BO-1055 on the MCL line JEKO-1 compared to the TW for doxorubicin, etoposide, PUH71, SN-38, vincristine, and four alkylating drugs.

| 1. Compound | CD34 | HUVEC | HuMSC | Bci-NSI | FTEC | JEKO-1 |
|---|---|---|---|---|---|---|
| | | | IC$_{50}$ (µM) | | | |
| BO-1055 | 15.00 | 50.00 | 20.00 | 40.00 | 80.00 | 0.27 |
| 4-HC | 2.01 | 40.50 | 40.50 | 18.00 | 12.50 | 10.00 |
| Bendamustine | 10.00 | 150.00 | 300.00 | 150.00 | 400.00 | 6.25 |
| Melphalan | 7.00 | 320.00 | 160.00 | nd | 120.00 | 1.10 |
| Cisplatin | 6.00 | 50.00 | 20.00 | 30.00 | 100.00 | 12.50 |
| Doxorubicin | 0.20 | 0.35 | 0.45 | 0.50 | 6.25 | 0.05 |
| Etoposide | 0.09 | 0.35 | 70.20 | 0.50 | 200.00 | 0.78 |
| PUH71 | 0.05 | 0.35 | 0.63 | 1.50 | 80.00 | 0.31 |
| SN-38 | 7.00 | 400.00 | 200.00 | 500.00 | 2,000.0 | 0.80 |
| Vincristine | 2.34 | 0.25 | 6.30 | 200.00 | 250.00 | 0.39 |

| 2. Compound | fold difference of the IC$_{50}$ values between the benign tissues relative to the IC$_{50}$ on Jeko-1 | | | | | |
|---|---|---|---|---|---|---|
| BO-1055 | 30.00 | 185.18 | 74.07 | 148.15 | 296.29 | 1.00 |
| 4-HC | 0.20 | 40.50 | 4.05 | 1.80 | 1.25 | 1.00 |
| Bendamustine | 1.60 | 150.00 | 48.00 | 24.00 | 64.00 | 1.00 |
| Melphalan | 6.36 | 290.90 | 145.45 | nd | 290.90 | 1.00 |
| Cisplatin | 0.48 | 50.00 | 1.60 | 2.40 | 8.00 | 1.00 |
| Doxorubicin | 4.00 | 0.35 | 9.00 | 10.00 | 125.00 | 1.00 |
| Etoposide | 0.12 | 0.35 | 90.00 | 0.64 | 256.41 | 1.00 |
| PUH71 | 0.15 | 0.35 | 2.03 | 4.84 | 258.06 | 1.00 |

TABLE 27-continued

Measurement of the Therapeutic Window (TW) of BO-1055 on the MCL line JEKO-1 compared to the TW for doxorubicin, etoposide, PUH71, SN-38, vincristine, and four alkylating drugs.

|  | CD34 | HUVEC | HuMSC | Bci-NSI | FTEC | JEKO-1 |
|---|---|---|---|---|---|---|
| SN-38 | 8.75 | 400.00 | 250.00 | 625.00 | 2,500.0 | 1.00 |
| Vincristine | 6.00 | 0.25 | 16.15 | 512.82 | 641.03 | 1.00 |

The data shown in Table 27 (lower panel) identifies a therapeutic window (TW) between the drug dose that is toxic to the malignant cells but not to the normal cells tested. This ranged from 30-296 fold for BO-1055 which was the least myelotoxic of the 11 drugs that were screened.

4-HC, the active metabolite of cyclophosphamide, was also highly toxic to CD34+ cells and to normal epithelial and mesenchymal cells.

Bendamustine and Melphalan had high TW values against normal epithelium, endothelium and mesenchyme but only a limited window when evaluated against CD34+ cells (1.60-6.36 fold).

Cisplatin had a limited window (1.6-8.0) on epithelium and mesenchyme, a modest window on endothelium (50 fold) but was significantly limited by hematopoietic toxicity.

The topoisomerase II inhibitor Etoposide is also limited by high toxicity to CD34+ cells, as confirmed by its documented bone marrow suppressive side effects when used in chemotherapy of cancers such as Kaposi's sarcoma, Ewing's sarcoma, lung cancer, testicular cancer, lymphoma, myeloid leukemias, and glioblastoma multiforme (Hande 1998). It has also been used in a conditioning regimen prior to a bone marrow or blood stem cell transplant.

SN-38 is the active metabolite of irinotecan, a semisynthetic analogue of the natural alkaloid camptothecin and is a potent topoisomerase 1 inhibitor (1000 times more active than irinotecan itself). In vitro cytotoxicity assays show that the potency of SN-38 relative to irinotecan varies from 2- to 2000-fold (Pommier et al. 2010). The TW for SN-38 is 250-2,500 for non-hematopoietc tissues but is only 8.75 on CD34+ cells which is in agreement with the observation that the SN-38 metabolite is responsible for causing the symptoms of diarrhea, myelosuppression and extreme immunosuppression experienced by ~25% of the patients administered irinotecan.

The TW determinations for the HSP90 inhibitor PUH71 suggest the possibility of hematopoietic and vascular endothelial toxicity issues, although the latter may be a positive feature if it can selectively inhibit tumor neoangiogenesis.

The vinca alkaloid Vincristine is a tubulin-binding drug that inhibits assembly of microtubule structures and blocks metaphase replication. It is used to treat non-Hodgkin's lymphoma as part of the CHOP chemotherapy regimen, and for Hodgkin's lymphoma as part of MOPP, COPP and BEACOPP. It has also been used to treat multiple myeloma, rhabdomyosarcoma, neuroblastoma, and Wilm's tumor. It is also used to induce remission in ALL with dexamethasone and L-asparaginase, and in combination with prednisone to treat childhood leukemia. It has been used as an immunosuppressant in treating chronic idiopathic thrombocytopenia purpura. The TW on both hematopoietic cells and endothelial cells is suggestive of a myelosupressive and vascular damaging potential of the drug. The main side effects are chemotherapy-induced peripheral neuropathy that can be progressive and irreversible. Alopecia occurs in 20-75% of treated patients and it is also myelosuppressive and induces leukopenia and thrombocytopenia.

(xvii) Drug Combination Cytotoxicity Studies with BO-1055 and Bortezomib, Doxorubicin, HSP90- and HSP-70 Inhibitors on Mantle Cell Lymphoma Cell Lines.

The possible additive or synergistic cytotoxic actions of combinations of BO-1055 with bortezomib/velcade, doxorubicin, and heat shock protein inhibitors PUH71 (HSP90 inhibitor) and TT46 (HSP70 inhibitor) were determined against a panel of human mantle cell lymphoma (MLC) cell lines represented by Jeko-1, HBL2, Z-138, REC-1, Granta, Mino, and NECB1. These data are shown in Tables 28 and 29.

One set of data was obtained by maintaining BO-1055 at a single concentration corresponding to its $IC_{50}$ as a single agent determined against the cell line, and then evaluated for interactive cytotoxicity by combining BO-1055 with titrated concentration of each drug over a 7-9 fold range of drug concentrations for 72 hrs and determining cytotoxicity/inhibition of metabolic activity ($IC_{50}$) by alamar blue assay.

A second set of date was obtained by combining one drug at its $IC_{50}$ as a single agent with BO-1055 titrated over a 7-9 fold range of drug doses and undertaking an $IC_{50}$ determination at 72 hrs.

With 5 evaluable lines, BO-1055 and velcade were synergistic cytotoxic with both combinations against 2 lines (Z-138, MINO), antagonistic in both combinations against 1 line (REC-1) and synergistic with combo-1 and antagonistic with combo-2 against 2 lines (RANTA, NECB1). With BO-1055 and doxorubicin both combinations were synergistic against 2 lines, (Z-138, MINO), both combinations were antagonistic against 1 line (REC-1) and 2 lines were synergistic with combo-1 and antagonistic against combo-2 (RANTA, NECB1).

Thus, the individual MCL lines showed marked variation in response to the drug combinations, but their responses to velcade and bortezomib were identical. In contrast, the same panel of MCL lines showed different responses to HSP90 inhibition compared to HSP70 inhibition (Table 29). PUH71 was synergistic with BO-1055 in both combinations against Z-138 but in contrast, TT46 was antagonistic in both combinations against the same cell line. PUH71 was dually antagonistic to GRANTA whereas TT46 was synergistic in combo-1 and antagonistic in combo-2 against GRANTA. Both HSP inhibitors were antagonistic against REC-1 in both combinations with BO-1055. PUH71 was dually synergistic with BO-1055 against MINO whereas TT46 was synergistic with BO-1055 against this cell line only in combo-1 and antagonistic in combo-2. Both PUH71 and TT46 were synergistic with BO-1055 against NECB1 in combo-1 and antagonistic in combo-2.

TABLE 28

Efficacy of combined treatment of Mantle Cell Lymphoma lines with BO-1055 and Doxorubicin or Velcade (bortezomib)

| Cell Lines MCL | BO1055 | VELCADE | Comb-1 BO1055 (Var) VELC (Cte) | Comb-2 VELC (Var) BO1055 (Cte) | CI (Fa = 0.5) Comb-1 Comb-2 | Effect Comb-1 Comb-2 |
|---|---|---|---|---|---|---|
| JEKO-1 | 0.266 uM | 0.015 uM | — | — | — | — |
| HBL2 | 0.161 uM | 0.005 uM | — | — | — | — |
| Z-138 | 0.289 uM | 0.008 uM | Complete Effect | Complete Effect | 0.087 / 0.469 | Synergistic / Synergistic |
| REC-1 | 13.07 uM | 0.008 uM | 17.980 uM | 0.007 uM | 6.823 / 2.769 | Antagonistic / Antagonistic |
| MINO | 0.107 uM | 0.040 uM | Complete Effect | 0.024 uM | 0.305 / 0.895 | Synergistic / Synergistic |
| NECB1 | 7.450 uM | 0.137 uM | Complete Effect | 0.122 uM | 0.218 / 1.288 | Synergistic / Antagonistic |
| GRANTA | 5.562 uM | 0.008 uM | 2.876 uM | 0.011 uM | 0.894 / 3.691 | Synergistic / Antagonistic |

| Cell Lines MCL | BO1055 | DOXO | Comb-1 BO1055 (Var) DOXO (Cte) | Comb-2 DOXO (Var) BO1055 (Cte) | CI (Fa = 0.5) Comb-1 Comb-2 | Effect Comb-1 Comb-2 |
|---|---|---|---|---|---|---|
| JEKO-1 | 0.266 uM | 0.098 uM | — | — | — | — |
| HBL2 | 0.161 uM | 0.051 uM | — | — | — | — |
| Z-138 | 0.299 uM | 0.438 uM | Complete Effect | Complete Effect | 0.472 / 0.131 | Synergistic / Synergistic |
| REC-1 | 17.69 uM | >10 uM | 16.426 uM | >10 uM | 4.378 / 3.416 | Antagonistic / Antagonistic |
| MINO | 0.115 uM | 0.135 uM | Complete Effect | 0.032 uM | 0.274 / 0.557 | Synergistic / Synergistic |
| NECB1 | 7.418 uM | 1.227 uM | Complete Effect | 0.981 uM | 0.680 / 1.104 | Synergistic / Antagonistic |
| GRANTA | 5.258 uM | 0.257 uM | 4.439 uM | 0.258 uM | 0.755 / 1.579 | Synergistic / Antagonistic |

$IC_{50}$ (uM) values are referred to respective single drug or drug combination treatment.
Synergism: CI < 0.9,
Additive: 0.90 ≤ CI ≤ 1.10,
Antagonism: CI > 1.10

TABLE 29

Efficacy of combined treatment of Mantle Cell Lymphoma cell lines with BO-1055 and HSP90 inhibitor PUH71 or HSP70 inhibitor TT46

| Cell Lines MCL | BO1055 | PUH71 | Comb-1 BO1055 (Var) PUH71 (Cte) | Comb-2 PUH71 (Var) BO1055 (Cte) | CI (Fa = 0.5) Comb-1 Comb-2 | Effect Comb-1 Comb-2 |
|---|---|---|---|---|---|---|
| JEKO-1 | 0.266 uM | 0.037 uM | — | — | — | — |
| HBL2 | 0.161 uM | 0.499 uM | — | — | — | — |
| Z-138 | 0.303 uM | 0.162 uM | Complete Effect | Complete Effect | 0.536 / 0.389 | Synergistic / Synergistic |
| REC-1 | 12.50 uM | 0.250 uM | 11.630 uM | 0.254 uM | 2.451 / 1.789 | Antagonistic / Antagonistic |
| MINO | 0.105 uM | 0.263 uM | Complete Effect | 0.241 uM | 0.266 / 1.142 | Synergistic / Antagonistic |
| NECB1 | 7.777 uM | 1.655 uM | Complete Effect | 0.584 uM | 0.083 / 1.161 | Synergistic / Antagonistic |
| GRANTA | 5.496 uM | 1.218 uM | 3.758 uM | 1.121 uM | 1.278 / 1.659 | Antagonistic / Antagonistic |

| Cell Lines MCL | BO1055 | TT46 | Comb-1 BO1055 (Var) TT46 (Cte) | Comb-2 TT46 (Var) BO1055 (Cte) | CI (Fa = 0.5) Comb-1 Comb-2 | Effect Comb-1 Comb-2 |
|---|---|---|---|---|---|---|
| JEKO-1 | 0.266 uM | 0.167 uM | — | — | — | — |
| HBL2 | 0.161 uM | 0.251 uM | — | — | — | — |
| Z-138 | 0.301 uM | 0.510 uM | Complete Effect | Complete Effect | 1.219 / 1.105 | Antagonistic / Antagonistic |
| REC-1 | 19.26 uM | 0.237 uM | 20.056 uM | 0.237 uM | 5.863 / 2.871 | Antagonistic / Antagonistic |
| MINO | 0.101 uM | 0.215 uM | Complete Effect | 0.376 uM | 0.422 / 5.439 | Synergistic / Antagonistic |

TABLE 29-continued

Efficacy of combined treatment of Mantle Cell Lymphoma cell lines
with BO-1055 and HSP90 inhibitor PUH71 or HSP70 inhibitor TT46

| NECB1 | 8.521 uM | 1.546 uM | Complete Effect | 1.797 uM | 0.678 3.682 | Synergistic Antagonistic |
|---|---|---|---|---|---|---|
| GRANTA | 6.551 uM | 0.252 uM | 3.178 uM | 0.215 uM | 0.689 3.874 | Synergistic Antagonistic |

IC$_{50}$ (uM) values are referred to respective single drug or drug combination treatment.
Synergism: CI < 0.9
Additive: 0.90 ≤ CI ≤ 1.10
Antagonism: CI ≤ 1.10

(xviii) Xenograft Model of Mantle Cell Lymphoma and Tumor Suppression Produced by BO-1055

Figure 24:
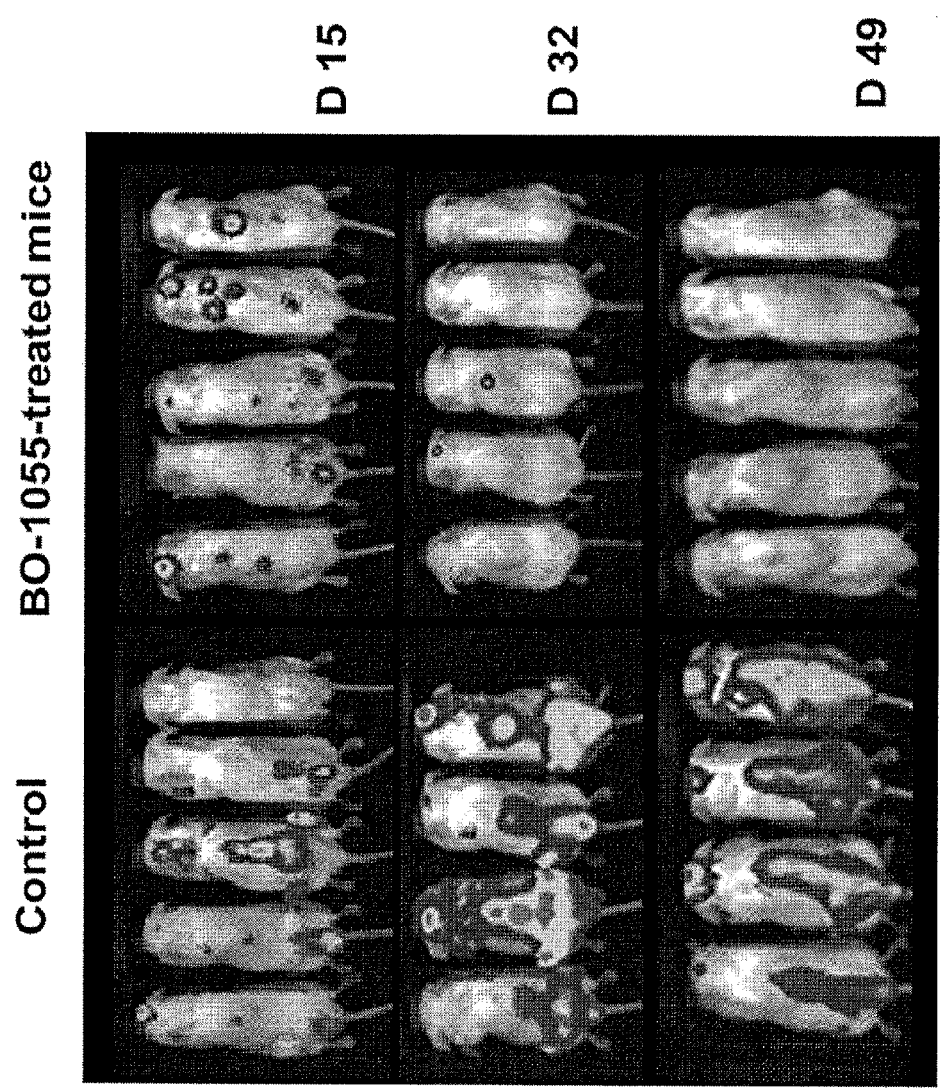
FIG. 24 shows six bioimaging photograph panels of five mice each. The three panels on the left show mice which were only injected with JEKO-1-GFP-Luc mantle cell lymphoma cells and control media; and the three panels on the right show mice which were injected with JEKO-1-GFP-Luc mantle cell lymphoma cells and were further treated with ureidomustine.

The Jako-1 mantle cell lymphoma cell line was labeled with GFP/Luciferase and 500,000 cells injected intravenously into each of 10 NSG female mice at 12 wks of age. IVIS Luciferin bioimaging was undertaken at day 15 and at this time point 5 mice were injected i.v. with BO-1055 (30 mg/kg) every other day for 10 days and 5 mice received a similar schedule of administration of a placebo (culture medium). Animals were imaged at intervals as shown in FIG. 24.

The control group showed progressive tumor growth up to 7 weeks post tumor transplantation (one mouse in this control group died before d32 but this mortality was probably unrelated to the tumor). The BO-1055-treated mice showed a dramatic suppression of tumor growth and by 7 wks (25 days after the end of drug treatment) there was no grossly observable tumor in any of the five mice. Gradual recurrence of tumor was detected by sensitive bioimaging in the treated group, beginning at day 41 (FIG. 24). All control mice were euthanized at 7 weeks due to tumor burden. BO-1055-treated mice were all alive at 75 days when the study was terminated.

Example 14C

Sarcoma

There were an estimated 60,000 cases of sarcoma worldwide in 2013/14 and 3,020 new cases annually in the U.S. with 1,460 deaths with the 5 year survival of 66.6%. The lifetime risk of developing sarcoma is 0.1%. There are more than 70 histologic sarcoma subtypes. The progression of and prognosis for any particular sarcoma depends on the subtype as well as the grade. The two major subdivisions are Osseous sarcomas (20% of cases) and Soft Tissue Sarcomas (80% of cases).

(i) Osteosarcoma.

This is an aggressive malignant tumor that arises from primitive mesenchymal cells and exhibits osteoblastic differentiation and production of malignant osteoid. Osteosarcoma comprises 2.4% of all malignancies in pediatric patients, and about 20% of all primary bone cancers. It is the eighth-most common form of childhood cancer and the most common histological form of primary bone cancer in children and young adults. It is a rare condition that is diagnosed in only about 1,000 individuals in Europe and the USA per year with approximately 300 deaths per year.

(ii) Synovial Cell Sarcoma.

This sarcoma usually occurs in young adults, most commonly in the arms or legs next to a joint, but they rarely invade the joint itself. The most common site is adjacent to the knee. Unlike other soft tissue sarcomas, synovial cell sarcomas are often painful. Treatment usually consists of radical excision with radiation and chemotherapy or amputation combined with chemotherapy.

(iii) Rhabdomyosarcomas.

These cancerous tumors of the striated or skeletal muscle and are one of the most common types of soft tissue sarcoma, and account for about half the soft tissue sarcomas diagnosed in children. They most commonly grow in the arms or legs but can also develop in the head or neck or in the urinary or reproductive organs. There are several different types, including pleomorphic, alveolar, embryonal and botryoid.

(iv) Leiomyosarcoma (Smooth Muscle Tumor) and Uterine Sarcoma

These sarcomas are cancerous tumors of the smooth muscle. They most commonly occur in the organs (e.g. GI tract and the uterus). The average age of patients is 60 years. Of the tumors occurring in the GI tract 61% occur in the stomach, 29% in the small bowel, and 10% in the colon. Symptoms of GI or uterine leiomyosarcomas are significant bleeding and pain. Metastases occur in more than half of patients. Metastases usually occur in the lungs except in GI tumors, which often metastasize in the liver. Treatment for uterine leiomyosarcoma is total abdominal hysterectomy.

(v) Gastrointestinal Sarcoma, otherwise known as Gastrointestinal Stromal Tumor (GIST).

GIST develops in the stroma of the stomach and intestines and is characterized by activating c-Kit mutations. It is treated with Gleevec®.

(vi) Kaposi's Sarcoma.

Kaposi's Sarcoma is a disease in which cancerous cells are found in the tissues under the skin or mucous membranes that line the mouth, nose and anus. There are three groups of patients for Kaposi's sarcoma. The first group typically includes older men of Jewish, Italian or Mediterranean heritage. This type of Kaposi's usually progresses slowly over 10-15 years. Patients commonly develop a bluish lesion on the front of the lower leg, which typically spreads to multiple lesions. After some time, the disease can spread to other organs. The second group of Kaposi's sarcoma occurs in patients who have received organ transplant. Due to the Immunosuppressive treatment following a transplant, patients' immune systems are weakened thus are more susceptible to infection. The third group of Kaposi's sarcoma is found in AIDS patients. This group is referred to as epidemic Kaposi's sarcoma. Due to the weakened immune system cause by the HIV virus, Infections and other diseases such as Kaposi's can invade the body. Kaposi's sarcoma in people with AIDS usually spreads more quickly and can be found in many parts of the body. Radiation therapy is usually the treatment for Kaposi's; however, when lesions have spread to the organs, chemotherapy is often used as well.

(vii) Liposarcoma.

This is the most commonly diagnosed soft tissue tumor and is among the largest category of sarcomas reported.

These tumors usually develop in the deep fatty tissue. They most commonly occur in the thigh, behind the knee, the groin, the gluteal area or in the retroperitoneum. Liposarcomas are usually malignant and rarely are from a pre-existing lipoma, which is a non-cancerous tumor. They are most commonly found in adults between 30 and 60 years old and are slightly more common in men than women. Metastases to the lymph nodes occur in approximately 10% cases.

(viii) Chondrosarcoma.

These tumors develop from cartilage cells.

(ix) Ewing's Sarcoma (ES)

Ewing's sarcoma family tumors (ESFT) are bone or soft tissue sarcomas that are found primarily in adolescents and young adults, with peak occurrence between ages 10 and 20 (Burchill 2008). ES is genetically characterized by chromosomal translocation involving the Ewing's sarcoma breakpoint region 1 (EWSR1) gene. Translocation of EWSR1 on chromosome 22 to chromosome 11 occurs in 85% of ES cases, forming the fusion protein product EWS-FLI1 (de Alava & Gerald 2000). In addition, fusion product EWS-ERG is identified in 10% of cases. The EWSR1 breakpoint appears to be a hot spot for genetic translocations and can promiscuously bind other C-terminal genes in other sarcoma subtypes such as clear cell sarcoma, extraskeletal myxoid chondrosarcoma and others. FLI1, ERG and other ETS genes contain the DNA-binding domain and EWS-FLI1 protein functions as an aberrant transcription factor regulating malignant transformation to ES. The prognosis of patients with metastatic Ewing's sarcoma remains dismal and 5-year survival usually does not exceed 30% despite the development of systemic therapies (Jiang et al. 2015).

(x) Leiomyosarcoma. These tumors develop from smooth muscle in abdominal and pelvic organs and blood vessels.

Cytotoxicity of BO-1055 in a Panel of 28 Human Sarcoma Cell Lines

DNA cross-linking agents continue to be an important part of chemotherapy for pediatric sarcomas. In the current investigation, the inventors found that BO-1055 exhibits significant cytotoxicity against cell growth of various sarcoma cell line in vitro and in tumor xenograft models. The inventors determined the efficacy of BO-1055-mediating cytotoxicity in Ewing's sarcoma, Rhabdomyosarcoma, Osteosarcoma, and Desmoplastic Small Round Blue Cell Tumor (DSRCT) cell lines and compared that with Temazolamide, Melphalan, and Doxrubicin. (Table 30) (Ambati et al. 2014a,b).

BO-1055 was highly toxic to 8/9 Ewing's cell lines ($IC_{50}$ 0.14-0.61 µM) and moderately toxic to 1/9 ($IC_{50}$ 1.04 µM). Similarly, BO-1055 was highly toxic to 4/5 rhabdomyosarcoma lines ($IC_{50}$ 0.08-0.40 µM) but one line (SMS-CTR embryonal type) was highly resistant ($IC_{50} \geq 10.0$ µM). The two Desmoplastic small round cell tumor lines were moderately sensitive to BO-1055 ($IC_{50}$ 2.41-3.74 µM). In contrast, 3 of 5 osteosarcoma lines were highly resistant to BO-1055 ($IC_{50} \geq 10.0$-$\geq 100.0$ µM). one line was highly sensitive ($IC_{50}$ 0.45 µM), and one moderately sensitive ($IC_{50}$ 2.67 µM).

Temozolamide (TMZ) toxicity was determined on 9 lines and of these, 3 were Ewing's sarcoma and highly resistant ($IC_{50}$ 245.0-405.0 µM) as were 5/6 rhabdomyosarcoma lines ($IC_{50}$ 191.0->1,000.0 µM). The RH30 (Alveolar type) rhabdomyosarcoma line was moderately resistant to TMZ ($IC_{50}$ 9.0 µM) but highly sensitive to BO-1055 ($IC_{50}$ 0.24 µM). Melphalan was highly cytotoxic to the eight Ewing's and Rhabdomyosarcoma lines it was tested against ($IC_{50}$ 0.0001-0.020 µM).

Doxorubicin was highly cytotoxic to all the lines it was screened against, including three Ewing's sarcomas ($IC_{50}$ 0.005-0.38 µM). Two osteosarcoma lines that were highly resistant to BO-1055 were highly sensitive to doxorubicin ($IC_{50}$ 0.025-0.090 µM) as was the one Rhabdomyosarcoma line tested ($IC_{50}$ 0.011 µM). The results demonstrate that BO-1055 is more cytotoxic than TMZ, but is less potent than melphalan and doxorubicin against the cell growth of sarcoma cell lines tested.

TABLE 30

BO-1055 cytotoxic activity was determined in a panel of 28 human sarcoma cell lines representing 4 tumor subtypes:- Desmoplastic small round cell tumors (DSRCT) n = 2, Ewing's n = 11, Osteosarcoma n = 5 and Rhabdomyosarcoma n = 9

| Sarcoma, DSRCT[1] | BO-1055 | TMZ[2] | Melph[2] | Doxo[2] |
|---|---|---|---|---|
| BER | 2.41 | ND[3] | ND | ND |
| BOD | 3.74 | ND | ND | ND |
| | BO-1055 | TMZ | Melph | Doxo |
| Sarcoma Ewing's | | | | |
| A673 | 0.52 | ND | ND | 0.38 |
| CAR | 0.31 | ND | ND | ND |
| CHLA-9 | 0.60 | 294.0 | 0.0001 | ND |
| IARC-EW1 | 0.43 | ND | ND | ND |
| ORA | 0.32 | ND | ND | ND |
| SIM-1 | 1.04 | ND | ND | ND |
| SK-N-MC | 0.61 | ND | ND | ND |
| TC-32 | 0.60 | ND | ND | 0.005 |
| ZUC | 0.14 | ND | ND | ND |
| Sarcoma, Osteosarcoma | | | | |
| HOS | 0.43 | ND | ND | ND |
| MG63 | 2.67 | ND | ND | ND |
| OSA | ≥10.0 | ND | ND | ND |
| Saos-1 | ≥100.0 | ND | ND | 0.025 |
| U2OS | ≥20.0 | ND | ND | 0.090 |
| Rhabdomyosarcoma | | | | |
| A204 (rhabdoid?) | 0.08 | 569.0 | ND | 0.011 |
| RH30 Alveolar | 0.24 | 9.00 | 0.0200 | ND |
| RMS-559 embryonal | 0.25 | ND | ND | ND |
| SMS-CTR embryonal | ≥10.0 | ND | ND | ND |
| TE-381-T[4] | 0.40 | ND | ND | ND |

Figure 25A:
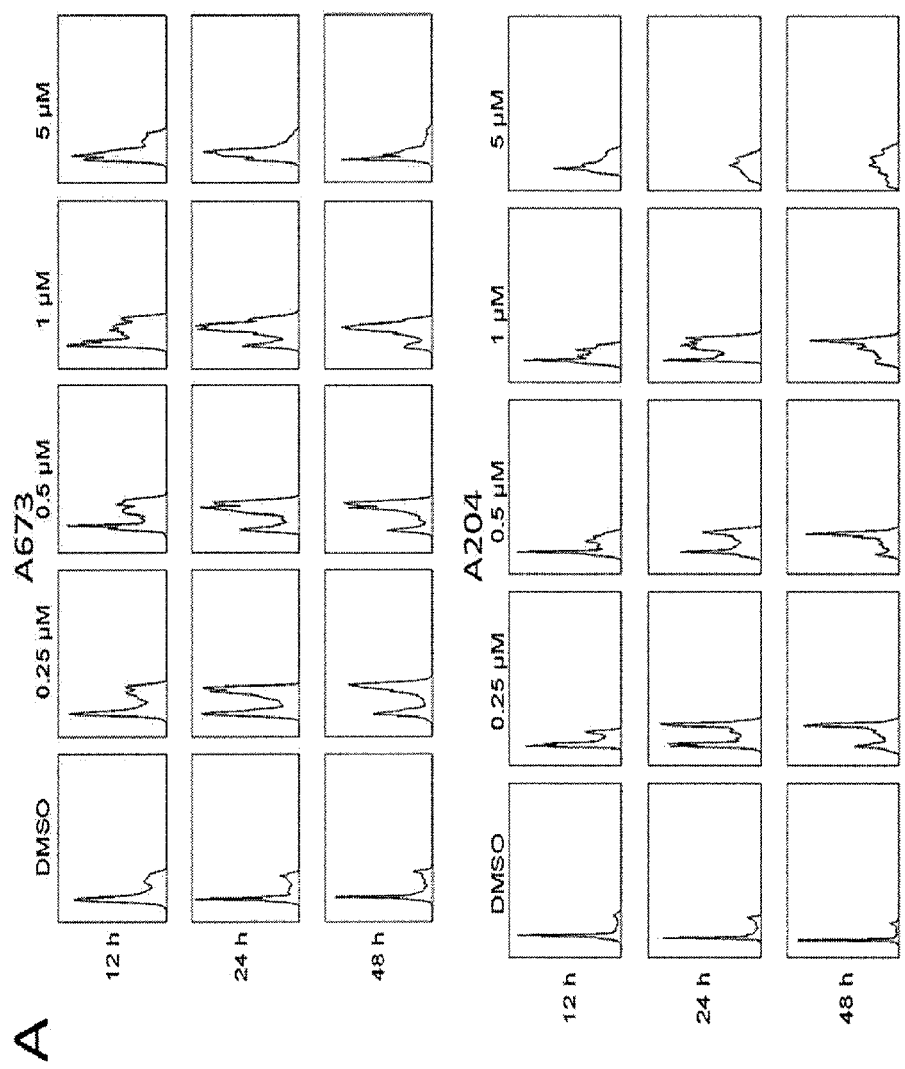
FIG. 25A shows a flow cytometry cell cycle distribution of A673 Ewing's sarcoma and A204 rhabdomyosarcoma cell lines following ureidomustine treatment.

[1]DSRCT = Desmoplastic small-round-cell tumor;
[2]TMZ = Temozolomide,
[2]Melph = Melphalan,
[2]Doxo = Doxorubicin.
[3]ND = not determined;
[4]Mixed connective and soft tissue, fibroblast (xi) BO-1055 Induces Cell Cycle Arrest in G2/M Phase in A673 Ewing's Sarcoma Cells and A204 Rhabdomyosarcoma Cells Cell cycle inhibition and apoptosis induced by BO-1055 in the A673 Ewing's sarcoma cell line and the A204 Rhabdomyosarcoma cell line was determined by flow cytometry (FIG. 25A). FIG. 25A shows the results of flow cytometric analysis of A673 cell line using 7-AAD (for viability testing) and Annexin V-APC (for apoptosis) staining at 12, 24, 48 and 72 hours at indicated concentrations of BO-1055.

The results revealed that BO-1055 induced cell cycle arrest in the G2/M phase in both cell lines in a dose-dependent and time-dependent manner.

Figure 25B:
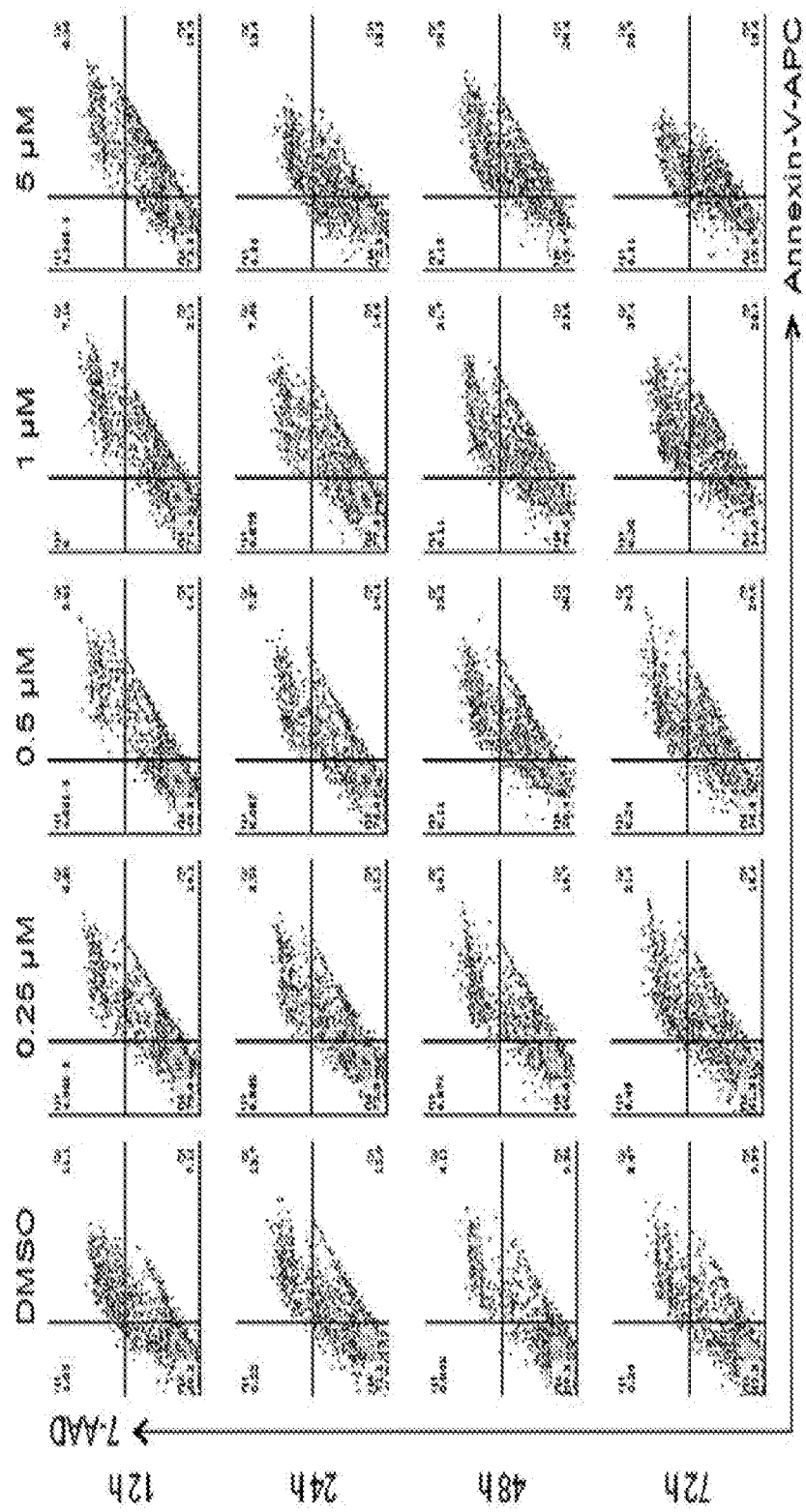
FIG. 25B shows the percentages of apoptotic and dead A673 cells following ureidomustine treatment.

FIG. 25B shows a graphical representation of the percentages of apoptotic and dead cells at different time points after BO-1055 treatment.

Figure 25E:
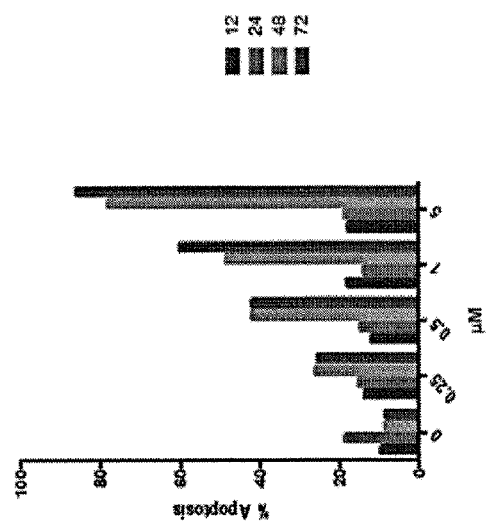
FIG. 25E shows a graphical representation of the percentage of apoptotic A673 cells following ureidomustine treatment.
Figure 25D:
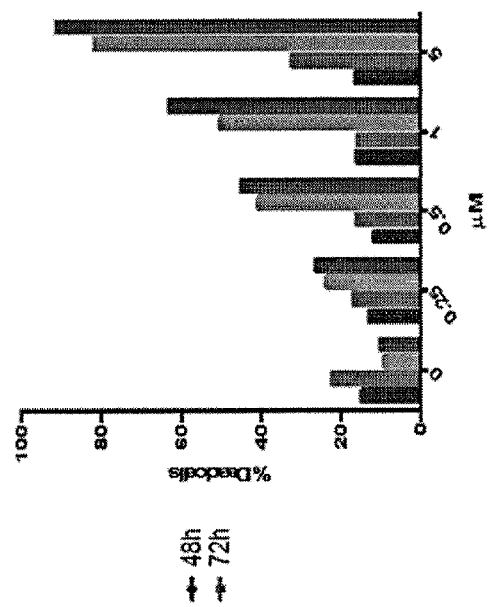
FIG. 25D shows a graphical representation of the percentage of dead A673 cells following ureidomustine treatment.
Figure 25C:
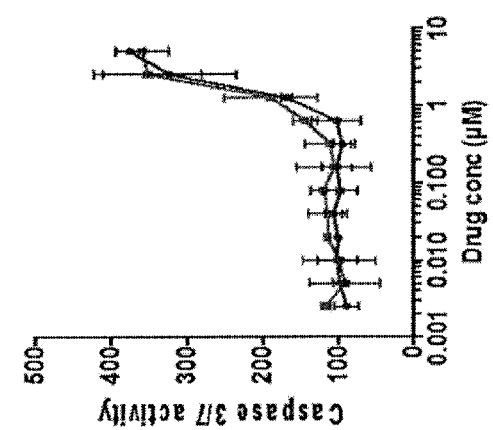
FIG. 25C shows a graph of caspase activity in A673 cells following ureidomustine treatment.

FIG. 25C shows a graph of caspase 3/7 activity in A673 cells at 48 h and 72 h after treatment with BO-1055.

FIG. 25D is a graphical representation of the percentage of dead A673 cells at 12, 24, 48 and 72 hrs after different doses of BO-1055 were applied.

FIG. 25E is a graphical representation of the percentage of apoptotic A673 cells at 12, 24, 48 and 72 hrs after different doses of BO-1055 were applied.

(xii) BO-1055 Inhibited A673 Ewing's Sarcoma in a Methylcellulose Culture Onco-Sphere Formation Assay The inventors studied the inhibition A673 Ewing's sarcoma in methylcellulose culture by onco-sphere formation assay (FIGS. 26A and 26B).

FIG. 26A shows inhibition of A673 Ewing's sarcoma onco-sphere formation in methylcellulose culture following treatment with various concentrations of BO-1055 or 4-Hydroperoxycyclophosphamide. 50% inhibition of sphere formation was seen with 1.00 µM 4-HC and with <0.10 µM BO-1055.

FIG. 26B shows oncosphere formation in methylcellulose.

The results showed BO-1055 was more cytotoxic than the 4-Hydroperoxycyclophosphamide, which was used as the positive control.

(xiii) In vitro Synergistic Cytotoxicity of BO-1055 Against the A673 Ewing's Sarcoma Cell Line in Combination with Different Chemotherapeutic Agents.

The inventors evaluated the cytotoxic effect of BO-1055 on the A673 Ewing's sarcoma cell line using a combination of BO-1055 with different chemotherapeutic agents, such as topotecan, SN-38, doxorubicin, and PU-H71.

As shown in FIGS. 27A-D, there was synergistic cytotoxicity of BO-1055 against A673 Ewing's sarcoma cell line by combining it with different chemotherapeutic agents tested.

Specifically, varying concentrations of BO-1055 and the second drug were applied simultaneously in a lattice format in a 96 well plate and the cytotoxicity is quantified using Alamar blue cell proliferation assay. Then, Fa-combination index (CI) plot and normalized isobolograms were generated using Compusyn software for each combination.

Figures 27A, 27B, 27C, 27D:
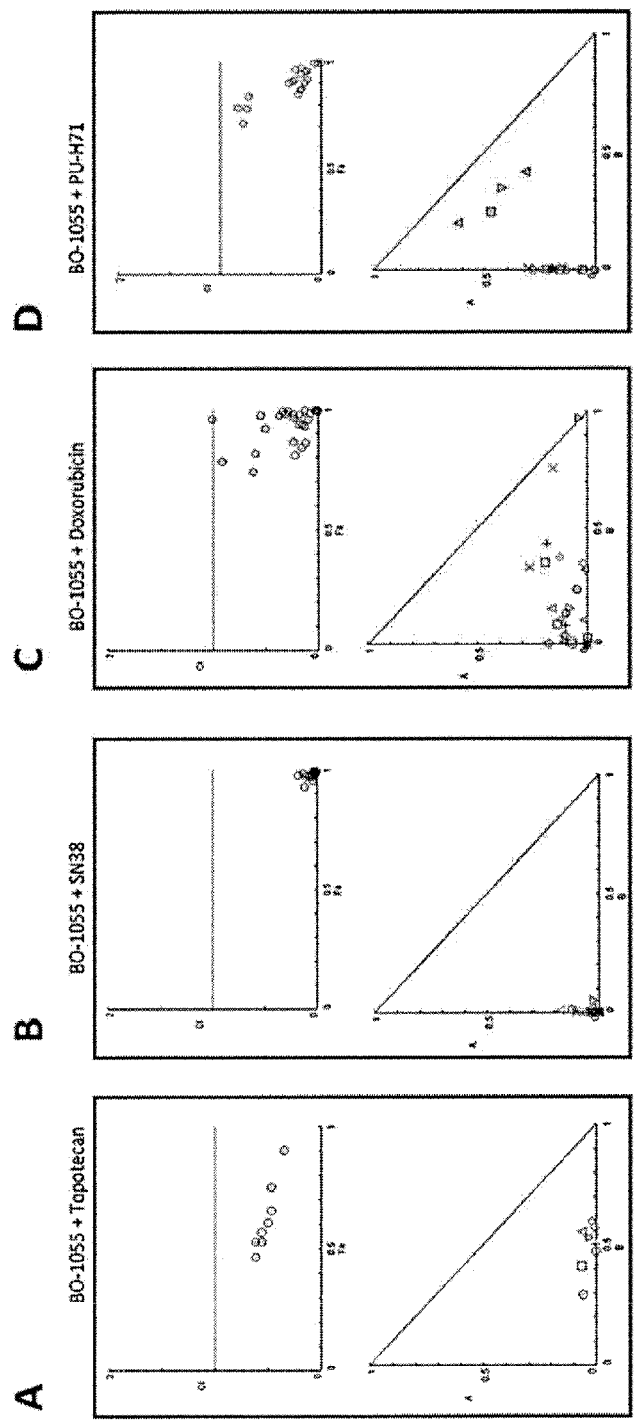
FIG. 27A shows an isobologram obtained by GraphPad Prism on A673 Ewing's sarcoma cells treated with a combination of ureidomustine and topotecan.
FIG. 27B shows an isobologram of the same cells treated with a combination of ureidomustine and SN-38.
FIG. 27C shows an isobologram of the same cells treated with a combination of ureidomustine and doxorubicin.
FIG. 27D shows an isobologram of the same cells treated with a combination of ureidomustine and PU-H71, an HSP90 inhibitor.

FIG. 27A shows the isobologram of a combination of BO-1055 and topotecan;

FIG. 27B shows the isobologram of a combination of BO-1055 and SN-38;

FIG. 27C shows the isobologram of a combination of BO-1055 and doxorubicin; and

FIG. 27D shows the isobologram of a combination of BO-1055 and PU-H71. This combination exhibits synergism against Ewing's sarcoma cells in vitro.

(xiv) BO-1055 Exhibits Potent Therapeutic Efficacy Against Ewing's Sarcoma Tumor Xenografts in NSG Mice.

The therapeutic efficacy of BO-1055 in NSG mice bearing Ewing's sarcoma xenografts was determined. As shown in FIGS. 31A-E, BO-1055 caused complete regression of tumor growth in nude mice at the dose of 30 mg/kg four doses by tail vein injection. A complete regression of tumors was noted in the treated group.

NSG mice (n=5 per group) bearing A673 Ewing's sarcoma xenografts of approximately 100 mm³ size were given 5 doses of BO-1055 at 10 mg/kg, 20 mg/kg and 30 mg/kg doses by tail vein injection. The results are shown in FIGS. 28A-C.

Figure 28:
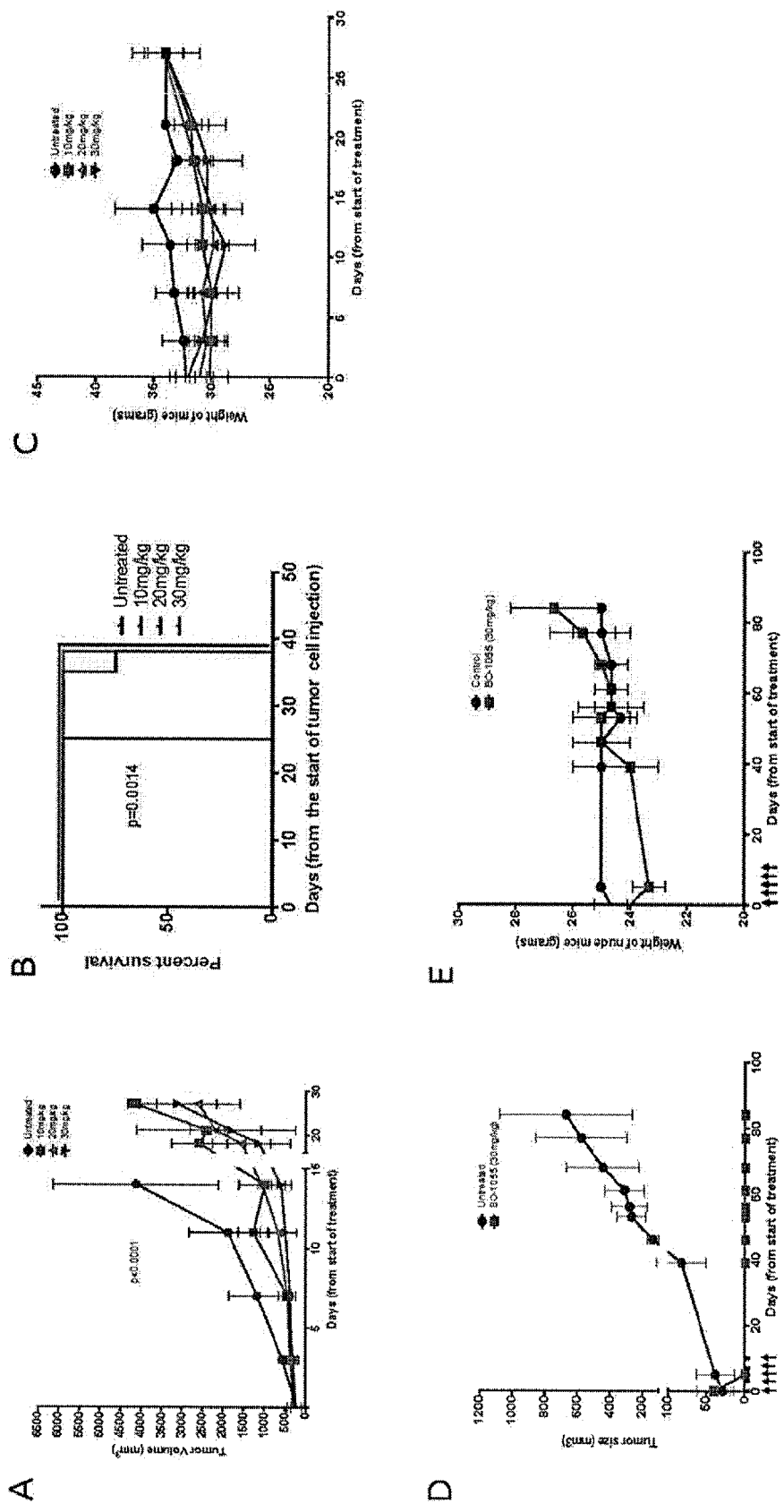
FIG. 28A shows a graph of tumor volume vs days from start of treatment of NSG mice bearing A673 Ewing's sarcoma xenografts and treated with different doses of ureidomustine.
FIG. 28B shows Kaplan-Meier survival curves in the same mice.
FIG. 28C shows a graph of weight of mice vs days from start of ureidomustine treatment of the same mice.
FIG. 28D shows a graph of tumor size vs days from start of treatment of NSG mice bearing A204 rhabdomyosarcoma xenografts and treated with ureidomustine.
FIG. 28E shows a graph of weight of mice vs days from start of ureidomustine treatment of the same mice.

FIG. 28A shows a plot of tumor volume which was measured twice a week.

FIG. 28B shows Kaplan-Meier survival curves in mice.

FIG. 28C shows a plot of weights of the treated mice.

Nude mice (n=5) per group bearing A204 rhabdomyosarcoma xenografts were treated with BO-1055 at a dose of 30 mg/kg on alternate days for five doses by tail vein inj. The results are shown in FIGS. 28D and 28E.

FIG. 28D shows a plot of tumor size.

FIG. 28E shows a plot of weights of the treated mice.

Complete regression of tumors was noted in the treated group.

(xv) BO-1055 Effectively Inhibited Ewing's Sarcoma Xenografts, a Cyclophosphamide-resistant Xenograft in NSG Mice BO-1055 was used against a cyclophosphamide-resistant xenograft of a Ewing's sarcoma primary patient tumor sample transplanted subcutaneously into NSG mice. When the tumors in NSG mice reached 100 mm³, mice were randomized into control and drug treatment groups. Mice in the control groups received PBS injections, mice in the drug treatment group received an MTD dose of cyclophosphamide (70 mg/kg) as an intraperitoneal injection every other day for 3 doses (shown by shorter arrows in FIG. 29). Tumor growth was not inhibited in the cyclophosphamide treated mice. When the tumors reached ≥500 mm³, treatment was started with BO-1055 at a dose of 30 mg/kg. iv injection, every other day for 4 doses (shown by longer arrows). Note regression of cyclophosphamide-refractory tumors upon treatment with BO-1055.

Figure 29:
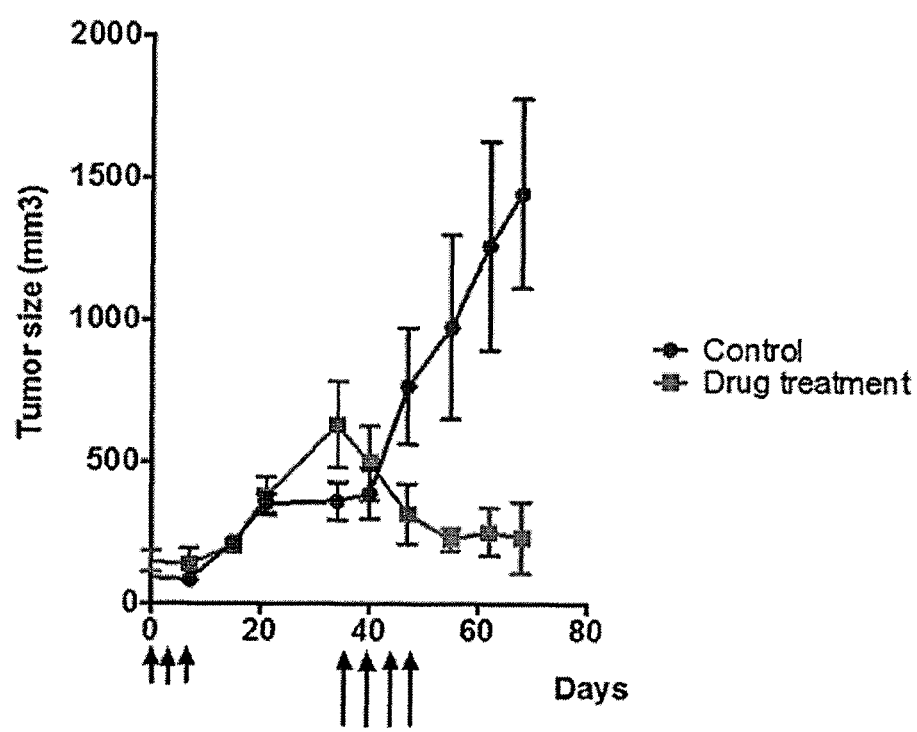
FIG. 29 shows a graph of tumor size vs days from start of treatment of NSG mice bearing primary Ewing's sarcoma xenografts and treated first with 3 daily injections of cyclophosphamide, and following progressive tumor growth, with 4 injections of ureidomustine.

The results are shown in FIG. 29. As one can see, BO-1055 inhibited a cyclophosphamide-resistant xenograft established in NSG mice (second passage) from a patient with relapsed Ewing's sarcoma who had been treated with two alkylating agents as upfront treatment.

REFERENCES

1) Akyurek N, Uner A, Benekli M, Barista I. Prognostic significance of MYC, BCL2, and BCL6 rearrangements in patients with diffuse large B-cell lymphoma treated with cyclophosphamide, doxorubicin, vincristine, and prednisone plus rituximab. Cancer 2011; 118 (17): 4173-83.

2) Ambati S R, Lopes E C, Kosugi K, Mony U, Zehir A, Shah S K, Taldone T, Moreira A L, Meyers P A, Chiosis G, Moore M A. Pre-clinical efficacy of PU-H71, a novel HSP90 inhibitor, alone and in combination with bortezomib in Ewing's sarcoma. Mol Oncol. 2014a March; 8(2):323-36.

3) Ambati S R, Wong E W, Pera B, Peguero E, Caldas Lopes E, Chen J J, Shieh J H, Su T L, Moore M A. Pre-clinical evaluation of a novel DNA crosslinking agent, Ureidomustine (BO-1055) in pediatric sarcomas. Proceedings of the 105th Annual Meeting of the American Association for Cancer Research; 2014b Apr. 4-9; San Diego, Calif.; Cancer Res 2014; 74(19 Suppl); Abstract nr 3980.

4) American Cancer Society: Cancer Facts and Figures 2015. Atlanta, Ga.: American Cancer Society, 2015. Available online 5) Apostolopoulos C, Castellano L, Stebbing J, Giamas G. Bendamustine as a model for the activity of alkylating agents. Future Oncol. 2008, 4:323-332.

6) Appleman L J, Balasubramaniam S, Parise R A, Bryla C, Redon C E, Nakamura A J, Bonner W M, Wright J J Piekarz I R Kohler D R, Jiang Y, Belani C P, Eiseman J, Chu E, Beumer J H, Bates S E. A Phase I Study of DMS612, a Novel Bifunctional Alkylating Agent. Clin Cancer Res. 2015 Feb. 15; 21(4):721-9.

7) Armitage J O. My Treatment Approach to Patients With Diffuse Large B-Cell Lymphoma. Mayo Clinic Proceedings. 2012; 87(2):161-171.

8) Armstrong A J, George D J. Satraplatin in the treatment of hormone-refractory metastatic prostate cancer. Therapeutics Clin Risk Management. 2007; 3(5):877-883.

9) Azim H A, Ganti A K. Treatment options for relapsed small-cell lung cancer. Anticancer Drugs 2007; 18 (3): 255-261.

10) Barretina J, Caponigro G, Stransky N, et al. The Cancer Cell Line Encyclopedia enables predictive modelling of anticancer drug sensitivity. Nature. 2012 Mar. 28; 483(7391):603-7. doi: 10.1038/nature11003.

11) Bartelink I H, van Reij E M, Gerhardt C E, van Maarseveen E M, de Wildt A, Versluys B, Lindemans C A, Bierings M B, Boelens J J. Fludarabine and exposure-targeted busulfan compares favorably with busulfan/cyclophosphamide-based regimens in pediatric hematopoietic cell transplantation: maintaining efficacy with less toxicity. Biol Blood Marrow Transplant. 2014; 20(3):345-53.

12) Baughn L B, Di Liberto M, Wu K, Toogood P L, Louie T, Gottschalk R, Niesvizky R, Cho H, Ely S, Moore M A S, Chen-Kiang S. A novel orally active small molecule potently induces $G_1$ arrest in primary myeloma cells and prevents tumor growth by specific inhibition of Cyclin-dependent kinase 4/6. Cancer Res. 2006. 66:7661-7667.

13) Berry S, Cosby R, Asmis T, Chan K, Hammad N, Krzyzanowska M K. Cancer care Ontario's Gastrointestinal Disease Site Group. Continuous versus intermittent chemotherapy strategies in metastatic colorectal cancer: a systematic review and meta-analysis. Ann Oncol 2015; 26:477-485.

14) Biesalski H K, Bueno de Mesquita B, Chesson A et al. European Consensus Statement on Lung Cancer: risk factors and prevention. Lung Cancer Panel. CA Cancer J Clin 1998; 48 (3): 167-176; discussion 164-166. doi:10.3322/canjclin.48.3.16.).

15) Bode-Lesniewska B, et al. Relevance of translocation type in myxoid liposarcoma and identification of a novel EWSR1-DDIT3 fusion Genes Chromosom Canc. 2007; 46:961-971

16) Boss, R. Shadow falls on anti-antiogiogenetic drugs. Cancer Decisions Newsletter Archives. 2009, Mar. 15.

17) Bower M, Newlands E S, Bleehen N M, Brada M, Begent R J H, Calvert H, Colquhoun I, Lewis P, Brampton M H. Multicentre CRC phase II trial of temozolomide in recurrent or progressive high-grade glioma. Cancer Chemother. Pharmacol. 1997, 40, 484-488.

18) Brambilla E, Travis W D, Colby T V, Corrin B, Shimosato Y The new World Health Organization classification of lung tumours. Eur. Respir. J. 2001; 18 (6): 1059-68.

19) Breems D A, Blokland E A, Nebens S, Ploemacher R E. Frequency analysis of human primitive haematopoietic stem cell subsets using a cobblestone area forming cell assay. Leukemia 1994; 8:1095-104.

20) Brenner A. et al., A Phase 1/2 study of TH-302, investigational hypoxia-activated prodrug, and bevacizumab in patients with bevacizumab-refractory recurrent glioblastoma. Society of Neuro-oncology Annual Meeting, 2014 Abstract #AT-12.

21) Brenner H, Gondos A, Pulte D. Survival expectations of patients diagnosed with Hodgkin's lymphoma in 2006-2010. Oncologist. 2009 August; 14(8):806-13. doi: 10.1634/theoncologist.2008-0285.

22) Browder T, Butterfield C E, Kraling B M, Shi B, Marshall B, O'Reilly M S, et al. Antiangiogenic scheduling of chemotherapy improves efficacy against experimental drug-resistant cancer. Cancer Res 2000; 60:1878-86.

23) Burchill S A. Molecular abnormalities in Ewing's sarcoma. Expert Rev Anticancer Ther. 2008; 8:1675-1687.

24) Casanovas O, Hicklin D J, Bergers G, Hanahan D. Drug resistance by evasion of antiangiogenic targeting of VEGF signaling in late-stage pancreatic islet tumors. Cancer Cell. 2005, 8:299-309.

25) Castro-Malaspina H M Gay R E, Resnick G. Kapoor N, Chiareri D, McKenzie S, Broxmeyer H, and Moore M A S. Characterization of human bone marrow fibroblast colony-forming cells (CFU-F) and their progeny. Blood. 1980 August; 56(2):289-301

26) Cavazos, D. A. et al., Pharmacodynamic biomarker assessments in a Phase I/II trial of the hypoxia-activated prodrug TH-302 and bevacizumab in bevacizumab-refractory recurrent glioblastoma. Society of Neuro-oncology Annual Meeting, 2014. Abstract #DD-02.

27) Chan J K, Loizzi V, Manetta A, Berman M L. Oral altretamine used as salvage therapy in recurrent ovarian cancer. Gynecol. Oncol. 2004; 92 (1): 368-71.

28) Chen Y R, Su T L, Hsia P W unpublished results 2013.

29) Chien S I, Yen J C, Kakadiya R, Chen C H, Lee T C, Su T L, Tsai T H: Determination of tissue distribution of potent antitumor agent ureidomustin (BO-1055) by HPLC and its pharmacokinetic application in rats. J Chromatogy 2013; 917-918:62-70.

30) Cho H Y, Wang W, Jhaveri N et al. NE0212, temozolomide Conjugated to Perillyl Alcohol, Is a Novel Drug for Effective Treatment of a Broad Range of Temozolomide-Resistant Gliomas. Mol Cancer Ther 2014; 13(8); 2004-17.

31) Cho Y S, Wu K-D, Moore M A S, Chou T-C, Danishefsky S J. Second-generation epothilones: discovery of fludelone and its extraordinary antitumor properties. Drugs of the Future 2005, 30(5):1-9.

32) Chou T C. Drug combination studies and their synergy quantification using the Chou-Talalay method. Cancer Res 2010; 70(2):440-446.

33) Chou T C, Talalay P. Quantitative analysis of dose-effect relationships: the combined effects of multiple drugs or enzyme inhibitors. Adv Enzyme Regul 1984; 22:27-55. Choy H, Park C, Yao M. Current status and future prospects for satraplatin, an oral platinum analogue. Clin Cancer Res 2008; 14 (6): 1633-8.

34) Chung K Y, Morrone G, Schuringa J J, Wong B, Dorn D C, Moore M A. Enforced expression of an Flt3 internal tandem duplication in human CD34+ cells confers properties of self-renewal and enhanced erythropoiesis. Blood. 2005 Jan. 1; 105(1):77-84.

35) Chung K Y, Morrone G, Schuringa J J, Wong B, Dorn D C, Moore M A. Enforced expression of an Flt3 internal tandem duplication in human CD34+ cells confers properties of self-renewal and enhanced erythropoiesis. Blood. 2005, 105:77-84.

36) Coiffier B, Thieblemont C, Van Den Neste E et al. Long-term outcome of patients in the LNH-98.5 trial, the first randomized study comparing rituximab-CHOP to standard CHOP chemotherapy in DLBCL patients: a study by the Groupe d'Etudes des Lymphomes de l'Adulte. Blood 2010; 116(12):2040-5.

37) Deacon M, Singleton D, Szalkai N et al. Early evaluation of compound QT prolongation effects: A predictive 384-well fluorescence polarization binding assay for measuring hERG blockade. J Pharmacol Toxicol Methods 2007; 55:255-264.
38) de Alava E, Gerald W L. Molecular biology of the Ewing's sarcoma/primitive neuroectodermal tumor family. J Clin Oncol. 2000; 18:204-213.
39) Dela Cruz C S, Tanoue L T, Matthay R A. Lung cancer epidemiology, etiology and prevention Clinic in Chest Med 2011; 32 (4): 605-644.
40) Delhommeau F, Dupont S, Della Valle V, et al. Mutations in TET2 in Myeloid Cancers. N Engl J Med 2009; 360(22):2289-2301.
41) Denny W A, Wilson W R. The design of selectively activated anti-cancer prodrugs for use in antibody-directed and genedirected enzyme prodrugs therapies. J. Pharm. Pharmacol. 1998, 50:387-394.
42) Dietlein F and Reinhardt H C. Molecular Pathways: Exploiting Tumor-Specific Molecular Defects in DNA Repair Pathways for Precision Cancer Therapy. Clin Cancer Res 2014; 20:5882-5887.117.
43) Droogendijk H J, Kluin-Nelemans H J, van Doormaal J J, Oranje A P, van de Loosdrecht A A, van Daele P L. Imatinib mesylate in the treatment of systemic mastocytosis: a phase II trial. Cancer. 2006, 107, 345-51.
44) Du R, Lu K V, Petritsch C, Liu P, Ganss R, Passegué E, Song H, Vandenberg S, Johnson R S, Werb Z, Bergers G. HIF1alpha induces the recruitment of bone marrow-derived vascular modulatory cells to regulate tumor angiogenesis and invasion. Cancer Cell. 2008, 13:206-220.
45) Fernandez F G, Battafarano R J. Large-cell neuroendocrine carcinoma of the lung. Cancer Control 2006; 13 (4): 270-5.
46) Feugier P, Li N, Jo D Y, Shieh J H, MacKenzie K L, Lesesve J F, Latger-Cannard V, Bensoussan D, Crystal R G, Rafii S, Stoltz J F, Moore M A. Osteopetrotic mouse stroma with thrombopoietin, c-kit ligand, and flk-2 ligand supports long-term mobilized CD34+ hematopoiesis in vitro. Stem Cells Dev. 2005. 14:505-16.
47) Franco S, MacKenzie K L, Dias S, Alvarez S, Rafii S, Moore M A S. Clonal variation in phenotype and lifespan of human embryonic fibroblasts (MRC-5) transduced with the catalytic component of telomerase (hTERT). Exp Cell Research, 2001, 268: 14-25.
48) Fuld A D, Dragnev K H, Rigas J R. Pemetrexed in advanced non-small-cell lung cancer". Expert Opin Pharmacother 2010; 11 (8): 1387-402.
49) Garnett M J, Edelman E J, Heidorn S J, Greenman C D, et al. Systematic identification of genomic markers of drug sensitivity in cancer cells. Nature 2012; 483: 570-5.
50) Gatenby R A, Silva A S, Gillies R J, Frieden B R. Adaptive therapy. Cancer Res 2009; 69(11):4894-903.
51) Golub T R, Barker G F, Lovett M, Gilliland D G. Fusion of PDGF receptor β to a novel ets-like gene, tel, in chronic myelomonocytic leukemia with t(5;12) chromosomal translocation. Cell 1994; 77:307-316.
52) Greaves M, Maley C C. Clonal evolution in cancer. Nature 2012; 481:306-1310.
53) Grothey A, Hart L L, Rowland K M, Ansari R H, Alberts S R, Chowhan N M, et al. Intermittent oxaliplatin (oxali) administration and time-to-treatment-failure (TTF) in metastatic colorectal cancer (mCRC): final results of the Phase III CONcePT trial. J Clin Oncol 2008; 26(15 Suppl):4010.
54) Hait W N. Anticancer drug development: the grand challenges. Nature Reviews, Drug Discovery, 2010, 9:253-254.
55) Hamid R, Rotshteyn Y, Rabadi L, Parikh R, Bullock P. Comparison of alamar blue and MTT assays for high through-put screening. Toxicology in Vitro 2004; 18:703-710.
56) Hanahan D, Weinberg R A. Hallmarks of cancer: the next generation. Cell 2011; 144(5):646-74
57) Hanin L. Why victory in the war on cancer remains elusive: biomedical hypotheses and mathematical models. Cancers (Basel) 2011; 3(1):340-67
58) Hayette S, Thomas X, Jallades L, et al. High DNA methyltransferase DNMT3B levels: a poor prognostic marker in acute myeloid leukemia. PLoS One 2012; 7(12):e51527.
59) He S, Shen J, Hong L, Niu L, Niu D. Capecitabine "metronomic" chemotherapy for palliative treatment of elderly patients with advanced gastric cancer after fluoropyrimidine-based chemotherapy. Med Oncol 2012; 29(1):100-6.10.1007/s12032-010-9791-x
60) Hochhaus A, Müller MC, Radich J, Branford S, Kantarjian H M, Hanfstein B, Rousselot P, Kim D W, Lipton J H, Bleickardt E, Lambert A, Hughes T P. Dasatinib-associated major molecular responses in patients with chronic myeloid leukemia in chronic phase following imatinib failure: response dynamics and predictive value. Leukemia. 2009 September; 23(9):1628-33.
61) Hochster H S. Stop and go: yes or no? J Clin Oncol 2009; 27(34):5677-910.
62) Horn L, Dahlberg S E, Sandler A B, Dowlati A, Moore D F, Murren J R, Schiller J H. Phase II study of cisplatin plus etoposide and bevacizumab for previously untreated, extensive-stage small-cell lung cancer. Eastern Cooperative Oncology Group Study E3501. J. Clin Oncol 2009; 27:6006-11.
63) Horton S J, Jaques J, Woolthuis C, van Dijk J, Mesuraca M, Huls G, Morrone G, Vellenga E, Schuringa J J. MLL-AF9-mediated immortalization of human hematopoietic cells along different lineages changes during ontogeny. Leukemia 2013; 27:1116-1126.
64) Hoy S M. Obinutuzumab: A Review of Its Use in Patients with Chronic Lymphocytic Leukaemia. Drugs. 2015 February; 75(3):285-96. doi: 10.1007/s40265-014-0340-3.
65) Huang X, Di Liberto M, Jayabalan D, Liang J, Ely S, Bretz J, Shaffer A L, Louie T, Chen I, Randolph S, Hahn W, Staudt L M, Niesvizky R, Moore M A S, Chen-Kiang S. Prolonged early G1 arrest by selective CDK4/CDK6 inhibition sensitizes myeloma cells to cytotoxic killing through cell cycle-coupled loss of IRF4. Blood. 2012; 120(5):1095-106.
66) Hugate R R, Wilkins R M, Kelly C M, Madsen W, Hinshaw I, Camozzi A B. Intraarterial chemotherapy for extremity osteosarcoma and MFH in adults. Clin Orthop Relat Res. 2008 June; 466(6):1292-301. doi: 10.1007/s11999-008-0252-1.
67) Jahnke K, Thiel E, Bechrakis N E et al. Ifosfamide or trofosfamide in patients with intraocular lymphoma. J. Neurooncol. 2009; 93 (2): 213-7.
68) Jhaveri K, Ochiana S O, Dunphy M P, Gerecitano J F, Corben A D, Peter R I, Janjigian Y Y, Gomes-DaGama 68) E M, Koren J 3rd, Modi S, Chiosis G. Heat shock protein 90 inhibitors in the treatment of cancer: current status and future directions. Expert Opin Investig Drugs. 2014; 23(5):611-28.

69) Jiang Y, Ludwig J, Janku F. Targeted therapies for advanced Ewing's sarcoma family of tumors. Cancer Treatment Rev. On line March 2015 doi:10.1016/i.c-trv.2015.03.008

70) Jo D-Y, Rafii S, Hamada T, Moore M A S. Chemotaxis of primitive hematopoietic cells in response to stromal cell-derived factor-1. J. Clin Invest 2000; 105:101-111.

71) Johnson B E, Janne P A. Epidermal growth factor receptor mutations in patients with non-small cell lung cancer. Cancer Res. 2005, 65:7525-7529.

72) Jordan A M, Khan T H, Malkin H, Helen M I, Osborn H M I. Synthesis and analysis of urea and carbamate prodrugs as candidates for melanocyte-directed enzyme prodrug therapy (MDEPT). Bioorg. Med. Chem. 2002, 10:2625-2633.

73) Jordan A M, Khan T H, Osborn H M I, Photiou A, Riley P A. Melanocyte-directed enzyme prodrug therapy (MDEPT): Development of a targeted treatment for malignant melanoma. Bioorg. Med. Chem. 1999, 7:1775-1780.

74) Kakadiya R, Dong H, Kumar A, Dodiya N, Kapuriya N, Zhang X, Chou T C, Lee T C, Shah A, Su T L. Potent DNA-directed alkylating agents: Synthesis and biological activity of phenyl N-mustard-quinoline conjugates having a urea or hydrazinecarboximide linker. Bioorg. Med. Chem. 2010, 18:2285-2299.

75) Kaldor J M, Day N E, Hemminki K. Quantifying the carcinogenicity of antineoplastic drugs. Eur. J. Cancer Cli. Oncol. 1988, 24:703-711.

76) Kalia M. Personalized oncology: recent advances and future challenges. Metabolism. 2013; 62 Suppl 1:S11-4.

77) Kang Y, Taldone T, Patel H J, Patel P D, Rodina A, Gozman A, Maharaj R, Clement C C, Patel M R, Brodsky J L, Young J C, Chiosis G. Heat shock protein 70 inhibitors. 1. 2,5'-thiodipyrimidine and 5-(phenylthio)pyrimidine acrylamides as irreversible binders to an allosteric site on heat shock protein 70. J Med Chem. 2014; 57(4):1188-207.

78) Kapuriya N, Kakadiya R, Dong H, Kumar A, Lee P C, Zhang X, Chou T C, Lee T C, Chen C H, Lam K, Marvania B, Shah A, Su T L. Design, synthesis, and biological evaluation of novel water-soluble N-mustards as potential anticancer agents. Bioorg. Med. Chem. 2011, 19:471-485.

79) Kapuriya N, Kapuriya K, Dong H, Zhang X, Chou T C, Chen Y T, Lee T C, Lee W C, Tsai T H, Naliapara Y, Su T L. Novel DNA-directed alkylating agents: Design, synthesis and potent antitumor effect of phenyl N-mustard-9-anilinoacridine conjugates via a carbamate or carbonate linker. Bioorg. Med. Chem. 2009, 17:1264-1275.

80) Kapuriya N, Kapuriya K, Zhang X, Chou T C, Kakadiya R, Wu Y T, Tsai T H, Chen Y T, Lee T C, Shah A, Naliapara Y, Su T L. Synthesis and biological activity of stable and potent antitumor agents, aniline nitrogen mustards linked to 9-anilinoacridines via a urea linkage. Bioorg. Med. Chem. 2008, 16:5413-5423.

81) Knaggs S, Malkin H, Osborn H N I, Williams N A O, Yaqoob P. New prodrugs derived from 6-aminodopamine and 4-aminophenol as candidates for melanocyte-directed enzyme prodrug therapy (MDEPT). Org. Biomol. Chem. 2005, 3:4002-4010.

82) Ko Y H, Smith B L, Wang Y et al. Advanced cancers: eradication in all cases using 3-bromopyruvate therapy to deplete ATP. Biochem Biophys Res Commun 2004; 5:324:269-75.

83) Ko Y H, Verhoeven H A, Lee M J, Corbin D J, Vogl T J, Pedersen P L. A translational study "case report" on the small molecule "energy blocker" 3-bromopyruvate (3BP) as a potent anticancer agent: From bench side to bedside. J Bioenergetics Biomembranes 2012; 44 (1): 163-70.

84) Lam K. (DCB) Su T.-L. Unpublished results.

85) Le Chevalier T. Adjuvant chemotherapy for resectable non-small-cell lung cancer: where is it going? Annal Oncol 2010; 21 (Suppl. 7): vii196-198.

86) Lenz H J, Van Cutsem E, Khambata-Ford S, Mayer R J, Gold P, Stella P, Mirtsching B, Cohn A L, Pippas A W, Azarnia N, Tsuchihashi Z, Mauro D J, Rowinsky E K. Multicenter phase II and translational study of cetuximab in metastatic colorectal carcinoma refractory to irinotecan, oxaliplatin, and fluoropyrimidines. J. Clin. Oncol. 2006, 24:4914-4921.

87) Lien K, Georgsdottir S, Sivanathan L, Chan K, Emmenegger U. Low-dose metronomic chemotherapy: a systematic literature analysis. Eur J Cancer. 2013; 49(16):3387-95.

88) Lin L C, Chen Y. F, Lee W C, Wu Y T, Tsa, T. H. Pharmacokinetics of gastrodin and its metabolite p-hydroxybenzyl alcohol in rat blood, brain and bile by microdialysis coupled to LC-MS/MS. J. Pharm. Biomed. Anal. 2008, 48:909-917.

89) Luetke A, Meyers P A, Lewis A, Juergens H. Osteosarcoma treatmentwhere do we stand? A state of the art review. Cancer Treat Rev. 2014; 40 (4): 523-532.

90) MacKenzie K L, Franco S, May C, Sadelain M, Moore M A S. Mass cultured human fibroblasts overexpressing hTERT encounter a growth crisis following an extended period of proliferation. Exp Cell Res 2000, 259:336-350.

91) Malik I A, Mehboobali N, Iqbal M P. Effect of ifosfamide on intracellular glutathione levels in peripheral blood lymphocytes and its correlation with therapeutic response in patients with advanced ovarian cancer. Cancer Chemother Pharmacol. 1997, 39:561-565.

92) Marcucci G, Maharry K, Wu Y, et al. IDH1 and IDH2 gene mutations identify novel molecular subsets within de novo cytogenetically normal acute myeloid leukemia: a Cancer and Leukemia Group B study. J Clin Oncol 2010; 28(14):2348-2355.

93) Marks P A, Breslow R. Dimethyl sulfoxide to vorinostat: development of this histone deacetylase inhibitor as an anticancer drug. Nat Biotechnol. 2007; 25(1): 84-90.

94) Mathupala S P, Ko Y H, Pedersen P L. The pivotal roles of mitochondria in cancer: Warburg and beyond and encouraging prospects for effective therapies. Biochimica et Biophysica Acta (BBA)-Bioenergetics 2010; 1797 (6-7): 1225.

95) Mérino D1, Khaw S L, Glaser S P et al. Bcl-2, Bcl-x(L), and Bcl-w are not equivalent targets of ABT-737 and navitoclax (ABT-263) in lymphoid and leukemic cells. Blood. 2012; 119(24):5807-16.

96) Monneret C. Platinum anticancer drugs. From serendipity to rational design. Ann Pharm Fr. 2011 November; 69(6):286-95

97) Mulloy J C, Cammenga J, Berguido F J, Wu K, Zhou P, Comenzo R L, Jahnwar S, Moore M A S, Nimer S D. Maintaining the self-renewal and differentiation poten- 97) ...tial of human CD34+ hematopoietic stem cells using a single genetic element. Blood. 2003, 102:4369-76.
98) Murray N and Turrisi A T. A review of first-line treatment for small-cell lung cancer. J Thoracic Oncol 2006; 1 (3): 270-278.
99) NSCLC Meta-analysis Collaborative, Group. Preoperative chemotherapy for non-small-cell lung cancer: a systematic review and meta-analysis of individual participant data. Lancet 2014; 383 (9928): 1561-71.
100) O'Brien J. Study sheds light on angiogenesis inhibitors, points to limitations, solutions. UCSF Press Release, Mar. 2, 2009.
101) Orlando L, Cardillo A, Rocca A, Balduzzi A, Ghisini R, Peruzzotti G, et al. Prolonged clinical benefit with metronomic chemotherapy in patients with metastatic breast cancer. Anticancer Drugs (2006) 17(8):961-7.
102) Oronsky B, Carter C A, Mackie V, et al. The War on Cancer: A Military Perspective. Frontiers in Oncology. 2015; 4:387.
103) Oronsky B T, Reid T, Knox S J, and Scicinski J J. The Scarlet Letter of Alkylation: A Mini Review of Selective Alkylating Agents. Transl Oncol. 2012; 5(4): 226-229. Drug Metab Dispos. 2012 September; 40(9): 1810-6.
104) Osborne M R, Lawley P D, Crofton-Sleigh C, Warren W. Products from alkylation of DNA in cells by melphalan: human soft tissue sarcoma cell line RD and *Escherichia coli* WP2. Chem Biol Interact. 1995, 97:287-296.
105) Ottaviani G., Jaffe N. The epidemiology of osteosarcoma. In: Jaffe N. et al. "Pediatric and Adolescent Osteosarcoma. 2009, New York: Springer.
106) Páez-Ribes M, Páez-Ribes M, Allen E, Hudock J, Takeda T, Okuyama H, Viñals F, Inoue M, Bergers G, Hanahan D, Casanovas O. Antiangiogenic therapy elicits malignant progression of tumors to increased local invasion and distant metastasis. Cancer Cell. 2009, 15:220-231.
107) Pao W, Miller V, Zakowski M, Doherty J, Politi K, Sarkaria I, Singh B, Heelan R, Rusch V, Fulton L, Mardis E, Kupfer D, Wilson R, Kris M, Varmus H. EGF receptor gene mutations are common in lung cancers from "never smokers" and are associated with sensitivity of tumors to gefitinib and erlotinib". Proc Nal Acad Sci USA 2004; 101, 36, 13306-13311.
108) Parise R A, Anyang B N, Eiseman J L, Egorin M J, Covey J M, Beumer J H. Formation of active products of benzaldehyde dimethane sulfonate (NSC281612, DMS612) in human blood and plasma and their activity against renal cell carcinoma lines. Cancer Chemother Pharmacol. 2013; 71:73-83.
109) Patel K, Ravandi F, Ma D, et al. Acute myeloid leukemia with IDH1 or IDH2 mutation: frequency and clinicopathologic features. Am J Clin Pathol 2011; 135(1):35-45.
110) Pedersen P L. 3-bromopyruvate (3BP) a fast acting, promising, powerful, specific, and effective "small molecule" anti-cancer agent taken from labside to bedside: Introduction to a special issue". J Bioenergetics Biomembranes 2012; 44: 1-6. doi:10.1007/s10863-012-9425-4.
111) Rai K R, Peterson B L, Appelbaum F R, Kolitz J, Elias L, Shepherd L, Hines J, Threatte G A, Larson R A, Cheson B D, Schiffer C A. Fludarabine compared with chlorambucil as primary therapy for chronic lymphocytic leukemia. N Engl J Med 2000; 343 (24):1750-7.
112) Ravandi F, Patel K, Luthra R, et al. Prognostic significance of alterations in IDH enzyme isoforms in patients with AML treated with high-dose cytarabine and idarubicin. Cancer 2012; 118(10):2665-2673.
113) Roecklein B A and Torok-Storb B. Functionally distinct human marrow stromal cell lines immortalized by transduction with the human papilloma virus E6/E7 genes. Blood 1995 Feb. 15; 85(4):997-1005.
114) Roth J A, Cristiano R G. Gene therapy for cancer: what have we done and where are we going? J. Natl. Cancer Inst. 1997, 89:21-30.
115) Rudin C M, Hann C L Garon E B et al. Phase II Study of Single-Agent Navitoclax (ABT-263) and Biomarker Correlates in Patients with Relapsed Small Cell Lung Cancer. Clin Cancer Res 2012 18 (11): 3163-3169 doi: 10.1158/1078-0432.CCR-11-3090.
116) Saito K, Matsumoto S, Devasahayam N, Subramanian S, Munasinghe J P, Morris H D, Lizak M J, Ardenkjaer-Larsen J H, Mitchell J B, Krishna M C: Transient decrease in tumor oxygenation after intravenous administration of pyruvate. Magn Reson Med 2012, 67:801-807.
117) Sawyers C L. The 2011 Gordon Wilson Lecture: overcoming resistance to targeted cancer drugs. Trans Am Clin Climatol Assoc. 2012; 123:114-23; discussion 123-5.
118) Sawyers C L, van 't Veer L J. Reliable and effective diagnostics are keys to accelerating personalized cancer medicine and transforming cancer care: a policy statement from the American Association for Cancer Research. Clin Cancer Res. 2014; 20(19):4978-81.
119) Sawyers C L. Opportunities and challenges in the development of kinase inhibitor therapy for cancer. Genes Dev. 2003, 17:2998-3010.
120) Schuringa J J, Chung K Y, Morrone G, Moore M A S. Constitutive activation of STATS promotes human hematopoietic stem cell self-renewal and erythroid differentiation. J Exp Med. 2004, 200:623-635.
121) Seedhouse C H, Hunter H M, Lloyd-Lewis B, Massip A-M, Pallis M, Carter G I, Grundy M, Shang 1 S, Russell N H. DNA repair contributes to the drug-resistant phenotype of primary acute myeloid leukaemia cells with FLT3 internal tandem duplications and is reversed by the FLT3 inhibitor PKC412. Leukemia, 2006, 20:2130-2136.
122) Shah N P, Tran C, Lee F Y, Chen P, Norris D, Sawyers C L. Overriding imatinib resistance with a novel ABL kinase inhibitor. Science 2004, 305:399-32
123) Shaykhiev et al 2013, Shaykhiev R, Wang R, Zwick R K, Hackett N R, Leung R, Moore M A, Sima C S, Chao I W, Downey R J, Strulovici-Barel Y, Salit J, Crystal R G. Airway basal cells of healthy smokers express an embryonic stem cell signature relevant to lung cancer. Stem Cells. 2013; 31(9):1992-2002.
124) Siddik Z H. Mechanisms of Action of Cancer Chemotherapeutic Agents: DNA-Interactive Alkylating Agents and Antitumour Platinum-Based Drugs. 2005; John Wiley & Sons, Ltd.
125) Silva A S, Kam Y, Khin Z P, Minton S E, Gillies R J, Gatenby R A. Evolutionary approaches to prolong progression-free survival in breast cancer. Cancer Res 2012; 72(24):6362-70.
126) Stevens M F G., Hickman J A, Stone R, Gibson N W, Baig G. U, Lunt E, Newton C G. Antitumour imidazotetrazines. 1. Synthesis and chemistry of 8-carbamoyl-3-(2-chloroethyl)-imidazo-[5,1-d]1,2,3,5-tetrazin-4(3H)-one, a novel broad-spectrum antitumour agent. J. Med. Chem. 1984, 27, 196-201.
127) Torre L A, Bray F, Siegel R L, Ferlay J, Lortet-Tieulent J, Jemal A. Global cancer statistics, 2012. CA Cancer J Clin 2015 March; 65(2):87-108. doi: 10.3322/caac.21262. Epub 2015 Feb. 4.
128) Travis W D, Brambilla E, Muller-Hermelink H K, Harris C C (Eds.): World Health Organization Classification of Tumours. Pathology and Genetics of Tumours of the Lung, Pleura, Thymus and Heart. IARC Press: Lyon, France 2004.
129) Tsai T H, Su T L. Unpublished results.
130) Turturro F, Leary C, Stephens J, Veillon D, Lowery-Nordberg M. Caution using hypomethylating agents in myelodysplasia or myeloid leukemia with complex cytogenetics. J Clin Oncol. 2010 Aug. 1; 28(22):e380-1.
131) Walters M S, Gomi K, Ashbridge B, Moore M A, Arbelaez V, Heldrich J, Ding B S, Rafii S, Staudt M R, Crystal R G. Generation of a human airway epithelium derived basal cell line with multipotent differentiation capacity. Respir Res. 2013; 14:135-. doi: 10.1186/1465-9921-14-135.
132) Warshamana-Greene G, Litz J, Buchdunger E, Garcia-Echeverria C, Hofmann F, Krystal G. The insulin-like growth factor-I receptor kinase inhibitor, NVP-ADW742, sensitizes small cell lung cancer cell lines to the effects of chemotherapy. Clin Cancer Res, 2005, 11:1563-1571.
133) Wei J, Wunderlich M, Fox C, Alvarez S, Cigudosa J C, Wilhelm J S, Zheng Y, Cancelas J A, Gu Y, Jansen M, Dimartino J F, Mulloy J C. Microenvironment Determines Lineage Fate in a Human Model of MLL-AF9 Leukemia. Cancer Cell 2008; 13:483-495.
134) Weiss G J, Infante J R, Chiorean E G Borad B J, Bendel! JC, JR Molina, Tibes R, Ramanathan R K, Lewandowski K, Jones S F, Lacouture M E, Langmuir V K, Lee H, Kroll S, Burris III H A. Phase 1 Study of the Safety, Tolerability, and Pharmacokinetics of TH-302, a Hypoxia-Activated Prodrug, in Patients with Advanced Solid Malignancies. Clin Cancer Res. 2011; 17(9):2997-3004.
135) Wen V W, Wu K, Baksh S, Hinshelwood R A, Lock R B, Clarke S J, Moore M A S, MacKenzie K L. Telomere-driven karyotypic complexity concurs with $p16^{INK4a}$ inactivation in TP53-competent immortal endothelial cells. Cancer Research. 2006, 66:10691-10700.
136) Wheate N J, Walker S, Craig G E, Oun R. The status of platinum anticancer drugs in the clinic and in clinical trials. Dalton Transactions 2010; 39 (35): 8113-27.
137) Wright G, Tan B, Rosenwald A, Hurt E H, Wiestner A, Staudt L M. A gene expression-based method to diagnose clinically distinct subgroups of diffuse large B cell lymphoma. Proc Nat Acad Sci 2003; 100 (17): 9991-96.
138) Wu K-D, Cho Y S, Katz J, Ponomarev V Chen-Kiang S, Danishefsky S J, Moore M A S. Investigation of anti-tumor effects of synthetic epothilone analogs in human myeloma models in vitro and in vivo. Proc Natl Acad Sci USA. 2005, 102; 10640-10645.
139) Wunderlich M, Mulloy J C. Model systems for examining effects of leukemia-associated oncogenes in primary human CD34+ cells via retroviral transduction. Methods Mol Biol. 2009; 538:263-85.

What is claimed is:

1. A method of treating cancer in a patient in need thereof, comprising administering to said patient a therapeutically effective amount of ureidomustine, wherein said cancer is selected from the group consisting of acute myeloid leukemia (AML).

2. The method according to claim 1, wherein said cancer is acute myeloid leukemia (AML).

3. The method according to claim 1, wherein said method results in a therapeutically significant reduction in the number of said cancer cells and does not result in significant toxicities against non-malignant tissues.

4. The method according to claim 1, wherein said ureidomustine is formulated as a pharmaceutical composition.

5. The method according to claim 1, further comprising administration of another anti-cancer active agent to said patient.

* * * * *